US012668659B2

(12) United States Patent
Hayek et al.

(10) Patent No.: US 12,668,659 B2
(45) Date of Patent: Jun. 30, 2026

(54) COPOLY(1,2,4-TRIAZOLE)S MEMBRANES FOR SOUR MIXED-GAS SEPARATION APPLICATIONS

(71) Applicant: Saudi Arabian Oil Company, Dhahran (SA)

(72) Inventors: Ali Hayek, Dhahran (SA); Abdulkarim Alsamah, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 204 days.

(21) Appl. No.: 18/335,679

(22) Filed: Jun. 15, 2023

(65) Prior Publication Data

US 2025/0066537 A1 Feb. 27, 2025

(51) Int. Cl.

*C08G 73/08* (2006.01)
*B01D 53/22* (2006.01)
*B01D 71/62* (2006.01)
*C07C 7/144* (2006.01)
*C08G 61/12* (2006.01)
*C10L 3/10* (2006.01)

(52) U.S. Cl.

CPC ......... *C08G 61/124* (2013.01); *B01D 53/228* (2013.01); *B01D 71/62* (2013.01); *C07C 7/144* (2013.01); *C08G 61/123* (2013.01); *C08G 73/08* (2013.01); *C10L 3/103* (2013.01); *C10L 3/104* (2013.01); *B01D 2256/245* (2013.01); *B01D 2257/304* (2013.01); *B01D 2257/504* (2013.01); *B01D 2323/30* (2013.01); *C08G 2261/124* (2013.01); *C08G 2261/148* (2013.01); *C08G 2261/312* (2013.01); *C08G 2261/334* (2013.01); *C08G 2261/72* (2013.01); *C08G 2261/76* (2013.01); *C10L 2290/548* (2013.01)

(58) Field of Classification Search

None

See application file for complete search history.

(56) References Cited

U.S. PATENT DOCUMENTS

| | | | |
|---|---|---|---|
| 3,413,267 | A | 11/1968 | Kreuz |
| 3,422,061 | A | 1/1969 | Gall |
| 3,621,076 | A | 11/1971 | Winter et al. |
| 3,661,849 | A | 5/1972 | Culbertson |
| 3,705,869 | A | 12/1972 | Darmory et al. |
| 3,941,749 | A | 3/1976 | Frost |
| 4,962,183 | A | 10/1990 | Chen, Sr. et al. |
| 5,042,992 | A | 8/1991 | Blinka |
| 5,306,476 | A | 4/1994 | Jalan et al. |
| 5,779,879 | A | 7/1998 | Dieterich et al. |
| 6,531,569 | B1 | 3/2003 | Tachiki |
| 6,692,528 | B2 | 2/2004 | Ward et al. |
| 7,279,237 | B2 | 10/2007 | Thompson et al. |
| 9,962,646 | B2 | 5/2018 | Yahaya et al. |
| 10,913,036 | B2 | 2/2021 | Yahaya et al. |
| 11,007,491 | B2 | 5/2021 | Yahaya et al. |
| 11,007,492 | B2 | 5/2021 | Yahaya et al. |
| 11,642,629 | B2 | 5/2023 | Yahaya et al. |
| 11,896,936 | B2 | 2/2024 | Hayek et al. |
| 2003/0097003 | A1 | 5/2003 | Lindsay et al. |
| 2003/0105270 | A1 | 6/2003 | Lindsay et al. |
| 2005/0045874 | A1 | 3/2005 | Xiao et al. |
| 2007/0068382 | A1 | 3/2007 | Ku et al. |
| 2010/0075393 | A1 | 3/2010 | Shear et al. |
| 2011/0130611 | A1 | 6/2011 | Gonzalez et al. |
| 2016/0177035 | A1 | 6/2016 | Liu |
| 2016/0310913 | A1 | 10/2016 | Wu et al. |
| 2018/0339275 | A1 | 11/2018 | Kitamura et al. |
| 2018/0345229 | A1 | 12/2018 | Yahaya et al. |
| 2019/0329190 | A1 | 10/2019 | Kim et al. |
| 2020/0070107 | A1 | 3/2020 | Maab et al. |
| 2020/0269195 | A1 | 8/2020 | Yahaya et al. |
| 2020/0269196 | A1 | 8/2020 | Yahaya et al. |
| 2021/0309803 | A1 | 10/2021 | Hayek |
| 2021/0395456 | A1 | 12/2021 | Liu et al. |
| 2022/0017688 | A1 | 1/2022 | Maab et al. |
| 2022/0017774 | A1 | 1/2022 | Maab et al. |
| 2022/0219127 | A1 | 7/2022 | Hayek et al. |
| 2024/0024828 | A1 | 1/2024 | Hayek et al. |
| 2024/0150519 | A1 | 5/2024 | Hayek et al. |
| 2025/0066537 | A1* | 2/2025 | Hayek ..................... C07C 7/144 |

FOREIGN PATENT DOCUMENTS

| | | | |
|---|---|---|---|
| CN | 103450029 | A | 12/2013 |
| CN | 110467728 | A | 11/2019 |
| CN | 113713639 | A | 11/2021 |
| CN | 114797506 | A | 7/2022 |
| CN | 114797507 | A | 7/2022 |
| CN | 116272441 | A | 6/2023 |
| CN | 117018896 | A | 11/2023 |
| JP | 2006003715 | A | 1/2006 |

(Continued)

OTHER PUBLICATIONS

Bruma et al., "Polyimides Containing 1,3,4-Oxadiazole Rings," Collection of Czechoslovak Chemical Communications, 2008, 73(12):1631-1644, 14 pages.
Cristea et al., "Thermal behavior of aromatic polyamic acids and polyimides containing oxadiazole rings," Journal of Thermal Analysis and Calorimetry, Jul. 1, 2008, 93(1):63-68, 6 pages.
Dămăceanu et al., "Polymers containing 1,3,4-oxadiazole rings for advanced materials," Memoirs of the Scientific Sections of the Romanian Academy, 2011, 34, 24 pages.
Dămăceanu et al., "Tuning of the color of the emitted light from new polyperyleneimides containing oxadiazole and siloxane moieties," Dyes and Pigments, Oct. 2013, 99(1), 46 pages.
Fan et al., "Zn(II)-modified imidazole containing polyimide/ZIF-8 mixed matrix membranes for gas separations," Journal of Membrane Science, Mar. 1, 2020, 597, 117775, 10 pages.

(Continued)

*Primary Examiner* — David J Buttner
(74) *Attorney, Agent, or Firm* — Fish & Richardson P.C.

(57) ABSTRACT

This disclosure relates to polymers and polymeric membranes that incorporate functionalized copoly(1,2,4-triazole)s. The polymers and polymeric membranes can be used in sour natural gas separation applications.

18 Claims, 22 Drawing Sheets

(56) References Cited

FOREIGN PATENT DOCUMENTS

| | | | |
|---|---|---|---|
| JP | 2013176755 | A | 9/2013 |
| KR | 20170079606 | A | 7/2017 |
| WO | WO 2011143530 | A1 | 11/2011 |
| WO | WO 2016100058 | A1 | 6/2016 |
| WO | WO 2017145747 | A1 | 8/2017 |
| WO | WO 2022/123497 | | 6/2022 |

OTHER PUBLICATIONS

Frost et al., "Benzimidazole-and oxadiazole-modified aromatic polyimides," Journal of Polymer Science Part A-1: Polymer Chemistry, Jan. 1968, 6(1):215-233, 19 pages.

Gan et al., "Constructing Gas Molecule Transport Channels in Thermally Rearranged Multiblock Poly(benzoxazole-co-imide) Membranes for Effective $CO_2/CH_4$ Separation," ACS Sustainable Chemistry & Engineering, May 21, 2020, 8(26):9669-9679, 40 pages.

Gan et al., "Preparation of thermally rearranged poly(benzoxazole-co-imide) membranes containing heteroaromatic moieties for $CO_2/CH_4$ separation," Polymer, Dec. 17, 2019, 185, 121945, 36 pages.

Grabiec et al., "Poly(amide imides) and Poly(ether imides) Containing 1,3,4-Oxadiazole or Pyridine Rings: Characterizations and Optical Properties," The Journal of Physical Chemistry A, Jan. 26, 2009, 113(8):1481-1488, 8 pages.

Grucela-Zajac et al., "Photophysical, electrochemical and thermal properties of new (co)polyimides incorporating oxadiazole moieties," Synthetic Metals, Feb. 2014, 188:161-174, 14 pages.

Hamciuc et al., "Poly(1,3,4-oxadiazole-imide)s and their polydimethlsiloxane-containing copolymers," European Polymer Journal, Nov. 2007, 43(11):4793-4749, 11 pages.

Hamciuc et al., "Poly(1,3,4-oxadiazole-imide)s containing dimethylsilane groups," European Polymer Journal, Dec. 2005, 41(12):2989-2997, 9 pages.

Hamciuc et al., "Synthesis and photophysical study of some new highly thermostable blue fluorescent poly(1,3,4-oxadiazole-imide)s containing dimethylamine groups," Reactive and Functional Polymers, Jun. 2016, 103:17-25, 9 pages.

Hossain et al., "A Facile Synthesis of (PIM-Polyimide)-(6FDADurene-Polyimide) Copolymer as Novel Polymer Membranes for $CO_2$ Separation," Membranes, Aug. 31, 2019, 9(9), 113, 14 pages.

Hsu et al., "Electroluminescence and electron transport characteristics of aromatic polyimides containing 1,3,4-oxadiazole moiety," Thin Solid Films, Jun. 13, 2007, 515(17):6943-6948, 6 pages.

Li et al., "A facile synthesis of soluble polyimides with high glass transition temperature and excellent mechanical properties due to intermolecular hydrogen bonds," High Performance Polymers, Jul. 11, 2019, 32(3), 8 pages.

Li et al., "Improved selectivity and anti-aging ability for 6FDA type carbon molecular sieve membranes by mixing silicon from macrophase separation to molecule doping," Separation and Purification Technology, Sep. 1, 2023, 320(9), 124168, 11 pages.

Liang et al., "Effects on Carbon Molecular Sieve Membrane Properties for a Precursor Polyimide with Simultaneous Flatness and Contortion in the Repeat Unit," ChemSusChem, Oct. 21, 2020, 13(20):5531-5538, 9 pages.

Luo et al., "A Side-Chain Dendronized Nonlinear Optical Polyimide with Large and Thermally Stable Electrooptic Activity," Macromolecules, 2004, 37(2):248-250, 3 pages.

Pavlova et al., "Dependence of the conformational parameters of polyimides on the chemical structure of the chain," Journal of Polymer Science: Polymer Physics Edition, Jun. 1980, 18(6):1175-1186, 12 pages.

PCT International Search Report and Written Opinion in International Appln. No. PCT/US2022/012339, mailed on May 9, 2022, 14 pages.

Robeson et al., "The Upper Bound Revisited," Journal of Membrane Science, Jul. 15, 2008, 320(1-2):390-400, 11 pages.

Rusu et al., "Copoly(peryleneimide)s containing 1,3,4-oxadiazole rings: Synthesis and properties," Journal of Polymer Science: Part A, Oct. 1, 2010, 48(19):4230-4242, 13 pages.

Rusu et al., "n-Type Polyimides Incorporating Oxadiazole and perylene fluorophores," Environmental Engineering and Management Journal, Jan. 2019, 18(1):89-98, 10 pages.

Sanaeepur et al., "Polyimides in membrane gas separation: monomer's molecular design and structural engineering," Progress in Polymer Science, Apr. 2019, 91, 154 pages.

Shaplov et al., "Turning into poly(ionic liquid)s as a tool for polyimide modification: synthesis, characterization and CO2 separation properties," Polymer Chemistry, 2016, 7(3):580-591, 12 pages.

Shi et al., "Enhancing the $CO_2$ plasticization resistance of thin polymeric membranes by designing Metal-polymer complexes," Separation and Purification Technology, May 15, 2022, 289, 120699, 10 pages.

Shi et al., "Micrometer-sized MOF particles incorporated mixed-matrix membranes driven by $\pi$-$\pi$ interfacial interactions for improved gas separation," Separation and Purification Technology, Aug. 15, 2022, 295, 121258, 11 pages.

Shi et al., "Synergistic Design of Enhanced $\pi$-$\pi$ Interaction and Decarboxylation Cross-Linking of Polyimide Membranes for Natural Gas Separation," Macromolecules, Mar. 17, 2022, 55(7):2970-2982, 13 pages.

Wu et al., "A novel hydroxyl-containing polyimide as a colorimetric and ratiometric chemosensor for the reversible detection of fluoride ions," Polymer Chemistry, 2019, 10(11), 8 pages.

Wu et al., "Facile fabrication of a fluorene-containing polyimide film-based fluorescent sensor for rapid and selective detection of fluoride ion," Journal of Photochemistry and Photobiology A: Chemistry, Mar. 1, 2022, 425, 113728, 7 pages.

Wu et al., "Facile synthesis of acyloxy-containing fluorene-based Cardo polyimides with high optical transparency, fluorescence and low dielectric constant," Reactive and Functional Polymers, Sep. 2021, 166, 104979, 9 pages.

Wu et al., "Multifunctional polyimides by direct silyl ether reaction of pendant hydroxy groups: Toward low dielectric constant, high optical transparency and fluorescence," European Polymer Journal, Jun. 5, 2020, 132, 109742, 8 pages.

Wu et al., "Ratiometric and colorimetric sensors for highly sensitive detection of water in organic solvents based on hydroxyl-containing polyimide-fluoride complexes," Analytica Chimica Acta, Apr. 29, 2020, 1108:37-45, 9 pages.

Wu et al., "Simultaneously Improving the Optical, Dielectric, and Solubility Properties of Fluorene-Based Polyimide with Silyl Ether Side Groups," ACS Omega, Apr. 1, 2022, 7(14):11939-11945, 7 pages.

Wu et al., "Synthesis and properties of cardo-type polyimides containing hydroxyl groups for application in specific detection of fluoride ion," Dyes and Pigments, Feb. 2020, 173, 107924, 8 pages.

Xie et al., "Highly Selective Benzimidazole-Based Polyimide/Ionic Polyimide Membranes for Pure- and Mixed-Gas $CO_2/CH_4$ Separation," Separation and Purification Technology, Feb. 1, 2022, 282, 120091, 9 pages.

Xu et al., "A fluorescent copolyimide containing perylene, fluorene and oxadiazole units in the main chain," Reactive and Functional Polymers, Apr. 2006, 66(4):471-478, 8 pages.

Xu et al., "Ionic polyimide membranes containing Tröger's base: Synthesis, microstructure and potential application in $CO_2$ separation," Journal of Membrane Science, May 1, 2020, 602, 117967, 8 pages.

Yang et al., "Nonvolatile write-once read-many-times memory behaviors of polyimides containing tetraphenyl fluorene core and the pendant triphenylamine or carbazole moieties," Journal of Polymer Science Part A: Polymer Chemistry, Aug. 1, 2018, 56(15):1630-1644, 15 pages.

Yang et al., "Synthesis and resistive switching characteristics of polyimides derived from 2,7-aryl substituents tetraphenyl fluorene diamines," European Polymer Journal, Nov. 2018, 108:85-97, 13 pages.

(56) References Cited

OTHER PUBLICATIONS

Yuan et al., "Imputation of missing gas permeability data for polymer membranes using machine learning," Journal of Membrane Science, Jun. 1, 2021, 627, 119207, 10 pages.
Yuan et al., "Performance optimization of imidazole containing copolyimide/functionalized ZIF-8 mixed matrix membrane for gas separations," Journal of Membrane Science, Feb. 15, 2022, 644, 120071, 8 pages.
Zhang et al., "A Rigid and Planar Aza-Based Ternary Anhydride for the Preparation of Cross-Linked Polyimide Membrane Displaying High $CO_2/CH_4$ Separation Performance," Polymers, Jan. 19, 2022, 14(3), 389, 13 pages.
Zhang et al., "Carbon Molecular Sieve Membranes with a Rationally Designed Polymer Precursor for Improved Propane/Propylene Separation," Industrial & Engineering Chemistry Research, Oct. 23, 2023, 62(44):18662-18671, 10 pages.
Zhang et al., "Enhanced gas separation and mechanical properties of fluorene-based thermal rearrangement copolymers," RSC Advances, Apr. 7, 2021, 11(22):13164-13174, 11 pages.
Zhao et al., "Mixed matrix membranes incorporating amino-functionalized ZIF-8-$NH_2$ in a carboxylic polyimide for molecularly selective gas separation," Journal of Membrane Science, Feb. 2024, 693, 122326, 11 pages.
Zhuang et al., "Mechanically Tough, Thermally Rearranged (TR) Random/Block Poly(benzoxazole-co-imide) Gas Separation Membranes," Macromolecules, Jul. 28, 2015, 48(15):5286-5299, 14 pages.
Chisca et al., "Crosslinked copolyazoles with a zwitterionic structure for organic solvent resistant membranes," Polym. Chem., 2015, 6:543-554, 13 pages.
Chisca et al., "Crosslinked polytriazole membranes for organophilic filtration," J. Membr. Sci. 2017, 528, 264-272, 9 pages.
Chisca et al., "Polytriazole membranes with ultrathin tunable selective layer for crude oil fractionation," Science, Jun. 2022, 376(6597):1105-1110, 6 pages.
Chisca et al., "Thermal treatment of hydroxyl functionalized polytriazole and its effect on gas transport: From crosslinking to carbon molecular sieve," J. Membr. Sci. 2021, 642, 119963, 40 pages.
Comesaña-Gándara et al., "Redefining the Robeson Upper Bounds for $CO_2/CH_4$ and $CO_2/N_2$ Separations Using a Series of Ultrapermeable Benzotriptycene-Based Polymers of Intrinsic Microporosity," Energy Environ. Sci., Jul. 2019, 12(9):2733-2740, 8 pages.
Duong et al., "Hydroxyl Functionalized Polytriazole-co-polyoxadiazole as Substrates for Forward Osmosis Membranes," ACS Appl. Mater. Interfaces., Feb. 2015, 7(7):3960-3973, 14 pages.
Maab et al. "Polyazole polymers membranes for high pressure gas separation technology," J. Membr. Sci. Feb. 2022, 642, 119980, 14 pages.
Hayek et al., "Unprecedented Sour Mixed-Gas Permeation Properties of Fluorinated Polyazole-Based Membranes," ACS Appl. Polym. Mater., May 2020, 2, 2199-2210, 12 pages.
Hensema et al., "Gas separation properties of new polyoxadiazole and polytriazole membranes," Gas Sep. & Purif. 1994, 8(3):149-160, 12 pages.
Hensema et al., "Syntheses and Properties of Related Polyoxadiazoles and Polytriazoles," J. Polym. Sci. Part A: Polym. Chem., Feb. 1994, 32(3):527-537, 11 pages.
Holsten et al., "Aromatic Poly(phenylene)4-phenyl-1,2,4-triazoles," Lilyquist Journal of Polymer Science: Part A, Nov. 1965, 3(11):3905-3917, 13 pages.
Robeson, "The Upper Bound Revisited," J. Membr. Sci., Jul. 2008, 320(1):390-400, 11 pages.
Wu et al., "Copoly(p-phenylenes)s Containing Bipolar Triphenylamine and 1,2,4-Triazole Groups: Synthesis, Optoelectronic Properties, and Applications," Journal of Polymer Science: Part A: Polymer Chemistry, Dec. 2010, 48(24):5727-5736, 10 pages.

* cited by examiner

FPT-Ph(OH)/Ph($Me_2$) (1:0.82)

COPOLY(1,2,4-TRIAZOLE)S MEMBRANES FOR SOUR MIXED-GAS SEPARATION APPLICATIONS

TECHNICAL FIELD

This document relates to methods and compositions used in natural gas purification technology.

BACKGROUND

Various classes of polymeric membranes can be used in gas separation technologies. For example, polyimides and polyazoles have applications in sour mixed-gas separation. Typically, polymeric membranes used in gas separation exhibit a permeability-selectivity trade-off. Over time, however, membranes can suffer from reduced performance.

For sour mixed-gas separation, ideal polymers form membranes with high $CO_2$ and/or $H_2S$ permeability coefficients, with high to moderate $CO_2/CH_4$ and/or $H_2S/CH_4$ selectivity coefficients. Ideal polymers and membranes can also withstand the harsh chemical, physical, and thermal conditions that occur during natural gas purification.

SUMMARY

Provided in the present disclosure are copoly(1,2,4-triazole)s. In some embodiments, the copoly(1,2,4-triazole)s described in this disclosure include repeats of Formula VIIa and VIIIa:

(VIIa)

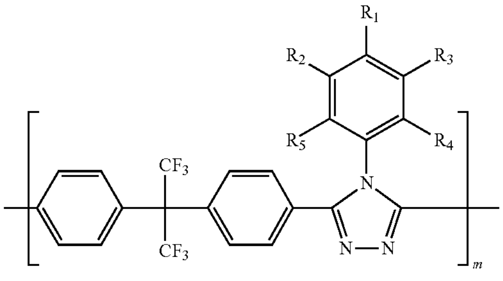

; and (VIIIa)

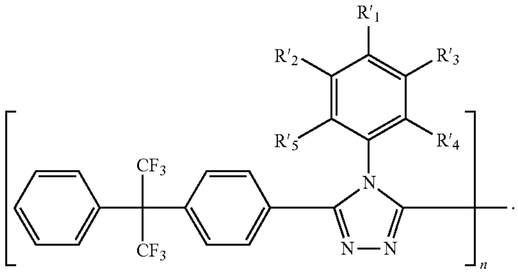

In some embodiments of Formula VIIa, $R^1$-$R^5$ are each independently selected from hydrogen, alkyl, hydroxyl, alkoxy, halogen, aromatic, and cyclic functional groups.

In some embodiments of Formula VIIIa, $R'^1$-$R'^5$ are each independently selected from hydrogen, alkyl, hydroxyl, alkoxy, halogen, aromatic, and cyclic functional groups. The ratio of m:n can vary between 1:10 and 10:1. For any segment of a polymer that includes a monomer unit of formula VIIa and a monomer unit of formula VIIIa, m and n represent the number of repetitive units in each segment and their corresponding ratio m:n varies between 1 and 9. For example, m=1 and n=9, m=2 and n=8, m=3 and n=7, m=4 and n=6, m=5 and n=5, m=6 and n=4, m=7 and n=3, m=8 and n=2, or m=9 and n=1.

In some embodiments, in a polymer that includes monomer units of Formula VIIa and Formula VIIIa, at least one of $R^1$-$R^5$ and at least one of $R'^1$-$R'^5$ is not hydrogen, and at least one of $R^1$-$R^5$ is different from at least one of $R'^1$-$R'^5$. In some embodiments, in a polymer that includes monomer units of Formula VIIa and Formula VIIIa, $R^1$ is hydroxyl and $R^2$-$R^5$ are each hydrogen. In some embodiments, in a polymer that includes monomer units of Formula VIIa and Formula VIIIa, $R'^1$ is tert-butyl and $R'^2$—$R'^5$ are each hydrogen. In some embodiments, in a polymer that includes monomer units of Formula VIIa and Formula VIIIa, $R'^2$ is methyl, $R'^3$ is methyl, and $R'^1$, $R'^4$, and $R'^5$ are each hydrogen. In some embodiments, in a polymer that includes monomer units of Formula VIIa and Formula VIIIa, $R'^1$ is fluoro, $R'^2$ is —$CF_3$, and $R'^3$—$R'^4$ are each hydrogen. In some embodiments, in a polymer that includes monomer units of Formula VIIa and Formula VIIIa, $R^2$ is —$CH_2$—Br, $R^3$ is methyl, and $R^1$, $R^4$, and $R^5$ are each hydrogen. In some embodiments, $R^1$ is hydroxyl, $R^2$-$R^5$ are each hydrogen, $R'^1$ is tert-butyl, and $R'^2$—$R'^5$ are each hydrogen. In some embodiments, $R^1$ is hydroxyl, $R^2$-$R^5$ are each hydrogen, $R'^2$ and $R'^3$ are both methyl, and $R'^1$, $R'^4$, and $R'^5$ are each hydrogen. In some embodiments, $R^1$ is hydroxyl, $R^1$-$R^5$ are each hydrogen, $R'^1$ is —F, $R'^2$ is —$CF_3$, and $R'^3$—$R'^5$ are each hydrogen.

In some embodiments, in a polymer that includes monomer units of Formula VIIa and Formula VIIIa, the polymer includes the monomer unit of Formula VIIa and the monomer unit of Formula VIIIa in a molar ratio of about 10:1 to about 1:10. In some embodiments, in a polymer that includes monomer units of Formula VIIa and Formula VIIIa, the polymer includes the monomer unit of Formula VIIa and the monomer unit of Formula VIIIa in a molar ratio of about 2:1 to about 1:2. In some embodiments, in a polymer that includes monomer units of Formula VIIa and Formula VIIIa, the polymer includes the monomer unit of Formula VIIa and the monomer unit of Formula VIIIa in a molar ratio of about 1:1. In some embodiments, a polymer that includes monomer units of Formula VIIa and Formula VIIIa has a number-average molecular weight of about 1,000 g/mol to about 1,000,000 g/mol. In some embodiments, a polymer that includes monomer units of Formula VIIa and Formula VIIIa is covalently crosslinked.

In some embodiments, a membrane includes a polymer that includes monomer units of Formula VIIa and Formula VIIIa. In some embodiments of the membrane, at least one of $R^1$-$R^5$ and at least one of $R'^1$—$R'^5$ is not hydrogen, and at least one of $R^1$-$R^5$ is different from at least one of $R'^1$—$R'^5$. In some embodiments of the membrane, $R^1$ is hydroxyl and $R^2$-$R^5$ are each hydrogen. In some embodiments of the membrane, $R'^1$ is tert-butyl and $R'^2$—$R'^5$ are each hydrogen. In some embodiments of the membrane, $R'^2$ is methyl, $R'^3$ is methyl, and $R'^1$, $R'^4$, and $R'^5$ are each hydrogen. In some embodiments of the membrane, $R'^1$ is fluoro, $R'^2$ is —$CF_3$, and $R'^3$—$R'^5$ are each hydrogen. In some embodiments of the membrane, $R^2$ is —$CH_2$—Br, $R^3$ is methyl, and $R^1$, $R^4$, and $R^5$ are each hydrogen. In some embodiments, $R^1$ is hydroxyl, $R^2$-$R^5$ are each hydrogen, $R'^1$ is tert-butyl, and $R'^2$—$R'^5$ are each hydrogen. In some embodiments, $R^1$ is hydroxyl, $R^2$-$R^5$ are each hydrogen, $R'^2$ and $R'^3$ are both methyl, and $R'^1$, $R'^4$, and $R'^5$ are each hydrogen. In some embodiments, $R^1$ is hydroxyl, $R^1$-$R^5$ are each hydrogen, $R'^1$ is —F, $R'^2$ is —$CF_3$, and $R'^3$—$R'^5$ are each hydrogen.

In some embodiments of the membrane, the polymer is covalently crosslinked. In some embodiments of the membrane, the membrane includes at least about 80% by weight of the polymer.

In some embodiments, a method for separating $CO_2$ and $H_2S$ from natural gas includes introducing a natural gas stream to the membrane and separating the $CO_2$ and $H_2S$ from the natural gas stream.

The details of one or more implementations of the disclosure are set forth in the accompanying drawings and the description that follows. Other features, objects, and advantages of the disclosure will be apparent from the description and drawings, and from the claims.

DESCRIPTION OF DRAWINGS

Like reference symbols in the various drawings indicate like elements.

DETAILED DESCRIPTION

Figure 1:
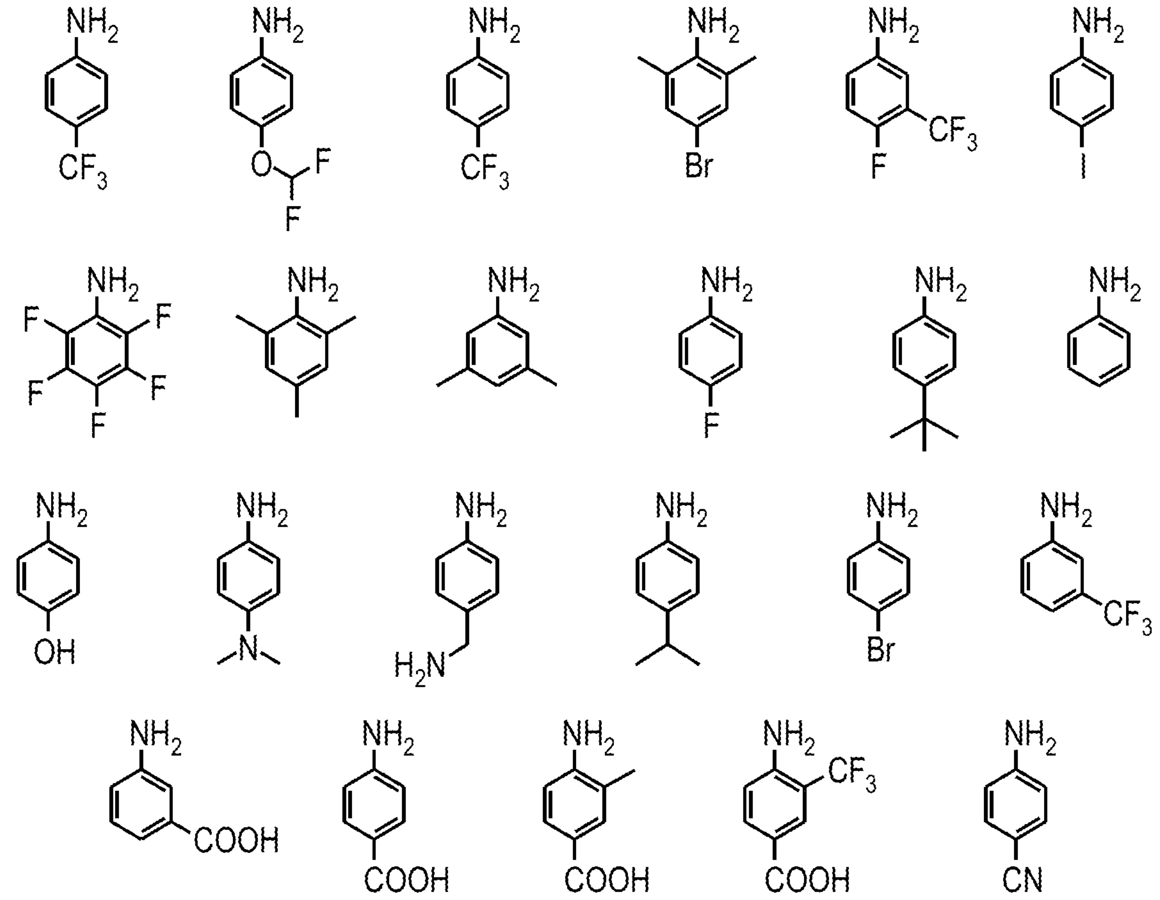
FIG. 1 shows a group of aniline derivatives.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

This disclosure describes gas separation membrane materials that include copoly(1,2,4-triazole)s. The membranes can be used in natural gas purification technology. The chemical structure of copoly(1,2,4-triazole)s include a polymer backbone that can include aromatic rings and 1,2,4-triazole rings. The 1,2,4-triazole rings can be functionalized with additional aromatic substituents. The aromatic substituents attached to the 1,2,4-triazole rings can contain a variety of functional groups to tailor the gas permeation properties of their corresponding membranes, in addition to fine tuning the chemical and physical properties of the polymer.

The preparation methodology of the copoly(1,2,4-triazole)s polymeric materials includes the preparation of a poly(1,3,4-oxadizole) or copoly(1,3,4-oxadizole) backbone, and conversion of the 1,3,4-oxadizole ring into 1,2,4-triazole rings using two or more aniline derivatives containing select functional groups. By including two different aniline derivatives, the chemical and physical properties of the membranes that include the copoly(1,2,4-triazole)s can be tailored to specific needs. In addition, the combination of two different aniline derivatives can result in synergistic or emergent properties not seen with a comparable monomer with only one type of aniline derivative.

Further, the synthetic methodology allows for the preparation of a large variety of new polymers, with distinct chemical, physical, and mechanical properties. Moreover, the gas permeation properties of the resulting membranes can be tailored to target specific characteristics in terms of productivity (for example, permeability) and efficiency (for example, selectivity). In addition, the copoly(1,2,4-triazole)s membranes can be regenerated with annealing and show improved $CO_2/CH_4$ selectivity following regeneration. Accordingly, the copoly(1,2,4-triazole)s represent an attractive and commercially valuable structure.

Thus, provided in the present disclosure are polymeric membranes with improved performance for use in natural gas separation applications. The membranes of the present disclosure allow a user to tailor the permeability, specificity, and durability of the membranes for their intended use in gas separation processes.

Definitions

Unless otherwise defined, all technical and scientific terms used in this document have the same meaning as commonly understood by one of ordinary skill in the art to which the present disclosure belongs. Methods and materials are described in this document for use in the present disclosure; other, suitable methods and materials known in the art can also be used. The materials, methods, and examples are illustrative only and not intended to be limiting. All publications, patent applications, patents, sequences, database entries, and other references mentioned in this document are incorporated by reference in their entirety. In case of conflict, the present specification, including definitions, will control.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (for example, 1%, 2%, 3%, and 4%) and the sub-ranges (for example, 0.1% to 0.5%, 1.1% to 2.2%, and 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

The term "about," as used in this disclosure, can allow for a degree of variability in a value or range, for example, within 10%, within 5%, or within 1% of a stated value or of a stated limit of a range.

As used in this disclosure, the terms "a," "an," and "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

In the methods described in this disclosure, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The terms "sour" or "sour gas" mean that the gas stream contains hydrogen sulfide ($H_2S$). The terms "sweet" or "sweet gas" mean that the gas contains little or no hydrogen sulfide ($H_2S$).

As used in the present disclosure, the term "monomer unit," used in reference to a polymer, refers to a monomer, or residue of a monomer, that has been incorporated into at least a portion of the polymer.

As used in the present disclosure, the term "polymerization product," used in reference to one or more monomers, refers to a polymer that can be formed by a chemical reaction of the one or more monomers. For example, a "polymerization product" of acrylic acid is a polymer containing acrylic acid monomer units.

As used in the present disclosure, the term "Cn-m alkyl" refers to any linear or branched saturated hydrocarbon group having n to m carbons. Alkyl groups include, but are not limited to, methyl, ethyl, propyl such as propan-1-yl, propan-2-yl (iso-propyl), butyl such as butan-1-yl, butan-2-yl (sec-butyl), 2-methyl-propan-1-yl (iso-butyl), 2-methyl-propan-2-yl (t-butyl), pentyl, hexyl, octyl, decyl, and the like. As used in the present disclosure, the term "alkylene" refers to a bivalent alkyl.

As used in the present disclosure, the term "halo" refers to —F, —Cl, —Br, or —I.

As used in the present disclosure, the term "hydroxyl" refers to —OH.

As used in the present disclosure, the term "amino" refers to $—NH_2$.

As used in the present disclosure, the term "thiol" refers to —SH.

As used in the present disclosure, the term "carboxyl" refers to —C(O)OH.

Where a variable of the present disclosure defines a group having more than one substituent (for example, group A of Formula I) and the Markush group definition for that variable lists, for example, a polycyclic aromatic hydrocarbon, then it is understood that the polycyclic aromatic hydrocarbon represents a substituent having the necessary valency.

Polymers and Membranes

The polymers of the present disclosure include copoly(1,2,4-triazole)s polymers. The backbone of the polymers includes one or more aromatic groups. In some embodiments, the copoly(1,2,4-triazole) polymer includes monomer units of Formula I and Formula II:

(I)

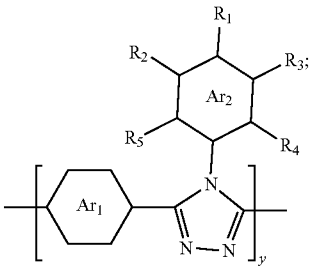

and (II)

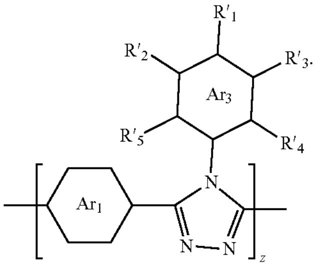

In Formula I, $Ar^1$ and $Ar^2$ are aromatic rings. In some embodiments, $Ar^1$ and $Ar^2$ are phenyl. In Formula I, $R^1$-$R^5$ are each independently selected from hydrogen, alkyl, hydroxyl, alkoxy, halogen, aromatic, and cyclic functional groups. In Formula II, $Ar^1$ and $Ar^3$ are aromatic rings. In some embodiments, $Ar^1$ and $Ar^3$ are phenyl. In Formula II, $R'^1$—$R'^5$ are each independently selected from hydrogen, alkyl, hydroxyl, alkoxy, halogen, aromatic, and cyclic functional groups. The ratio of y:z can vary between 1:10 and 10:1. For any segment of a polymer that includes a monomer unit of Formula I and a monomer unit of formula II, y and z represent the number of repetitive units in each segment and their corresponding ratio y:z varies between 1 and 9. For example, y=1 and z=9, y=2 and z=8, y=3 and z=7, y=4 and z=6, y=5 and z=5, y=6 and z=4, y=7 and z=3, y=8 and z=2, or y=9 and z=1.

In some embodiments, in a polymer that includes monomer units of Formula I and Formula II, at least one of $R^1$-$R^5$ and at least one of $R'^1$—$R'^5$ is not hydrogen, and at least one of $R^1$-$R^5$ is different from at least one of $R'^1$—$R'^5$. In some embodiments, in a polymer that includes monomer units of Formula I and Formula II, $R^1$ is hydroxyl and $R^2$-$R^5$ are each hydrogen. In some embodiments, in a polymer that includes monomer units of Formula I and Formula II, $R'^1$ is tert-butyl and $R'^2$—$R'^5$ are each hydrogen. In some embodiments, in a polymer that includes monomer units of Formula I and Formula II, $R'^2$ is methyl, $R'^3$ is methyl, and $R'^1$, $R'^4$, and $R'^5$ are each hydrogen. In some embodiments, in a polymer that includes monomer units of Formula I and Formula II, R'1 is fluoro, $R'^2$ is —$CF_3$, and $R'^3$—$R'^4$ are each hydrogen. In some embodiments, in a polymer that includes monomer units of Formula I and Formula II, $R^2$ is —$CH_2$—Br, $R^3$ is methyl, and $R^1$, $R^4$, and $R^5$ are each hydrogen. In some embodiments, $R^1$ is hydroxyl, $R^2$-$R^5$ are each hydrogen, $R'^1$ is tert-butyl, and $R'^2$—$R'^5$ are each hydrogen. In some embodiments, $R^1$ is hydroxyl, $R^2$-$R^5$ are each hydrogen, $R'^2$ and $R'^3$ are both methyl, and $R'^1$, $R'^4$, and $R'^5$ are each hydrogen. In some embodiments, $R^1$ is hydroxyl, $R^1$-$R^5$ are each hydrogen, $R'^1$ is —F, $R'^2$ is —$CF_3$, and $R'^3$—$R'^5$ are each hydrogen.

In some embodiments, in a polymer that includes monomer units of Formula I and Formula II, the polymer includes the monomer unit of Formula I and the monomer unit of Formula II in a molar ratio of about 10:1 to about 1:10. In some embodiments, in a polymer that includes monomer units of Formula I and Formula II, the polymer includes the monomer unit of Formula I and the monomer unit of Formula II in a molar ratio of about 2:1 to about 1:2. In some embodiments, in a polymer that includes monomer units of Formula I and Formula II, the polymer includes the monomer unit of Formula I and the monomer unit of Formula II in a molar ratio of about 1:1. In some embodiments, a polymer that includes monomer units of Formula I and Formula II has a number-average molecular weight of about 1,000 g/mol to about 1,000,000 g/mol. In some embodiments, a polymer that includes monomer units of Formula I and Formula II is covalently crosslinked.

In some embodiments, a membrane includes a polymer that includes monomer units of Formula I and Formula II. In some embodiments of the membrane, at least one of $R^1$-$R^5$ and at least one of $R'^1$—$R'^5$ is not hydrogen, and at least one of $R^1$-$R^5$ is different from at least one of $R'^1$—$R'^5$. In some embodiments of the membrane, $R^1$ is hydroxyl and $R^2$-$R^5$ are each hydrogen. In some embodiments of the membrane, $R'^1$ is tert-butyl and $R'^2$—$R'^5$ are each hydrogen. In some embodiments of the membrane, $R'^2$ is methyl, $R'^3$ is methyl, and $R'^1$, $R'^4$, and $R'^5$ are each hydrogen. In some embodiments of the membrane, $R'^1$ is fluoro, $R'^2$ is —$CF_3$, and $R'^3$—$R'^5$ are each hydrogen. In some embodiments of the membrane, $R^2$ is —$CH_2$—Br, $R^3$ is methyl, and $R^1$, $R^4$, and $R^5$ are each hydrogen. In some embodiments, $R^1$ is hydroxyl, $R^2$-$R^5$ are each hydrogen, $R'^1$ is tert-butyl, and $R'^2$—$R'^5$ are each hydrogen. In some embodiments, $R^1$ is hydroxyl, $R^2$-$R^5$ are each hydrogen, $R'^2$ and $R'^3$ are both methyl, and $R'^1$, $R'^4$, and $R'^5$ are each hydrogen. In some embodiments, $R^1$ is hydroxyl, $R^1$-$R^5$ are each hydrogen, $R'^1$ is —F, $R'^2$ is —$CF_3$, and $R'^3$—$R'^5$ are each hydrogen.

In some embodiments of the membrane, the polymer is covalently crosslinked. In some embodiments of the membrane, the membrane includes at least about 80% by weight of the polymer.

In some embodiments, a method for separating $CO_2$ and $H_2S$ from natural gas includes introducing a natural gas stream to the membrane and separating the $CO_2$ and $H_2S$ from the natural gas stream.

In some embodiments, the copoly(1,2,4-triazole)s described herein include repeats of Formula III, Formula IV, Formula V, and Formula VI:

(III)

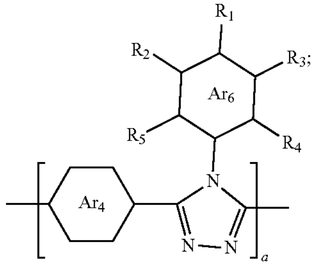

(IV)

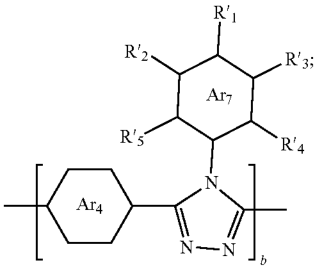

(V)

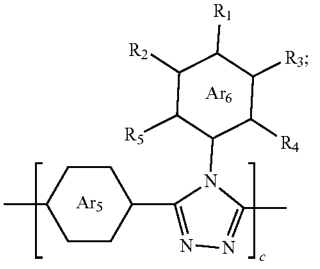

and (VI)

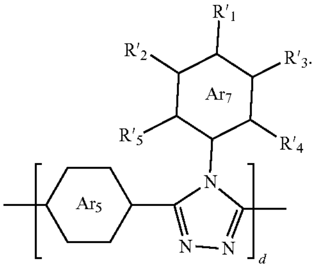

In Formula III, $Ar^4$ and $Ar^6$ are aromatic rings. In some embodiments, $Ar^4$ and $Ar^6$ are phenyl. In Formula III, $R^1$-$R^5$ are each independently selected from hydrogen, alkyl, hydroxyl, alkoxy, halogen, aromatic, and cyclic functional groups.

In Formula IV, $Ar^4$ and $Ar^7$ are aromatic rings. In some embodiments, $Ar^4$ and $Ar^7$ are phenyl. In Formula IV, $R'^1$—$R'^5$ are each independently selected from hydrogen, alkyl, hydroxyl, alkoxy, halogen, aromatic, and cyclic functional groups.

In Formula V, $Ar^5$ and $Ar^6$ are aromatic rings, and $R^1$-$R^5$ are each independently selected from hydrogen, alkyl, hydroxyl, alkoxy, halogen, aromatic, and cyclic functional groups.

In Formula VI, $Ar^5$ and $Ar^7$ are aromatic rings, and $R'^1$—$R'^5$ are each independently selected from hydrogen, alkyl, hydroxyl, alkoxy, halogen, aromatic, and cyclic functional groups. For any segment of a polymer that includes a monomer unit of Formula III, a monomer unit of Formula IV, a monomer unit of Formula V, and a monomer unit of Formula VI, a, b, c, and d represent the number of repetitive units in each segment and their corresponding ratio varies between 1 and 7, where a+b+c+d=10. For example, a=1 and (b+c+d)=9, a=2 and (b+c+d)=8, a=3 and (b+c+d)=7, a=4 and (b+c+d)=6, a=5 and (b+c+d)=5, a=6 and (b+c+d)=4, a=7 and (b+c+d)=3, b=1 and (a+c+d)=9, b=2 and (a+c+d)=8, b=3 and (a+c+d)=7, b=4 and (a+c+d)=6, b=5 and (a+c+d)=5, b=6 and (a+c+d)=4, b=7 and (a+c+d)=3, c=1 and (a+b+d)=9, c=2 and (a+b+d)=8, c=3 and (a+b+d)=7, c=4 and (a+b+d)=6, c=5 and (a+b+d)=5, c=6 and (a+b+d)=4, c=7 and (a+b+d)=3, d=1 and (a+b+c)=9, d=2 and (a+b+c)=8, d=3 and (a+b+c)=7, d=4 and (a+b+c)=6, d=5 and (a+b+c)=5, d=6 and (a+b+c)=4, and d=7 and (a+b+c)=3. For example, a=2, b=3, c=4, and d=1.

In some embodiments, in a polymer that includes monomer units of Formula III, IV, V and VI, at least one of $R^1$-$R^5$ and at least one of $R'^1$—$R'^5$ is not hydrogen, and at least one of $R^1$-$R^5$ is different from at least one of $R'^1$—$R'^5$. In some embodiments, in a polymer that includes monomer units of Formula III, IV, V, and VI, $R^1$ is hydroxyl and $R^2$-$R^5$ are each hydrogen. In some embodiments, in a polymer that includes monomer units of Formula III, IV, V, and V, $R'^1$ is tert-butyl and $R'^2$—$R'^5$ are each hydrogen. In some embodiments, in a polymer that includes monomer units of Formula III, IV, V, and VI, $R'^2$ is methyl, $R'^3$ is methyl, and $R'^1$, $R'^4$, and $R'^5$ are each hydrogen. In some embodiments, in a polymer that includes monomer units of Formula III, IV, V, and VI, $R'^1$ is fluoro, $R'^2$ is —$CF_3$, and $R'^3$—$R'^4$ are each hydrogen. In some embodiments, in a polymer that includes monomer units of Formula III, IV, V, and VI, $R^2$ is —$CH_2$—Br, $R^3$ is methyl, and $R^1$, $R^4$, and $R^5$ are each hydrogen. In some embodiments, $R^1$ is hydroxyl, $R^2$-$R^5$ are each hydrogen, $R'^1$ is tert-butyl, and $R'^2$—$R'^5$ are each hydrogen. In some embodiments, $R^1$ is hydroxyl, $R^2$-$R^5$ are each hydrogen, $R'^2$ and $R'^3$ are both methyl, and $R'^1$, $R'^4$, and $R'^5$ are each hydrogen. In some embodiments, $R^1$ is hydroxyl, $R^1$-$R^5$ are each hydrogen, $R'^1$ is —F, $R'^2$ is —$CF_3$, and $R'^3$—$R'^5$ are each hydrogen.

In some embodiments, a polymer that includes monomer units of Formula III, IV, V, and VI has a number-average molecular weight of about 1,000 g/mol to about 1,000,000 g/mol. In some embodiments, a polymer that includes monomer units of Formula III, IV, V, and VI is covalently crosslinked.

In some embodiments, a membrane includes a polymer that includes monomer units of Formula III, IV, V, and VI. In some embodiments of the membrane, at least one of $R^1$-$R^5$ and at least one of $R'^1$—$R'^5$ is not hydrogen, and at least one of $R^1$-$R^5$ is different from at least one of $R'^1$—$R'^5$. In some embodiments of the membrane, $R^1$ is hydroxyl and $R^2$-$R^5$ are each hydrogen. In some embodiments of the membrane, $R'^1$ is tert-butyl and $R'^2$—$R'^5$ are each hydrogen. In some embodiments of the membrane, $R'^2$ is methyl, $R'^3$ is methyl, and $R'^1$, $R'^4$, and $R'^5$ are each hydrogen. In some embodiments of the membrane, $R'^1$ is fluoro, $R'^2$ is —$CF_3$, and $R'^3$—$R'^5$ are each hydrogen. In some embodiments of the membrane, $R^2$ is —$CH_2$—Br, $R^3$ is methyl, and $R^1$, $R^4$, and $R^5$ are each hydrogen. In some embodiments, $R^1$ is hydroxyl, $R^2$-$R^5$ are each hydrogen, $R'^1$ is tert-butyl, and $R'^2$—$R'^5$ are each hydrogen. In some embodiments, $R^1$ is hydroxyl, $R^2$-$R^5$ are each hydrogen, $R'^2$ and $R'^3$ are both methyl, and $R'^1$, $R'^4$, and $R'^5$ are each hydrogen. In some embodiments, $R^1$ is hydroxyl, $R^1$-$R^5$ are each hydrogen, $R'^1$ is —F, $R'^2$ is —$CF_3$, and $R'^3$—$R'^5$ are each hydrogen.

In some embodiments of the membrane, the polymer is covalently crosslinked. In some embodiments of the membrane, the membrane includes at least about 80% by weight of the polymer.

In some embodiments, a method for separating $CO_2$ and $H_2S$ from natural gas includes introducing a natural gas stream to the membrane and separating the $CO_2$ and $H_2S$ from the natural gas stream.

In some embodiments, the backbone of the copoly(1,2,4-triazole)s described in this disclosure can include multiple aromatic groups and/or fluorinated functional groups. The copoly(1,2,4-triazole)s can include repeats of Formula VII and Formula VIII:

(VII)

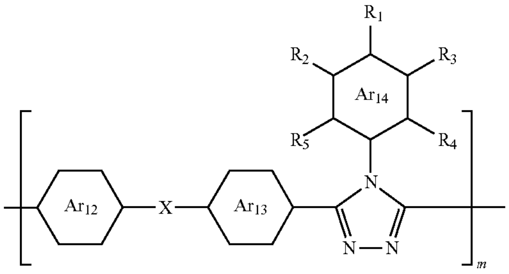

; and (VIII)

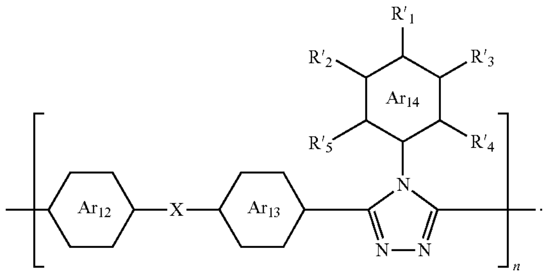

In Formula VII, $Ar^{12}$, $Ar^{13}$, and $Ar^{14}$ are aromatic rings. In some embodiments, $Ar^{12}$, $Ar^{13}$, and $Ar^{14}$ are phenyl. In Formula VII, $R^1$-$R^5$ are each independently selected from hydrogen, alkyl, hydroxyl, alkoxy, halogen, aromatic, and cyclic functional groups. In some embodiments, X is —$CH_2$—, —CHR—, —$CR_2$—, —$CR_1R_2$—, an aromatic ring, or an aliphatic ring, where each R is independently selected from hydrogen, alkyl, hydroxyl, alkoxy, halogen, aromatic, and cyclic functional groups. In some embodiments, X is absent. In some embodiments, X is —CYZ—, where Y and Z are selected from any element, group of elements, cation, anion, and neutral species. In some embodiments, X is —$C(CF_3)_2$.

In Formula VIII, $Ar^{12}$, $Ar^{13}$, and $Ar^{14}$ are aromatic rings. In some embodiments, $Ar^{12}$, $Ar^{13}$, and $Ar^{14}$ are phenyl. In Formula VIII, and $R'^1$—$R'^5$ are each independently selected from hydrogen, alkyl, hydroxyl, alkoxy, halogen, aromatic, and cyclic functional groups. The ratio of m:n can vary between 1:10 and 10:1. For any segment of a polymer that includes a monomer unit of Formula VII and a monomer unit of Formula VIII, m and n represent the number of repetitive units in each segment and their corresponding ratio m:n varies between 1 and 9. For example, m=1 and n=9, m=2 and n=8, m=3 and n=7, m=4 and n=6, m=5 and n=5, m=6 and n=4, m=7 and n=3, m=8 and n=2, or m=9 and n=1.

In some embodiments, in a polymer that includes monomer units of Formula VII and Formula VIII, at least one of $R^1$-$R^5$ and at least one of $R'^1$—$R'^5$ is not hydrogen, and at least one of $R^1$-$R^5$ is different from at least one of $R'^1$—$R'^5$. In some embodiments, in a polymer that includes monomer units of Formula VII and Formula VIII, $R^1$ is hydroxyl and $R^2$-$R^5$ are each hydrogen. In some embodiments, in a polymer that includes monomer units of Formula VII and Formula VIII, $R'^1$ is tert-butyl and $R'^2$—$R'^5$ are each hydrogen. In some embodiments, in a polymer that includes monomer units of Formula VII and Formula VIII, $R'^2$ is methyl, $R'^3$ is methyl, and $R'^1$, $R'^4$, and $R'^5$ are each hydrogen. In some embodiments, in a polymer that includes monomer units of Formula VII and Formula VIII, $R'^1$ is fluoro, $R'^2$ is —$CF_3$, and $R'^3$—$R'^4$ are each hydrogen. In some embodiments, in a polymer that includes monomer units of Formula VII and Formula VIII, $R^2$ is —$CH_2$—Br, $R^3$ is methyl, and $R^1$, $R^4$, and $R^5$ are each hydrogen. In some embodiments, $R^1$ is hydroxyl, $R^2$-$R^5$ are each hydrogen, $R'^1$ is tert-butyl, and $R'^2$—$R'^5$ are each hydrogen. In some embodiments, $R^1$ is hydroxyl, $R^2$-$R^5$ are each hydrogen, $R'^2$ and $R'^3$ are both methyl, and $R'^1$, $R'^4$, and $R'^5$ are each hydrogen. In some embodiments, $R^1$ is hydroxyl, $R^1$-$R^5$ are each hydrogen, $R'^1$ is —F, $R'^2$ is —$CF_3$, and $R'^3$—$R'^5$ are each hydrogen.

In some embodiments, in a polymer that includes monomer units of Formula VII and Formula VIII, the polymer includes the monomer unit of Formula VII and the monomer unit of Formula VIII in a molar ratio of about 10:1 to about 1:10. In some embodiments, in a polymer that includes monomer units of Formula VII and Formula VIII, the polymer includes the monomer unit of Formula VII and the monomer unit of Formula VIII in a molar ratio of about 2:1 to about 1:2. In some embodiments, in a polymer that includes monomer units of Formula VII and Formula VIII, the polymer includes the monomer unit of Formula VII and the monomer unit of Formula VIII in a molar ratio of about 1:1. In some embodiments, a polymer that includes monomer units of Formula VII and Formula VIII has a number-average molecular weight of about 1,000 g/mol to about 1,000,000 g/mol. In some embodiments, a polymer that includes monomer units of Formula VII and Formula VIII is covalently crosslinked. In some embodiments, a membrane includes a polymer that includes monomer units of Formula VII and Formula VIII. In some embodiments of the membrane, at least one of $R^1$-$R^5$ and at least one of $R'^1$—$R'^5$ is not hydrogen, and at least one of $R^1$-$R^5$ is different from at least one of $R'^1$—$R'^5$. In some embodiments of the membrane, $R^1$ is hydroxyl and $R^2$-$R^5$ are each hydrogen. In some embodiments of the membrane, $R'^1$ is tert-butyl and $R'^2$—$R'^5$ are each hydrogen. In some embodiments of the membrane, $R'^2$ is methyl, $R'^3$ is methyl, and $R'^1$, $R'^4$, and $R'^5$ are each hydrogen. In some embodiments of the membrane, $R'^1$ is fluoro, $R'^2$ is —$CF_3$, and $R'^3$—$R'^5$ are each hydrogen. In some embodiments of the membrane, $R^2$ is —$CH_2$—Br, $R^3$ is methyl, and $R^1$, $R^4$, and $R^5$ are each hydrogen. In some embodiments, $R^1$ is hydroxyl, $R^2$-$R^5$ are each hydrogen, $R'^1$ is tert-butyl, and $R'^2$—$R'^5$ are each hydrogen. In some embodiments, $R^1$ is hydroxyl, $R^2$-$R^5$ are each hydrogen, $R'^2$ and $R'^3$ are both methyl, and $R'^1$, $R'^4$, and $R'^5$ are each hydrogen. In some embodiments, $R^1$ is hydroxyl, $R^1$-$R^5$ are each hydrogen, $R'^1$ is —F, $R'^2$ is —$CF_3$, and $R'^3$—$R'^5$ are each hydrogen.

In some embodiments of the membrane, the polymer is covalently crosslinked. In some embodiments of the membrane, the membrane includes at least about 80% by weight of the polymer.

In some embodiments, a method for separating $CO_2$ and $H_2S$ from natural gas includes introducing a natural gas stream to the membrane and separating the $CO_2$ and $H_2S$ from the natural gas stream.

In some embodiments, the copoly(1,2,4-triazole)s described in this disclosure include repeats of Formula VIIa and VIIIa:

(VIIa)

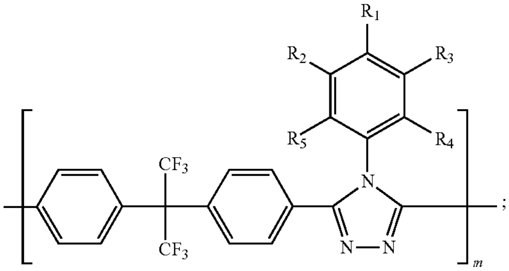

; and (VIIIa)

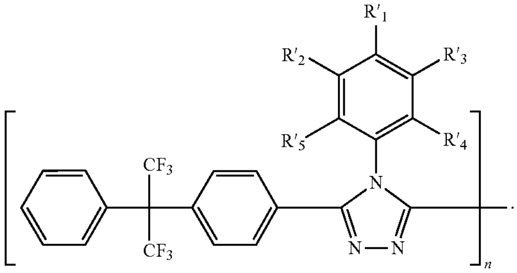

.

In Formula VIIa, $R^1$-$R^5$ are each independently selected from hydrogen, alkyl, hydroxyl, alkoxy, halogen, aromatic, and cyclic functional groups.

In Formula VIIIa, $R'^1$—$R'^5$ are each independently selected from hydrogen, alkyl, hydroxyl, alkoxy, halogen, aromatic, and cyclic functional groups. The ratio of m:n can vary between 1:10 and 10:1. For any segment of a polymer that includes a monomer unit of Formula VIIa and a monomer unit of Formula VIIIa, m and n represent the number of repetitive units in each segment and their corresponding ratio m:n varies between 1 and 9. For example, m=1 and n=9, m=2 and n=8, m=3 and n=7, m=4 and n=6, m=5 and n=5, m=6 and n=4, m=7 and n=3, m=8 and n=2, or m=9 and n=1.

In some embodiments, in a polymer that includes monomer units of Formula VIIa and Formula VIIIa, at least one of $R^1$-$R^5$ and at least one of $R'^1$—$R'^5$ is not hydrogen, and at least one of $R^1$-$R^5$ is different from at least one of $R'^1$—$R'^5$. In some embodiments, in a polymer that includes monomer units of Formula VIIa and Formula VIIIa, $R^1$ is hydroxyl and $R^2$-$R^5$ are each hydrogen. In some embodiments, in a polymer that includes monomer units of Formula VIIa and Formula VIIIa, $R'^1$ is tert-butyl and $R'^2$—$R'^5$ are each hydrogen. In some embodiments, in a polymer that includes monomer units of Formula VIIa and Formula VIIIa, $R'^2$ is methyl, $R'^3$ is methyl, and $R'^1$, $R'^4$, and $R'^5$ are each hydrogen. In some embodiments, in a polymer that includes monomer units of Formula VIIa and Formula VIIIa, $R'^1$ is fluoro, $R'^2$ is —$CF_3$, and $R'^3$—$R'^4$ are each hydrogen. In some embodiments, in a polymer that includes monomer units of Formula VIIa and Formula VIIIa, $R^2$ is —$CH_2$—Br, $R^3$ is methyl, and $R^1$, $R^4$, and $R^5$ are each hydrogen. In some embodiments, $R^1$ is hydroxyl, $R^2$-$R^5$ are each hydrogen, $R'^1$ is tert-butyl, and $R'^2$—$R'^5$ are each hydrogen. In some embodiments, $R^1$ is hydroxyl, $R^2$-$R^5$ are each hydrogen, $R'^2$ and $R'^3$ are both methyl, and $R'^1$, $R'^4$, and $R'^5$ are each hydrogen. In some embodiments, $R^1$ is hydroxyl, $R^1$-$R^5$ are each hydrogen, $R'^1$ is —F, $R'^2$ is —$CF_3$, and $R'^3$—$R'^5$ are each hydrogen.

In some embodiments, in a polymer that includes monomer units of Formula VIIa and Formula VIIIa, the polymer includes the monomer unit of Formula VIIa and the monomer unit of Formula VIIIa in a molar ratio of about 10:1 to about 1:10. In some embodiments, in a polymer that includes monomer units of Formula VIIa and Formula VIIIa, the polymer includes the monomer unit of Formula VIIa and the monomer unit of Formula VIIIa in a molar ratio of about 2:1 to about 1:2. In some embodiments, in a polymer that includes monomer units of Formula VIIa and Formula VIIIa, the polymer includes the monomer unit of Formula VIIa and the monomer unit of Formula VIIIa in a molar ratio of about 1:1. In some embodiments, a polymer that includes monomer units of Formula VIIa and Formula VIIIa has a number-average molecular weight of about 1,000 g/mol to about 1,000,000 g/mol. In some embodiments, a polymer that includes monomer units of Formula VIIa and Formula VIIIa is covalently crosslinked.

In some embodiments, a membrane includes a polymer that includes monomer units of Formula VIIa and Formula VIIIa. In some embodiments of the membrane, at least one of $R^1$-$R^5$ and at least one of $R'^1$—$R'^5$ is not hydrogen, and at least one of $R^1$-$R^5$ is different from at least one of $R'^1$—$R'^5$. In some embodiments of the membrane, $R^1$ is hydroxyl and $R^2$-$R^5$ are each hydrogen. In some embodiments of the membrane, $R'^1$ is tert-butyl and $R'^2$—$R'^5$ are each hydrogen. In some embodiments of the membrane, $R'^2$ is methyl, $R'^3$ is methyl, and $R'^1$, $R'^4$, and $R'^5$ are each hydrogen. In some embodiments of the membrane, $R'^1$ is fluoro, $R'^2$ is —$CF_3$, and $R'^3$—$R'^5$ are each hydrogen. In some embodiments of the membrane, $R^2$ is —$CH_2$—Br, $R^3$ is methyl, and $R^1$, $R^4$, and $R^5$ are each hydrogen. In some embodiments, $R^1$ is hydroxyl, $R^2$-$R^5$ are each hydrogen, $R'^1$ is tert-butyl, and $R'^2$—$R'^5$ are each hydrogen. In some embodiments, $R^1$ is hydroxyl, $R^2$-$R^5$ are each hydrogen, $R'^2$ and $R'^3$ are both methyl, and $R'^1$, $R'^4$, and $R'^5$ are each hydrogen. In some embodiments, $R^1$ is hydroxyl, $R^1$-$R^5$ are each hydrogen, $R'^1$ is —F, $R'^2$ is —$CF_3$, and $R'^3$—$R'^5$ are each hydrogen.

In some embodiments of the membrane, the polymer is covalently crosslinked. In some embodiments of the membrane, the membrane includes at least about 80% by weight of the polymer.

In some embodiments, a method for separating $CO_2$ and $H_2S$ from natural gas includes introducing a natural gas stream to the membrane and separating the $CO_2$ and $H_2S$ from the natural gas stream.

In some embodiments, polymer that includes any of the monomers of Formula I-Formula VIII, Formula VIIa, or Formula VIIIa as described herein has a number-average molecular weight of about 1,000 g/mol to about 1,000,000 g/mol, such as about 1,000 g/mol to about 900,000 g/mol, about 10,000 g/mol to about 800,000 g/mol, about 50,000 g/mol to about 700,000 g/mol, about 100,000 g/mol to about 600,000 g/mol, about 200,000 g/mol to about 500,000 g/mol, about 300,000 g/mol, or about 1,000 g/mol, about 5,000 g/mol, about 10,000 g/mol, about 25,000 g/mol, about 50,000 g/mol, about 100,000 g/mol, about 150,000 g/mol, about 200,000 g/mol, about 250,000 g/mol, about 300,000 g/mol, about 350,000 g/mol, about 400,000 g/mol, about 450,000 g/mol, about 500,000 g/mol, about 550,000 g/mol, about 600,000 g/mol, about 650,000 g/mol, about 700,000 g/mol, about 750,000 g/mol, about 800,000 g/mol, about 850,000 g/mol, about 900,000 g/mol, about 950,000 g/mol, or about 1,000,000 g/mol. In some embodiments, the polymers are synthesized via polycondensation followed by a nucleophilic substitution reaction.

A general synthetic scheme to prepare a copoly(1,2,4-triazole)s polymer of the present disclosure that includes repeats of Formula I and Formula II is shown Scheme 1.

Scheme 1

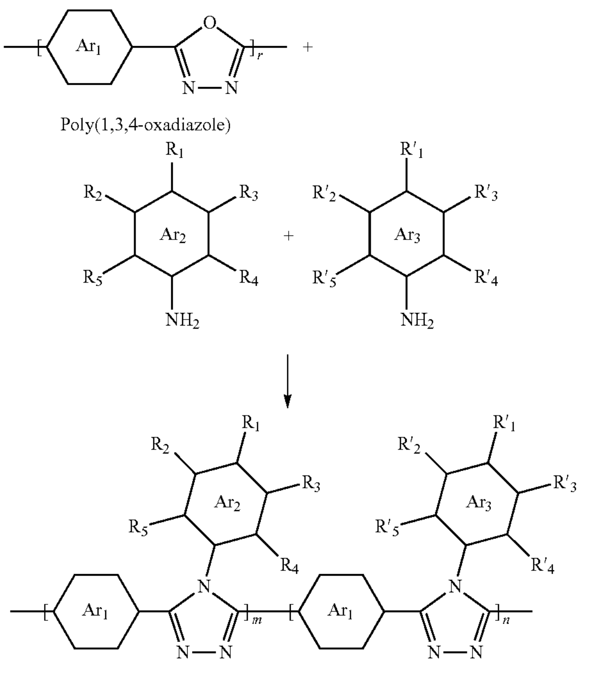

Poly(1,3,4-oxadiazole)

Copoly(1,2,4-triazole)

In Scheme 1, a poly(1,3,4-oxiazole) including an aromatic ring $Ar^1$ is reacted with two or more different aniline derivatives that include aromatic rings $Ar^2$ and $Ar^3$. $Ar^1$, $Ar^2$, and $Ar^3$ are aromatic rings, and each of $R^1$-$R^5$ and $R'^1$—$R^5$ is an independently selected functional group, selected from hydrogen, alkyl, hydroxyl, alkoxy, halogen, aromatic and cyclic functional groups. Aromatic rings $Ar^1$, $Ar^2$, and $Ar^3$ can each be phenyl. In some embodiments, the aniline derivatives can be selected from the group of aniline derivatives as shown in FIG. 1. For the copoly(1,2,4-triazole) shown in Scheme 1, the ratio of m:n can vary between 1:10 and 10:1. For any segment of the polymer including the monomer units, m and n represent the number of repetitive units in each segment and their corresponding ratio m:n varies between 1 and 9. For example, m=1 and n=9, m=2 and n=8, m=3 and n=7, m=4 and n=6, m=5 and n=5, m=6 and n=4, m=7 and n=3, m=8 and n=2, m=9 and n=1. The molecular weight of the copoly(1,2,4-triazole) shown in Scheme 1 can range from 1,000 g/mol to 1,000,000 g/mol. In some embodiments, the molecular weight of the copoly (1,2,4-triazole) shown in Scheme 1 can range from 10,000 g/mol to 100,000 g/mol.

In some embodiments, the copoly(1,2,4-triazole)s are prepared from copoly(1,3,4-oxadizoles)s according to the general procedure shown in Scheme 2. Scheme 2 allows for variation in the backbone of the polymer, for example, variation in the aromatic rings $Ar^1$ and $Ar^2$.

Scheme 2

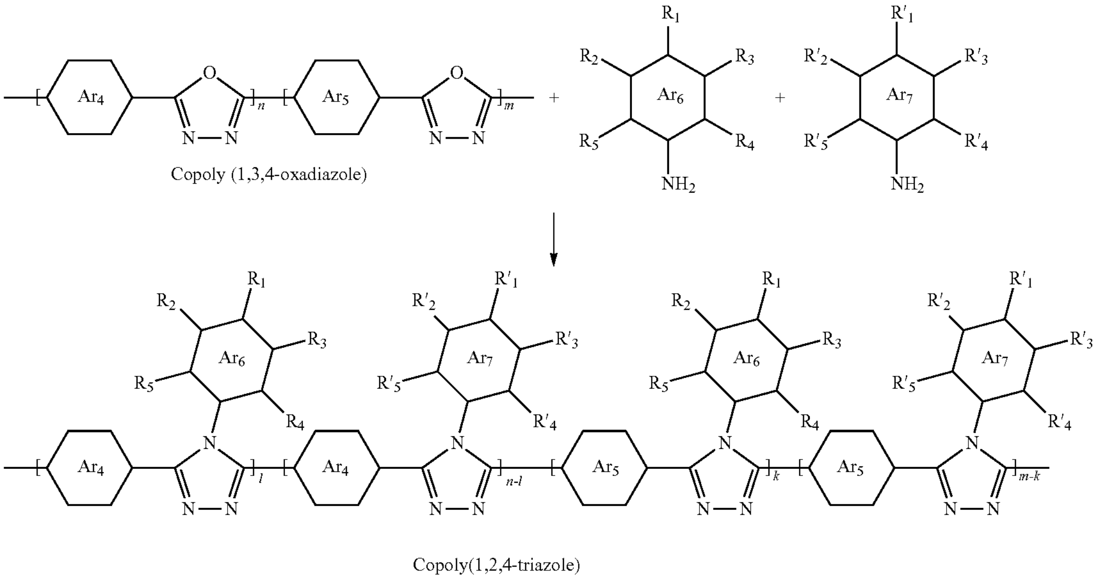

Scheme 2 illustrates the formation of a copoly(1,2,4-triazole) with more than one type of aromatic ring in the backbone of the polymer. Scheme 2 illustrates variation in the polymer backbone as well as in the triazole functionalization. In Scheme 2, a copoly(1,3,4-oxadiazole) is reacted with two or more different aniline derivatives that include aromatic rings $Ar^4$, $Ar^5$, $Ar^6$, and $Ar^7$. In Scheme 2, $Ar^4$, $Ar^5$, $Ar^6$, and $A^7$ are aromatic rings, and each of $R^1$-$R^5$ and $R'^1$—$R^5$ is an independently selected functional group. Aromatic rings $Ar^4$, $Ar^5$, $Ar^6$, and $Ar^7$ can each be phenyl. Each $R^1$-$R^5$ and $R'^1$—$R'^5$ is independently selected from hydrogen, alkyl, hydroxyl, alkoxy, halogen, aromatic, and cyclic functional groups. In some embodiments, the aniline derivatives can be selected from the group of aniline derivatives shown in FIG. 1. In some embodiments, different types of copoly(1,2,4-triazole)s are prepared by varying the molar ratio of the aromatic substituents onto the 1,2,4-triazole rings and/or the aromatic rings in the backbone of the copoly(1,2,4-triazole)s.

For the copoly(1,3,4-oxadizole) precursor shown in Scheme 2, l, m and n represent the number of repetitive units in each segment and their corresponding ratio m:n varies between 1 and 9. For example, m=1 and n=9, m=2 and n=8, m=3 and n=7, m=4 and n=6, m=5 and n=5, m=6 and n=4, m=7 and n=3, m=8 and n=2, or m=9 and n=1. For the copoly(1,2,4-triazole) product shown in Scheme 2, each of m, n, and k can vary from 1 to 9. The molecular weight of the copoly(1,2,4-triazole) shown in Scheme 2 can range from 1,000 g/mol to 1,000,000 gm/mol. In some embodiments, the molecular weight of the copoly(1,2,4-triazole) shown in Scheme 2 can range from 10,000 g/mol to 100,000 g/mol.

In some embodiments, the functionalized copoly(1,2,4-triazole)s polymers are formed into membranes. In some embodiments, the membranes are formed by filtering and heating a solution that includes the polymers described in this disclosure.

In some embodiments, the plasticization resistance of the polymeric membranes is increased by creating networks of polymeric chains within a membrane matrix through chemical or thermal crosslinking. The increased plasticization can be useful during high-pressure sweet or sour mixed-gas separation. The functional groups present on the aniline derivatives can be selected to allow a crosslinking or chemical reaction to occur, whether under chemical conditions or thermal conditions.

In some embodiments, the copoly(1,2,4-triazole)s of the present disclosure include hydroxyl groups. In these copoly (1,2,4-triazole)s, the hydroxyl groups increase the physical interactions between polymeric chains, for example through the formation of hydrogen bonds or dipole-dipole type interactions between the polymeric chains. This limits the mobility of the copoly(1,2,4-triazole)s under harsh separation conditions of temperature and pressure. In addition, the hydroxyl groups allow two adjacent phenol groups to react to form a covalent bond under high temperature, for example, a temperature greater that 180° C. This crosslinking reaction is referred to herein as thermal self-crosslinking. An example of thermal self-crosslinking is shown in Scheme 3. Thermal self-crosslinking can improve the permeation properties and plasticization resistance of the polymeric membranes during mixed-gas separation at high feed pressures.

Scheme 3

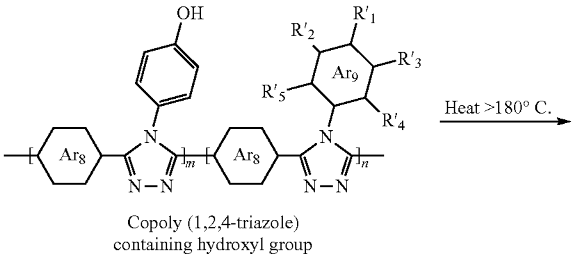

-continued

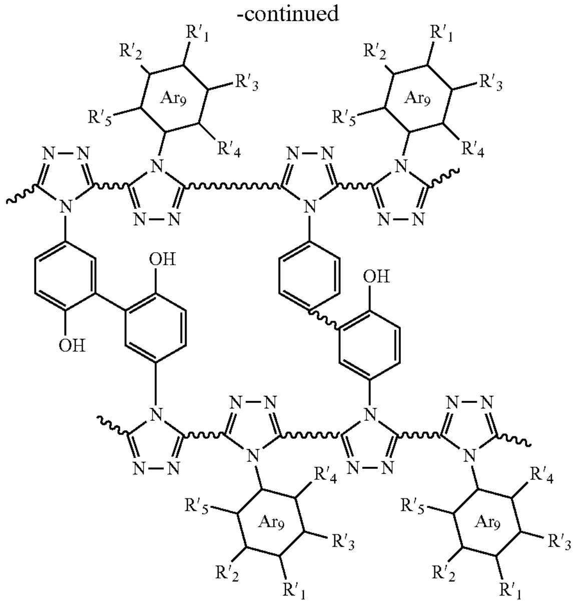

Crosslinked copoly (1,2,4-triazole) network

Scheme 3 illustrates an embodiment of the polymers described in this disclosure, where the polymer includes a hydroxyl group. In some embodiments, the hydroxyl group is used to crosslink the polymer under high temperature, for example temperatures greater than 180° C. In Scheme 3, $Ar^8$ and $Ar^9$ are aromatic rings, and each $R'_x$ is an independently selected functional group, for example, hydrogen, alkyl, hydroxyl, alkoxy, halogen, aromatic, or a cyclic functional group. Aromatic rings $Ar^8$, and $Ar^9$ can each be phenyl. In some embodiments, the $Ar^9$ functional group is derived from the aniline derivatives shown in FIG. 1. For the copoly(1,2,4-triazole) shown in Scheme 3, the ratio of m:n can vary between 1:10 and 10:1. For any segment of the polymer including the monomer units, m and n represent the number of repetitive units in each segment and their corresponding ratio m:n varies between 1 and 9. For example, m=1 and n=9, m=2 and n=8, m=3 and n=7, m=4 and n=6, m=5 and n=5, m=6 and n=4, m=7 and n=3, m=8 and n=2, or m=9 and n=1. The molecular weight of the copoly(1,2,4-triazole) shown in Scheme 3 can range from 1,000 g/mol to 1,000,000 g/mol. In some embodiments, the molecular weight of the copoly(1,2,4-triazole) shown in Scheme 3 can range from 10,000 g/mol to 100,000 g/mol.

Crosslinking and thermal self-crosslinking is not limited to hydroxyl groups. Functional groups that can form a covalent bond under thermal treatment include, for example, a carboxylic acid group (—COOH) or an alkyl halide group ($—CH_2—X$, —CHR—X, or $CR_2—X$, where X is F, Cl, Br or I). An embodiment of a thermal self-crosslinking copoly (1,2,4-triazole) with an alkyl halide group is shown in Scheme 4.

Scheme 4

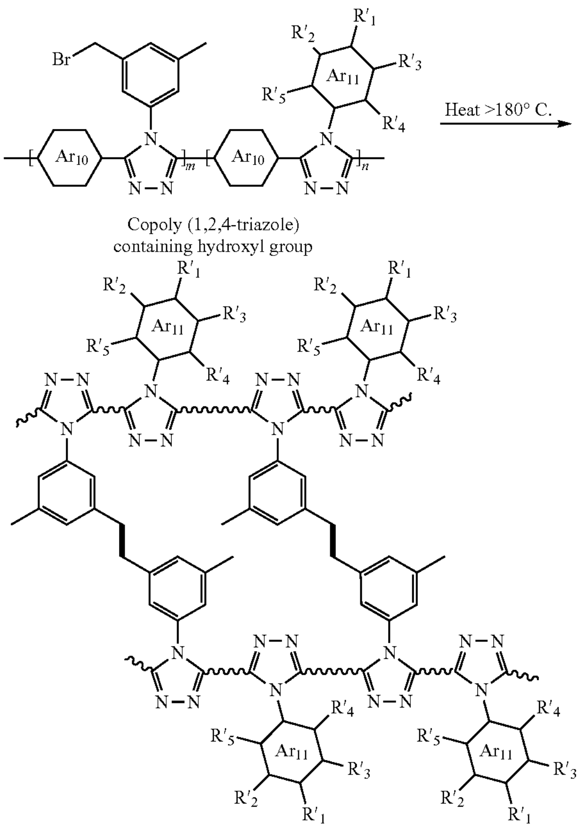

Copoly (1,2,4-triazole) containing hydroxyl group

Crosslinked copoly(1,2,4-triazole)network

In Scheme 4, a copoly(1,2,4-triazole) that includes a benzylic bromine was obtained through the bromination of methyl substituents within the polymer backbone. The resulting polymer can crosslink at high temperatures. In more detail, under high thermal treatment, the carbon-bromine bond is broken (debromination) to generate free radicals at the benzylic position, which can react with a similar site created the same way on a different polymeric chain to form an interchain covalent bond (ethylene crosslinks, Scheme 4). The formation of the ethylene crosslinks results in a copoly(1,2,4-triazole) crosslinked network.

In Scheme 4, $Ar^{10}$ and $Ar^{11}$ are aromatic rings, and each $R'_x$ is an independently selected functional group, for example, hydrogen, alkyl, hydroxyl, alkoxy, halogen, aromatic, or a cyclic functional group. In some embodiments, $Ar^{10}$ and $Ar^{11}$ are each phenyl. In some embodiments, the $Ar^{11}$ functional group is derived from the aniline derivatives shown in FIG. 1. For the copoly(1,2,4-triazole) shown in Scheme 4, the ratio of m:n can vary between 1:10 and 10:1. For any segment of the polymer including the monomer units, m and n represent the number of repetitive units in each segment and their corresponding ratio m:n varies between 1 and 9. For example, m=1 and n=9, m=2 and n=8, m=3 and n=7, m=4 and n=6, m=5 and n=5, m=6 and n=4, m=7 and n=3, m=8 and n=2, or m=9 and n=1. The molecular weight of the copoly(1,2,4-triazole) shown in Scheme 3 can range from 1,000 g/mol to 1,000,000 g/mol. In some embodiments, the molecular weight of the copoly(1,2,4-triazole) shown in Scheme 3 can range from 10,000 g/mol to 100,000 g/mol.

In some embodiments, the polymer backbone can include fluorinated functional groups. The presence of fluorinated functional groups, for example a hexafluoropropyl moiety [—$C(CF_3)_2$—], increases a polymer's solubility and disrupts the chain packing within the membrane matrix, which leads to improving its gas permeation properties.

Figure 2:
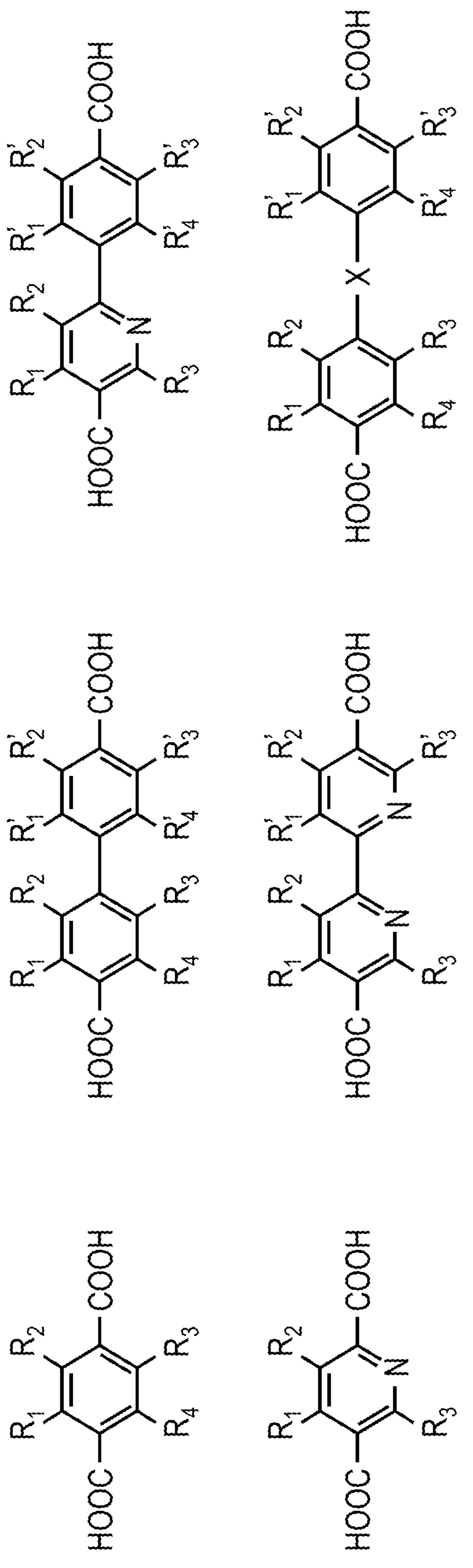
FIG. 2 shows examples of diacids that can be used to generate copoly(1,2,4-triazole)s.

Scheme 5 shows an example of incorporating fluorinated functional groups into the polymer backbone.

groups. In FIG. 2, X is —$CH_2$—, —CHR—, —$CR_2$—, —$CR_1R_2$—, an aromatic ring, or an aliphatic ring, where each R is independently selected from hydrogen, alkyl, hydroxyl, alkoxy, halogen, aromatic, and cyclic functional groups. In some embodiments, X is absent. In some embodiments, X is —CYZ—, where Y and Z are selected from any element, group of elements, cation, anion, and neutral species.

Scheme 5

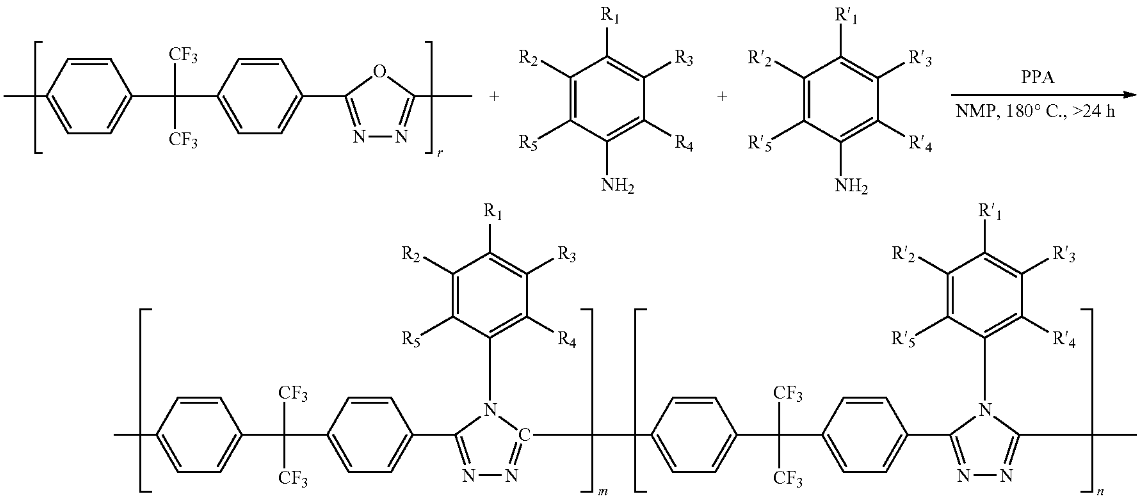

In Scheme 5, an embodiment of a fluorinated copoly(1,2,4-triazole) is prepared by reacting a fluorinated poly(1,3,4-oxadizole) polymer (POz-$CF_3$) with two or more aniline derivatives. Each $R_x$ and $R'_x$ is an independently selected functional group selected from hydrogen, alkyl, hydroxyl, alkoxy, halogen, aromatic and cyclic functional groups. In some embodiments, the resulting polymer includes functional groups that can form a covalent bond under thermal treatment, i.e., the resulting polymer can be thermally crosslinked. For example, in some embodiments, at least one of $R_x$ or $R'_x$ is hydroxyl, and the resulting polymer is thermally crosslinked. In some embodiments, at least one of $R_x$ or $R'_x$ is a carboxylic acid group (—COOH) or an alkyl halide group (—$CH_2$—X, —CHR—X, or $CR_2$—X, where X is F, Cl, Br or I).

For the copoly(1,2,4-triazole) shown in Scheme 4, the ratio of m:n can vary between 1:10 and 10:1. For any segment of the polymer including the monomer units, m and n represent the number of repetitive units in each segment and their corresponding ratio m:n varies between 1 and 9. For example, m=1 and n=9, m=2 and n=8, m=3 and n=7, m=4 and n=6, m=5 and n=5, m=6 and n=4, m=7 and n=3, m=8 and n=2, or m=9 and n=1.

In some embodiments, the fluorinated poly(1,3,4-oxadizole) reactant in Scheme 5 is prepared by reacting a 4,4'-(perfluoropropane-2,2-diyl)dibenzoic acid with hydrazine sulfate. However, this synthetic scheme is not limited to polymer reactants prepared with a single type of diacid. In some embodiments, more than one diacid is used to create a polymer backbone that includes more than one repeating unit. FIG. 2 shows examples of diacids that can be used to generate copoly(1,2,4-triazole)s. In FIG. 2, each $R^1$-$R^4$ and $R'^1$—$R'^4$ is independently selected from hydrogen, alkyl, hydroxyl, alkoxy, halogen, aromatic, and cyclic functional In some embodiments, the polymers described herein are used to make membranes. Membranes can be prepared from the polymers using a number of suitable methods. For example, the membranes can be formed by a solution casting method, where a polymer solution is heated in a vessel to create a membrane. In some embodiments, membrane formation includes crosslinking. In some embodiments, the membrane includes at least about 80 wt % of the polymer. For example, in some embodiments, the membrane includes at least about 85 wt %, at least about 90 wt %, at least about 95 wt %, at least about 97.5 wt %, at least about 98 wt %, at least about 98.5 wt %, or at least about 99 wt % of the polymer.

The prepared membranes can be used in gas separation processes. The gas separation processes can include methods of separating components from a sweet or a sour feed gas. The gas separation processes can include methods of separating He, $N_2$, $CH_4$, $CO_2$, $H_2S$, or combinations thereof from a feed gas.

EXAMPLES

Example 1: Preparation of Fluorinated Poly(1,3,4-Oxadiazole) Polymer (POz-$CF_3$)

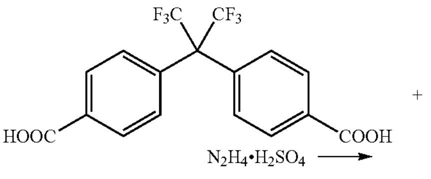

-continued

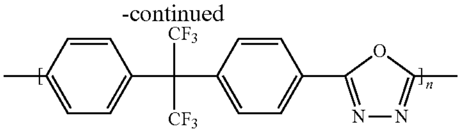

In a 250-mL three-neck round bottom flask equipped with a nitrogen inlet and a mechanical stirrer, polyphosphoric acid (PPA, 29.1 mL) (60.0 g; d=2.06 g/mL; weight ratio PPA/hydrazine sulfate=15) was introduced to the reaction vessel and heated to 100° C. with vigorous stirring for one hour. Hydrazine sulfate (3.98 g, 30.6 mmol) was then added to the reaction vessel and the mixture was heated to 160° C. until complete dissolution of the solid added. Next, 4,4'-(perfluoropropane-2,2-diyl)dibenzoic acid (10.0 g, 25.5 mmol) was added and the reaction mixture was stirred for additional 3 hours at the same temperature. The resulting viscous polymer was precipitated in a 1M NaOH aqueous solution. The solid polymer was then transferred to deionized water and the mixture was further stirred at 80° C. overnight. The polymer was then collected through filtration and dried in a vacuum oven at 100° C. for 24 hours. The final polymer POz-$CF_3$ (9.25 g, 23.11 mmol, 91% yield) was then obtained as white-off fibrous solid. $^{1}$H NMR analysis (500 MHz, Chloroform-d) yielded peaks at δ 8.19 (d, J=8.2 Hz, 4H), 7.61 (d, J=7.8 Hz, 4H). The POz-$CF_3$ polymer can have a molecular weight from 1,000 g/mol to 1,000,000 g/mol. In some embodiments, the molecular weight of the POz-$CF_3$ polymer is from 10,000 g/mol to 100,000 g/mol.

Example 2: Preparation of the Fluorinated Copoly (1,2,4-Triazole): FPT-pH(OH)/pH(t-Bu) (1:1)

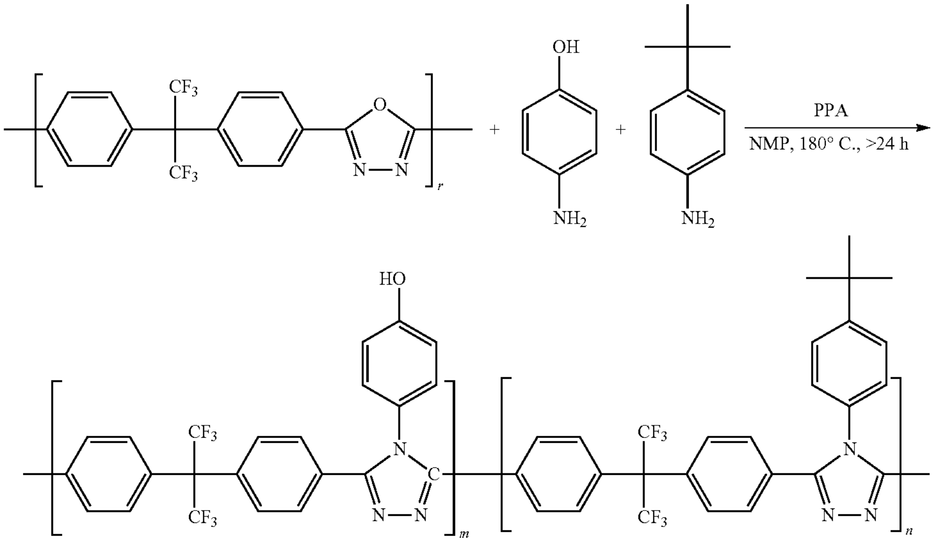

In a 100-mL three-neck round bottom flask equipped with a nitrogen inlet and a mechanical stirrer, poly(1,3,4-oxadiazole) (POz-$CF_3$) (1.000 g, 2.498 mmol, 1.0 eq.), 4-aminophenol (0.164 g, 1.499 mmol, 0.6 eq.), and 4-(tert-butyl) aniline (0.224 g, 1.499 mmol, 0.6 eq.) were introduced, followed by 10 mL of N-methyl-2-pyrrolidone (NMP) and polyphosphoric acid (PPA; 0.154 mL; 1.0 g; d=2.06 g/mL; used as a catalyst). The mixture was heated at 180° C. for 9 hours. The reaction progress was monitored by $^{1}$H-NMR. If needed, another portion of 4-aminophenol (0.164 g, 1.499 mmol, 0.6 eq.) and 4-(tert-butyl)aniline (0.224 g, 1.499 mmol, 0.6 eq.) were added and the reaction mixture was further stirred for another 9 hours at 180° C. To ensure all the poly(1,3,4-oxadiazole) was converted into poly(1,2,4-triazole), 0.10 mL of 4-(tert-butyl)aniline was added and the reaction mixture was further stirred for another 9 hours at 180° C. The resulting viscous polymer was precipitated in water. The solid polymer was collected and 100 mL of methanol was added, and the mixture was further stirred overnight. The polymer was then collected through filtration and dried in an oven preheated to 70° C. for 24 hours. The final polymer FPT-Ph(OH)/Ph(t-Bu) (1:1) (1.191 g, 1.199 mmol, 96% yield) was then obtained as light gray solid powder.

Figure 3:
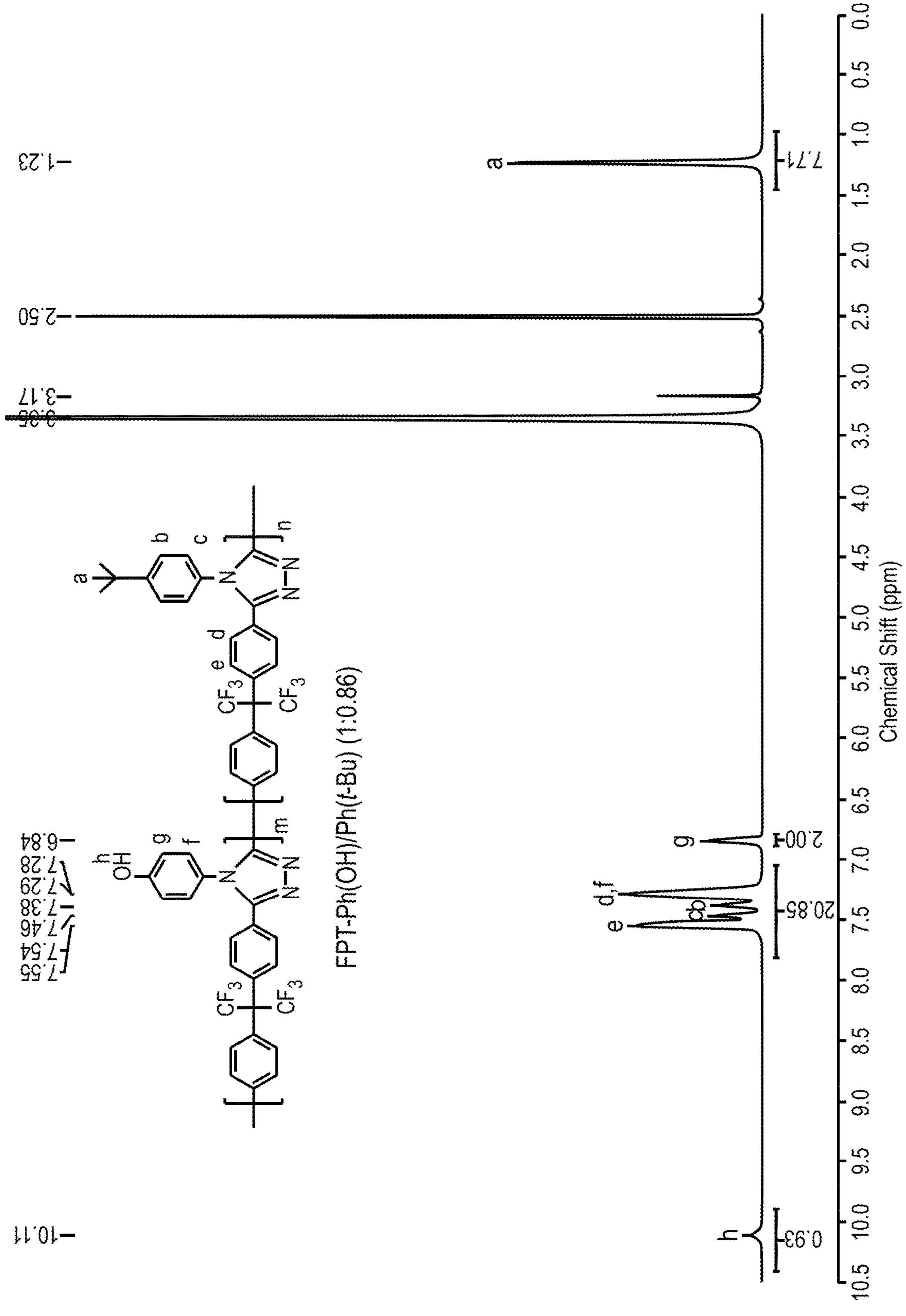
FIG. 3 shows an example $^1H$ NMR spectrum of FPT-Ph (OH)/Ph(t-Bu).

FIG. 3 shows an example $^{1}$H NMR analysis of the copoly(1,2,4-triazole) FPT-Ph(OH)/(t-Bu) with peaks at δ 10.11 (s, 1H), 7.81-7.04 (m, 21H), 6.84 (s, 2H), 1.23 (s, 8H). The chemical structure was confirmed by $^{1}$H NMR in deuterated DMSO-$d_6$. The spectrum depicts the aromatic protons corresponding to the phenyl rings all over the polymer backbone and two distinguished peaks: (1) one narrow singlet at 1.23 ppm that corresponds to the aliphatic protons of the tert-butyl group from the Ph(t-Bu) moiety, and (2) a broad singlet at 10.11 ppm that corresponds to the hydroxyl group from the Ph(OH) moiety. To calculate the molar ratio between the two Ph(OH)/Ph(t-Bu) moieties, the signal integration of the area of the aromatic peak from Ph(OH) at 6.84 ppm was set to be equal two protons (2H). Based on this calibration, the signal integration of the singlet at 1.23 ppm that corresponds to the tert-butyl protons from the Ph(t-Bu) moiety was determined as 7.71. From these results, the Ph(OH)/Ph(t-Bu) molar ratio is calculated to be 1:0.86 instead of the theoretical 1:1 ratio. Moreover, no traces of the poly(1,3,4-oxadiazole) peaks were observed in the $^{1}$H NMR spectrum, indicating the complete conversion of all the 1,3,4-oxadiazole rings into their corresponding 1,2,4-triazole rings.

Example 3: Preparation of the Fluorinated Copoly(1,2,4-Triazole): FPT-Ph(OH)/Ph($Me_2$) (1:1)

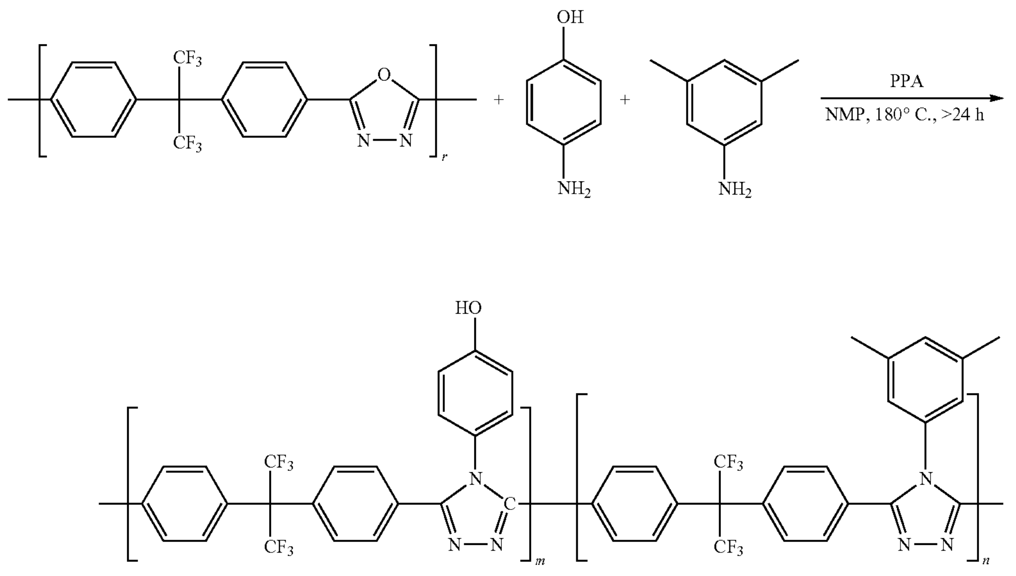

Figure 4:
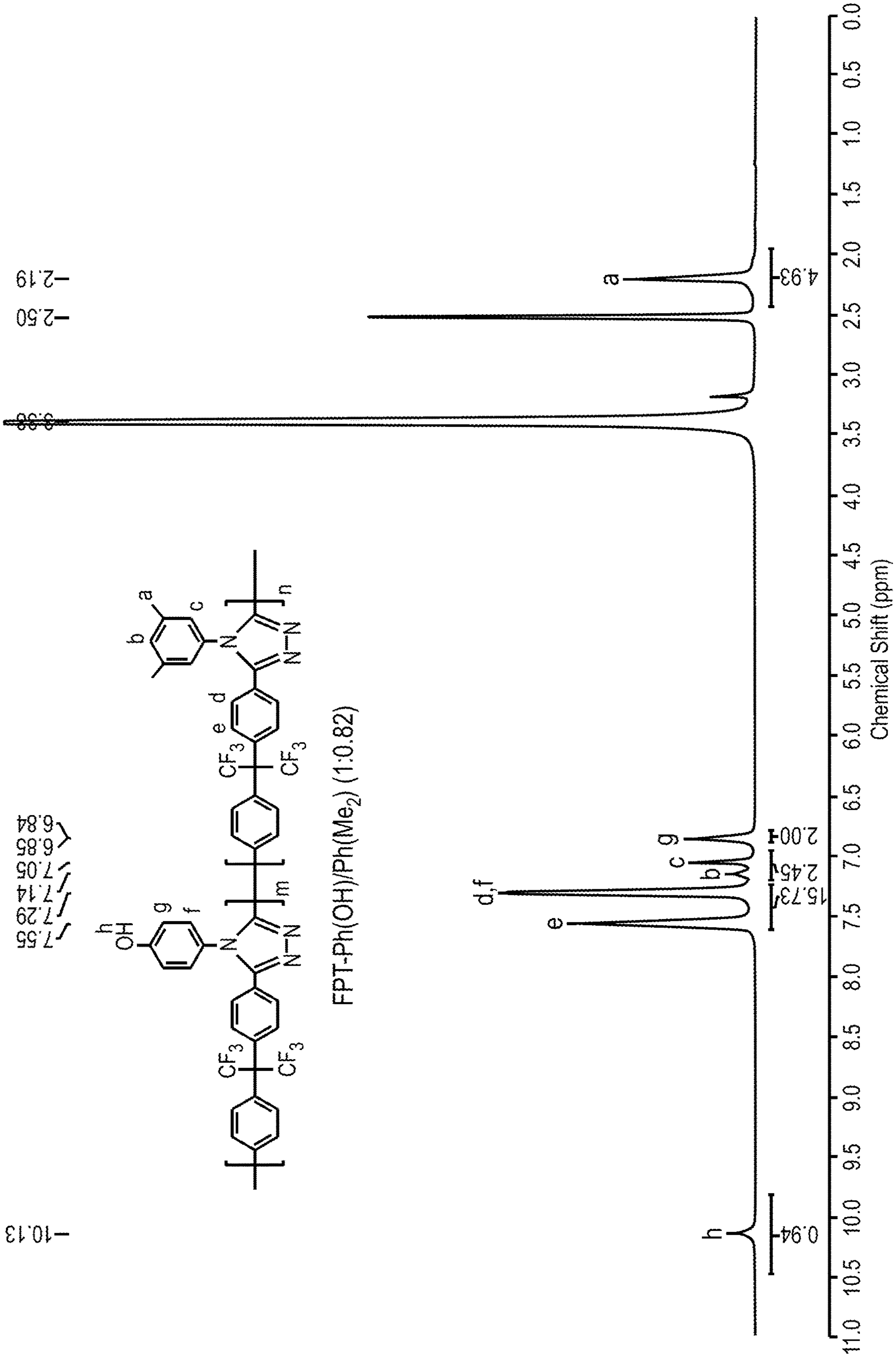
FIG. 4 shows an example $^1H$ NMR analysis of FPT-Ph (OH)/Ph($Me_2$).

In a 100-mL three-neck round bottom flask equipped with a nitrogen inlet and a mechanical stirrer, poly(1,3,4-oxadiazole) (POz-$CF_3$) (2.000 g, 5.00 mmol, 1.0 eq.), 4-aminophenol (0.327 g, 3.00 mmol, 0.6 eq.), and 3,5-dimethylaniline (0.374 mL, 3.00 mmol, 0.6 eq.) were introduced, followed by 20 mL of N-methyl-2-pyrrolidone (NMP) and polyphosphoric acid (PPA; 0.308 mL; 1.0 g; d=2.06 g/mL; used as a catalyst). The mixture was heated at 180° C. for 9 hours. The reaction progress was monitored by $^1$H-NMR. If needed, another portion of 4-aminophenol (0.327 g, 3.00 mmol, 0.6 eq.), and 3,5-dimethylaniline (0.374 mL, 3.00 mmol, 0.6 eq.) were added and the reaction mixture was further stirred for another 9 hours at 180° C. To ensure all the poly(1,3,4-oxadiazole) was converted into poly(1,2,4-triazole), 0.1 mL of 3,5-dimethylaniline was added and the reaction mixture was further stirred for another 9 hours at 180° C. The resulting viscous polymer was precipitated in water. The solid polymer was collected and 100 mL of methanol were added, and the mixture was further stirred overnight. The polymer was then collected through filtration and dried in an oven preheated to 70° C. for 24 hours. The final polymer FPT-Ph(OH)/Ph($Me_2$) (1:1) (2.338 g, 2.423 mmol, 97% yield) was then obtained as light gray solid powder. FIG. 4 shows an example $^1$H NMR analysis (500 MHz, DMSO-$d_6$) with peaks at δ 10.13 (s, 1H), 7.42 (d, J=128.3 Hz, 17H), 7.09 (d, J=45.8 Hz, 2H), 6.89-6.78 (m, 2H), 2.19 (s, 5H).

The molar ratio between Ph(OH) and Ph($Me_2$) moieties was calculated through the $^1$H NMR spectrum of FPT-Ph (OH)/Ph($Me_2$) in deuterated DMSO-$d_6$ (FIG. 4). The molar ratio was calculated by calculating the signal integration of the peak b at 6.85 ppm which corresponds to the aromatic protons (2H) adjacent to the hydroxyl group of the phenol ring, and the signal integration of the peak at 2.19 ppm, which corresponds to the aliphatic protons of the methyl groups in the Ph($Me_2$) moiety. The Ph(OH)/Ph($Me_2$) molar ratio is calculated to be (1:0.82).

Example 4: Preparation of FPT-pH(OH)/pH($Me_2$) (1:1) with a Precise Molar Ratio Between pH(OH) and pH($Me_2$)

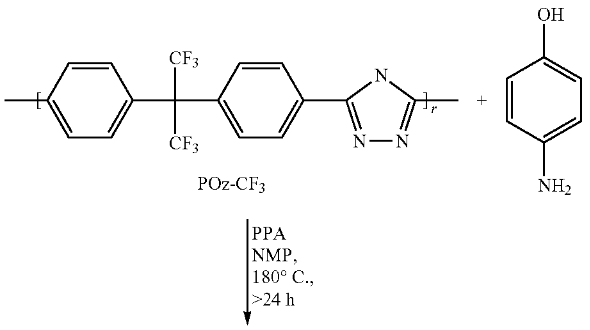

-continued

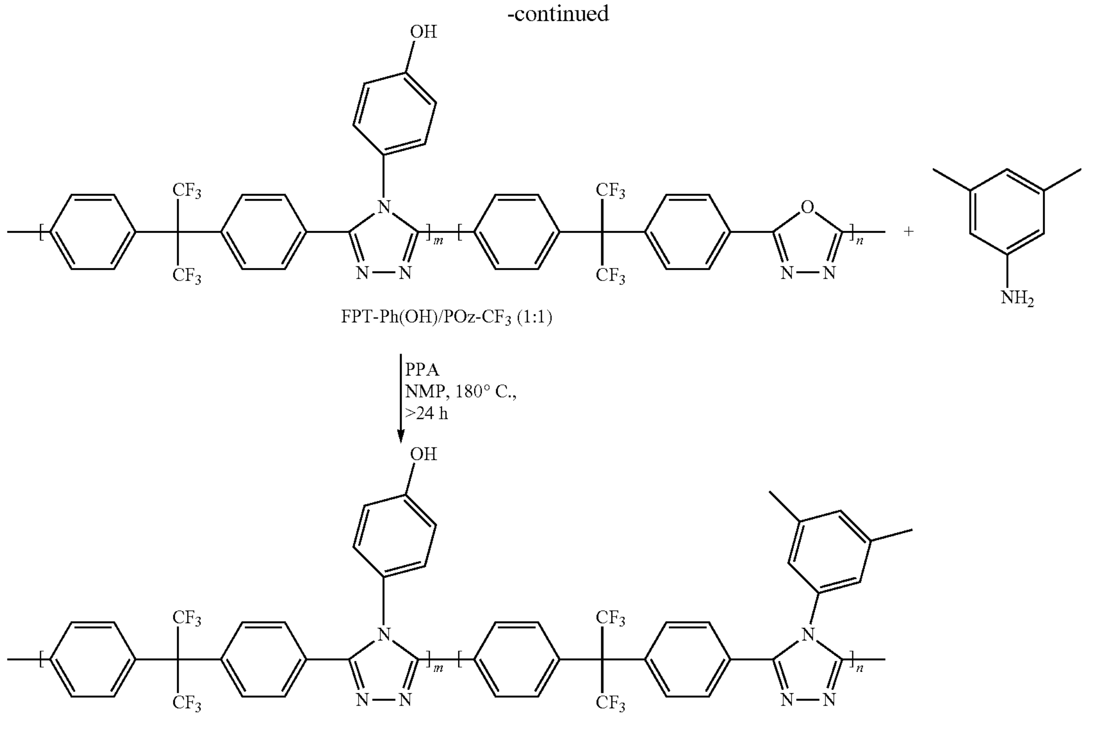

FPT-Ph(OH)/POz-$CF_3$ (1:1)

FPT-Ph(OH)/Ph($Me_2$) (1:1)

Figure 5:
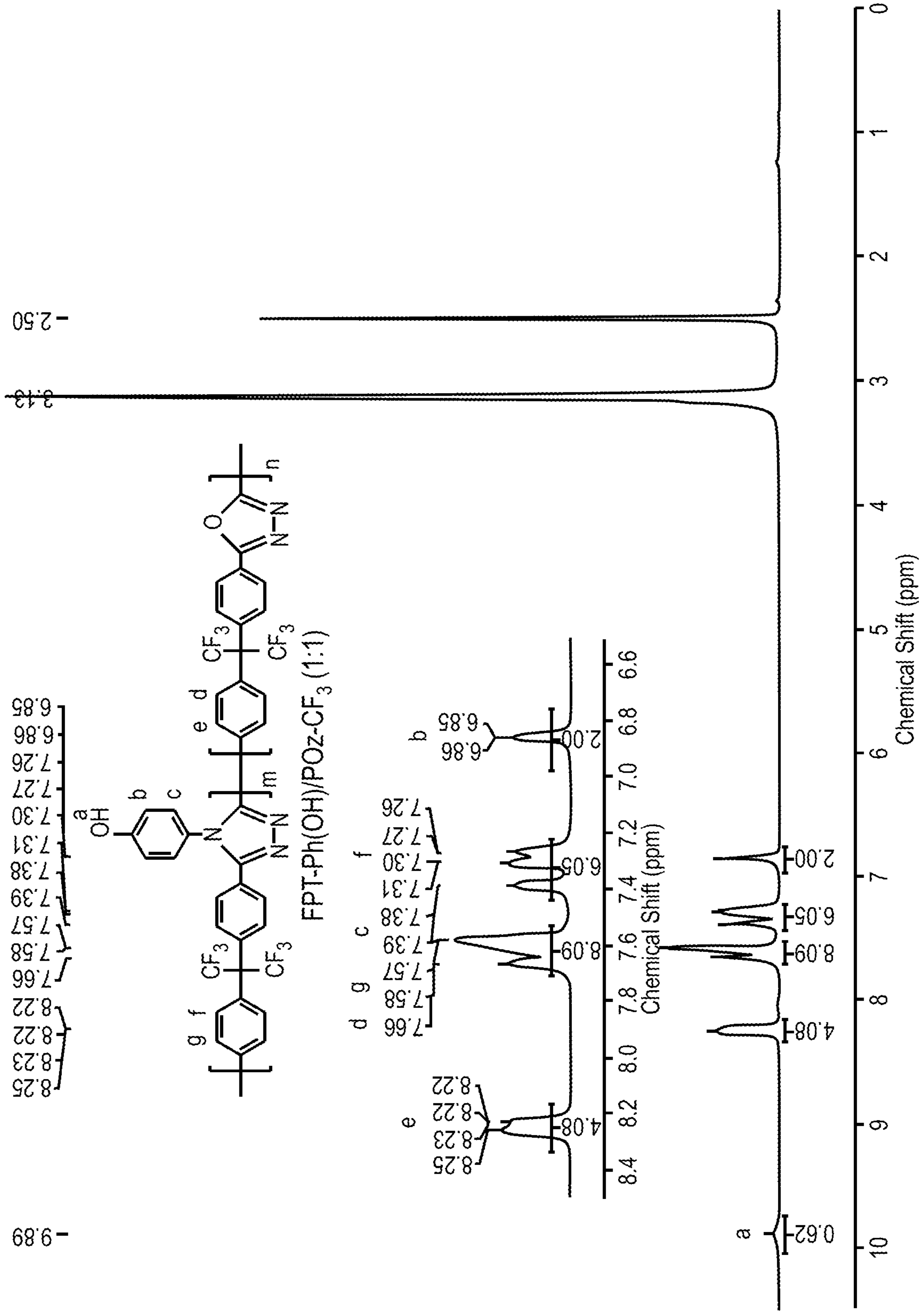
FIG. 5 shows an example $^1H$ NMR spectrum of FPT-Ph (OH)/POz-$CF_3$.

In this example, the copoly(1,2,4-triazole)-co-(1,3,4-oxadiazole), FPT-Ph(OH)/POz-$CF_3$, was prepared with a molar ratio of (1.1), where 50% of the 1,3,4-oxadiazole rings within the poly(1,3,4-oxadiazole) backbone have been converted to 1,2,4-triazole, using 4-aminophenol as substituent (aniline derivative). The progress of the reaction was followed carefully using $^1$H NMR to ensure the molar ratio between 1,2,4-triazole/1,3,4-oxadiazole is equal to 1.1. FIG. 5 shows an example $^1$H NMR spectrum of the FPT-Ph(OH)/POz-$CF_3$ product.

Figure 6:
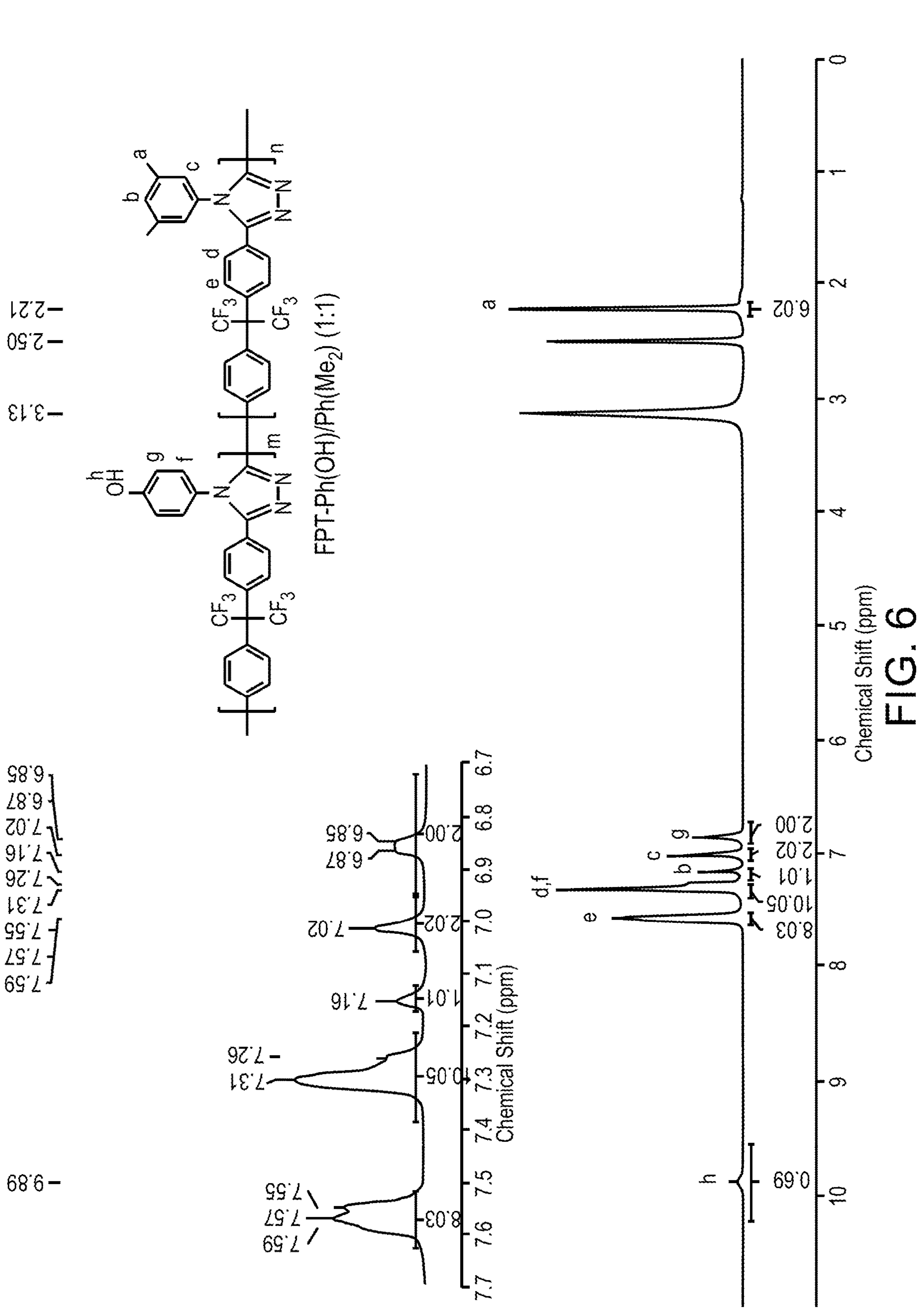
FIG. 6 shows an example $^1H$ NMR spectrum of FPT-Ph (OH)/POz-$CF_3$.

The prepared FPT-Ph(OH)/POz-$CF_3$ (1:1) copolymer was then used in the next step where it was reacted with 3,5-dimethylaniline [$H_2$N-Ph($Me_2$)] to prepare the copoly (1,2,4-triazole) FPT-Ph(OH)/Ph($Me_2$) (1:1). This route ensured the preparation of an exact 1:1 molar ratio between Ph(OH) and Ph($Me_2$) by introducing the aniline derivatives sequentially, in contrast to Example 3, where both aniline derivatives (4-aminophenol and 3,5-dimethylaniline) were added at the reaction at same time. FIG. 6 shows an example $^1$H NMR spectrum in deuterated DMSO, confirming the 1:1 molar ratio of FPT-Ph(OH)/Ph($Me_2$) as prepared in this example.

Example 5: Preparation of the Fluorinated Copoly(1,2,4-Triazole): FPT-pH(OH)/pH($CF_3$,F) (1:1)

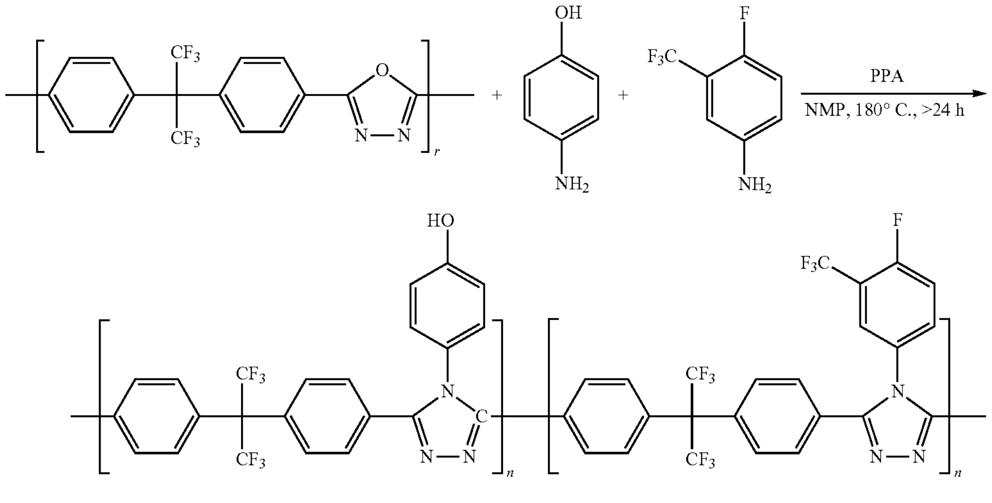

In a 100-mL three-neck round bottom flask equipped with a nitrogen inlet and a mechanical stirrer, poly(1,3,4-oxadiazole) (POz-$CF_3$) (1.000 g, 2.498 mmol, 1.0 eq.), 4-aminophenol (0.164 g, 1.499 mmol, 0.6 eq.), and 4-fluoro-3-(trifluoromethyl)aniline (0.193 mL, 1.499 mmol, 0.6 eq.) were introduced, followed by 10 mL of N-methyl-2-pyrrolidone (NMP) and polyphosphoric acid (PPA; 0.154 mL; 1.0 g; d=2.06 g/mL; used as a catalyst). The mixture was heated at 180° C. for 9 hours. The reaction progress was monitored by $^1$H-NMR. If needed, another portion of 4-aminophenol (0.164 g, 1.499 mmol, 0.6 eq.), and 4-fluoro-3-(trifluoromethyl)aniline (0.193 mL, 1.499 mmol, 0.6 eq.) were added and the reaction mixture was further stirred for another 9 hours at 180° C. To ensure all the poly(1,3,4-oxadiazole) is converted into poly(1,2,4-triazole), 0.1 mL of 4-fluoro-3-(trifluoromethyl)aniline was added and the reaction mixture was further stirred for another 9 hours at 180° C. The resulting viscous polymer was precipitated in water. The solid polymer was collected and 100 mL of methanol were added, and the mixture was further stirred overnight. The polymer was then collected through filtration and dried in an oven preheated to 70° C. for 24 hours. The final polymer FPT-Ph(OH)/Ph($CF_3$,F) (1.226 g, 1.199 mmol, 96% yield) was then obtained as white solid powder.

Figure 7:
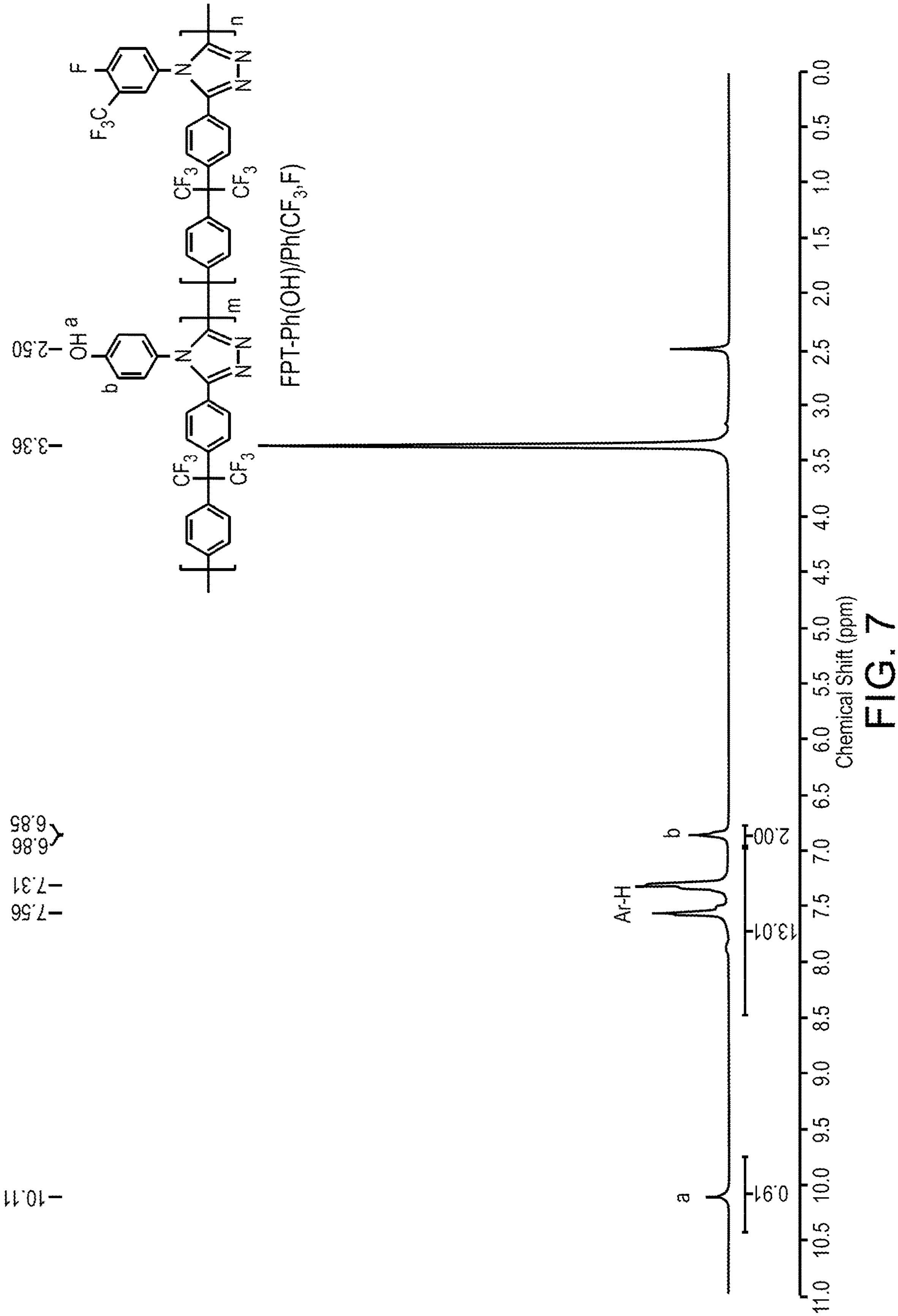
FIG. 7 shows an example $^1H$ NMR analysis of FPT-Ph (OH)/Ph($CF_3$,F).
Figure 8:
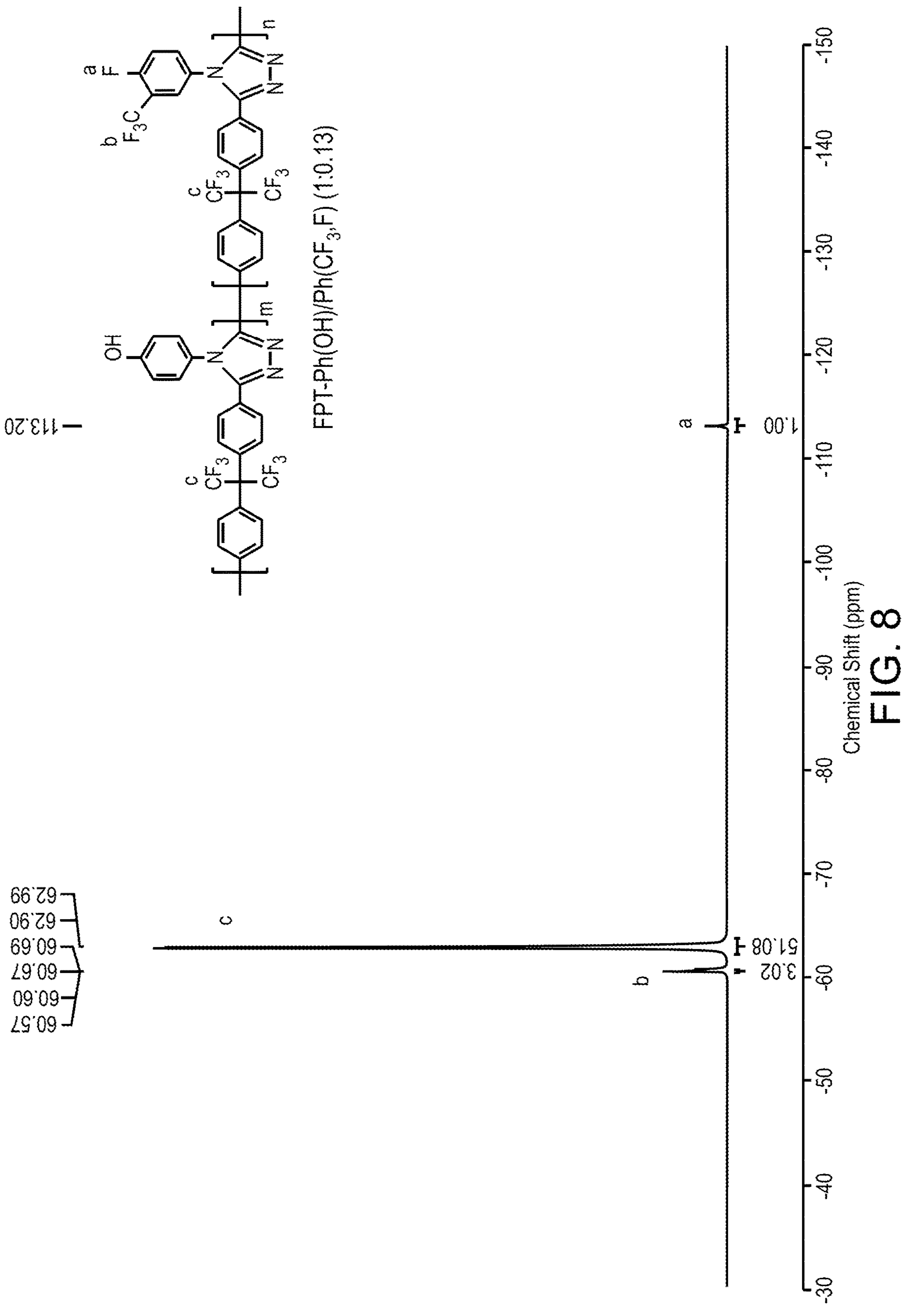
FIG. 8 shows an example $^{19}F$ NMR spectrum of FTP-Ph (OH)/Ph($CF_3$,F).

FIG. 7 shows an example $^1$H NMR analysis (500 MHz, DMSO-$d_6$) of FPT-Ph(OH)/Ph($CF_3$,F) with peaks at δ 10.11 (s, 1H), 8.06-7.66 (m, 1H), 7.56 (s, 5H), 7.31 (s, 7H), 6.97-6.75 (m, 2H). The molar ratio between Ph(OH) and Ph($CF_3$,F) cannot be calculated from the corresponding $^1$H NMR spectrum of FPT-Ph(OH)/Ph($CF_3$,F) in deuterated DMSO-$d_6$. The absence of any aliphatic protons and the overlapping of the aromatic protons signals hinders the determination of the Ph(OH)/Ph($CF_3$,F) molar ratio from the $^1$H NMR spectrum of FPT-Ph(OH)/Ph($CF_3$,F). However, the Ph(OH)/Ph($CF_3$,F) molar ratio within the FPT-Ph(OH)/Ph($CF_3$,F) copoly(1,2,4-triazole) backbone can be determined from its $^{19}$F NMR spectrum in deuterated DMSO-$d_6$. FIG. 8 shows an example $^{19}$F NMR spectrum of FTP-Ph(OH)/Ph($CF_3$,F) copoly(1,2,4-triazole) in deuterated DMSO-$d_6$. The singlet peak at −113.20 ppm is assigned to the fluorine (F) atom of Ph($CF_3$,F) and its signal integration is then set to 1. The multiplet peak at −60.60 ppm is assigned to the trifluoromethyl ($CF_3$) group of Ph($CF_3$,F) and its signal integration is set equal to 3. The multiplet peak at −62.90 ppm is assigned to the trifluoromethyl ($CF_3$) groups of the hexafluoroisopropyl groups (—$C(CF_3)_2$) within the polymer backbone. The Ph(OH)/Ph($CF_3$,F) molar ratio was calculated to be (1:0.13).

Example 6: Preparation of FPT-pH(OH)/pH-($CF_3$,F) with a Precise Molar Ratio Between pH(OH) and pH($CF_3$,F)

Figure 9:
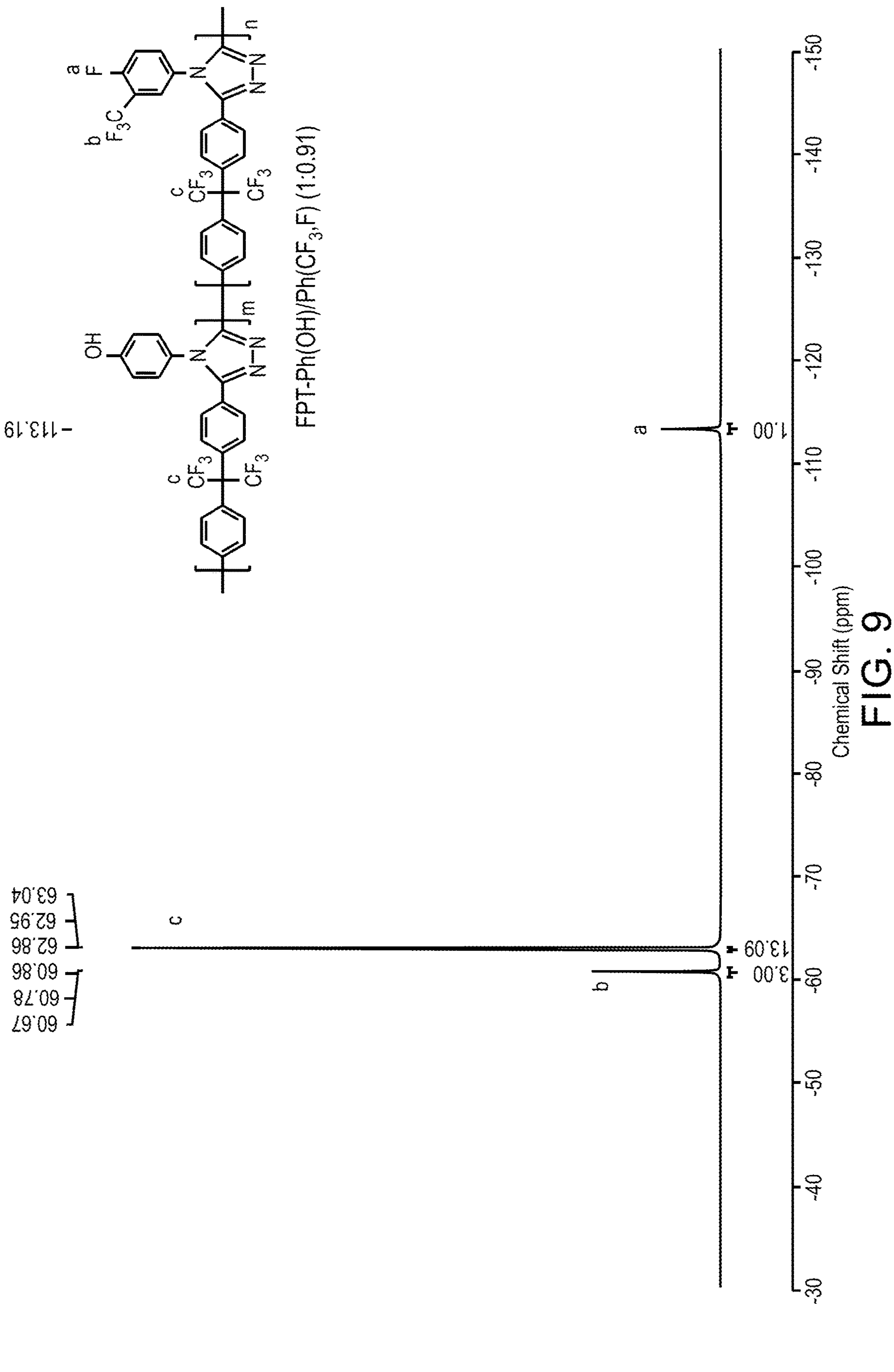
FIG. 9 shows an example $^{19}F$ NMR spectrum of FPT-Ph (OH)/Ph($CF_3$,F) (1:0.91).

Similar to Example 5, FPT-(Ph(OH)/Ph($CF_3$,F) was prepared from FPT-Ph(OH)/POz-$CF_3$ (1:1) and 4-fluoro-3-(trifluoromethyl)aniline [Ph($CF_3$,F)] with an exact molar ratio of 1:1. With the reaction progressing, and more and more Ph($CF_3$,F) is substituted to the copolymer backbone, the solubility of the product reduced until all the copolymer crashed out of the reaction medium. Afterwards, the copoly (1,2,4-triazole) FPT-Ph(OH)/Ph($CF_3$,F) was collected out of the reaction. Due to the low solubility in DMSO-$d_6$ or $CDCl_3$, the $^1$H NMR spectrum was recorded in a mixture of DMSO-$d_6$/DMF (6/1 v/v ratio; nondeuterated DMF). The exact molar ratio could not be determined from the $^1$H NMR due to the interference with the DMF corresponding peaks. Hence, the $^{19}$F NMR spectrum was recorded and allowed the determination of the molar ratio between Ph(OH) and Ph($CF_3$,F) to be found equal to 1:0.91. An example $^{19}$F NMR spectrum of FPT-Ph(OH)/Ph($CF_3$,F) (1:0.91) is shown in FIG. 9.

Example 7: Preparation of FPT-Ph(OH)/POz-$CF_3$ (1:1)

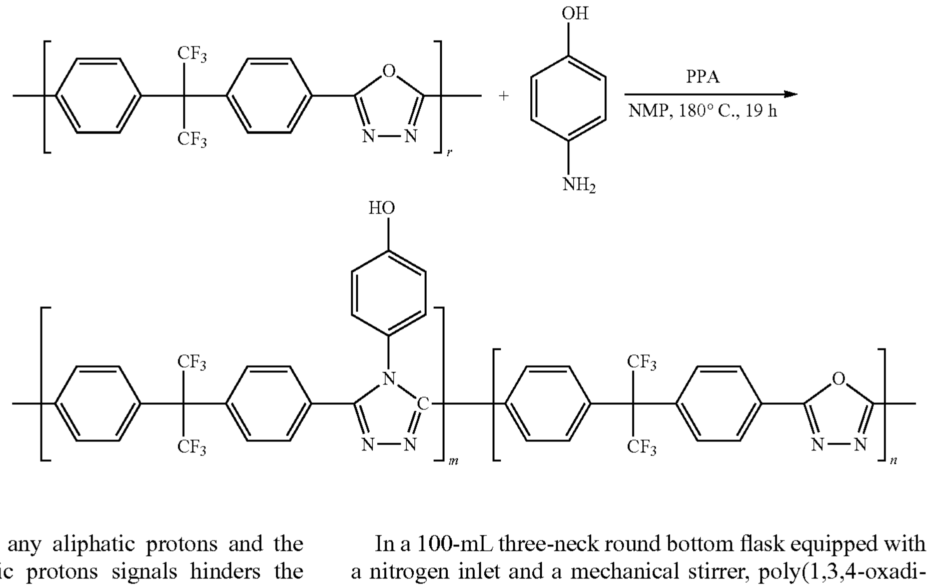

In a 100-mL three-neck round bottom flask equipped with a nitrogen inlet and a mechanical stirrer, poly(1,3,4-oxadiazole) (POz-$CF_3$, 3.000 g, 7.49 mmol) was dissolved in NMP (ratio: 61.9, volume: 30 mL). Next, 4-aminophenol (0.818 g, 7.49 mmol) was introduced followed by PPA (ratio: 1.000, volume: 0.485 mL; 1.0 g; d=2.06 g/mL; used as a catalyst). The mixture was heated at 180° C. for a total of 19 hours: 4 hours+4 hours+7 hours+2 hours+2 hours. After each time interval, an $^1$H NMR spectrum was recorded to monitor the progress of the reaction: 4 hours ($CDCl_3$; 40% progress)+4 hours (DMSO-$d_6$ [70° C.]; 51.6% progress)+7 hours (DMSO-$d_6$ [70° C.]; 74.2% progress)+2 hours (DMSO-$d_6$ [70° C.]; 86.7% progress)+1.5 hours (DMSO-$d_6$ [70° C.]; 87.2% progress)+2 hours (DMSO-$d_6$ [70° C.]; 100% progress). The resulting viscous polymer was precipitated in methanol and the mixture was further stirred overnight. The polymer was further washed with methanol (3×100 mL), then collected through filtration and dried in an oven at 70° C. for 24 hours. The final polymer FPT-Ph(OH)/POz-$CF_3$ (1:1) (3.23 g, 3.75 mmol, 100% yield) was then obtained as white fibrous solid. $^1H$ NMR analysis (500 MHz, DMSO-$d_6$) yielded peaks at δ 8.39-8.09 (m, 4H), 7.71-7.54 (m, 8H), 7.43-7.19 (m, 6H), 6.86 (d, J=6.9 Hz, 2H).

Example 8: FTIR Analysis of Copoly(1,2,4-Triazole)s

The presence of the functional groups within the copoly(1,2,4-triazole)s backbones, such as hydroxyl, tert-butyl, and methyl groups were confirmed using Fourier transform infrared (FTIR) spectroscopy. The hydroxyl stretching broad band is illustrated between 3200 and 3400 $cm^{-1}$. The stretching bands for the C—H bonds of the tert-butyl group or a methyl group could be found between 2600-2960 $cm^{-1}$. The peaks between 700 and 900 $cm^{-1}$ could be attributed to the aromatic C—H bonds.

Figure 10:
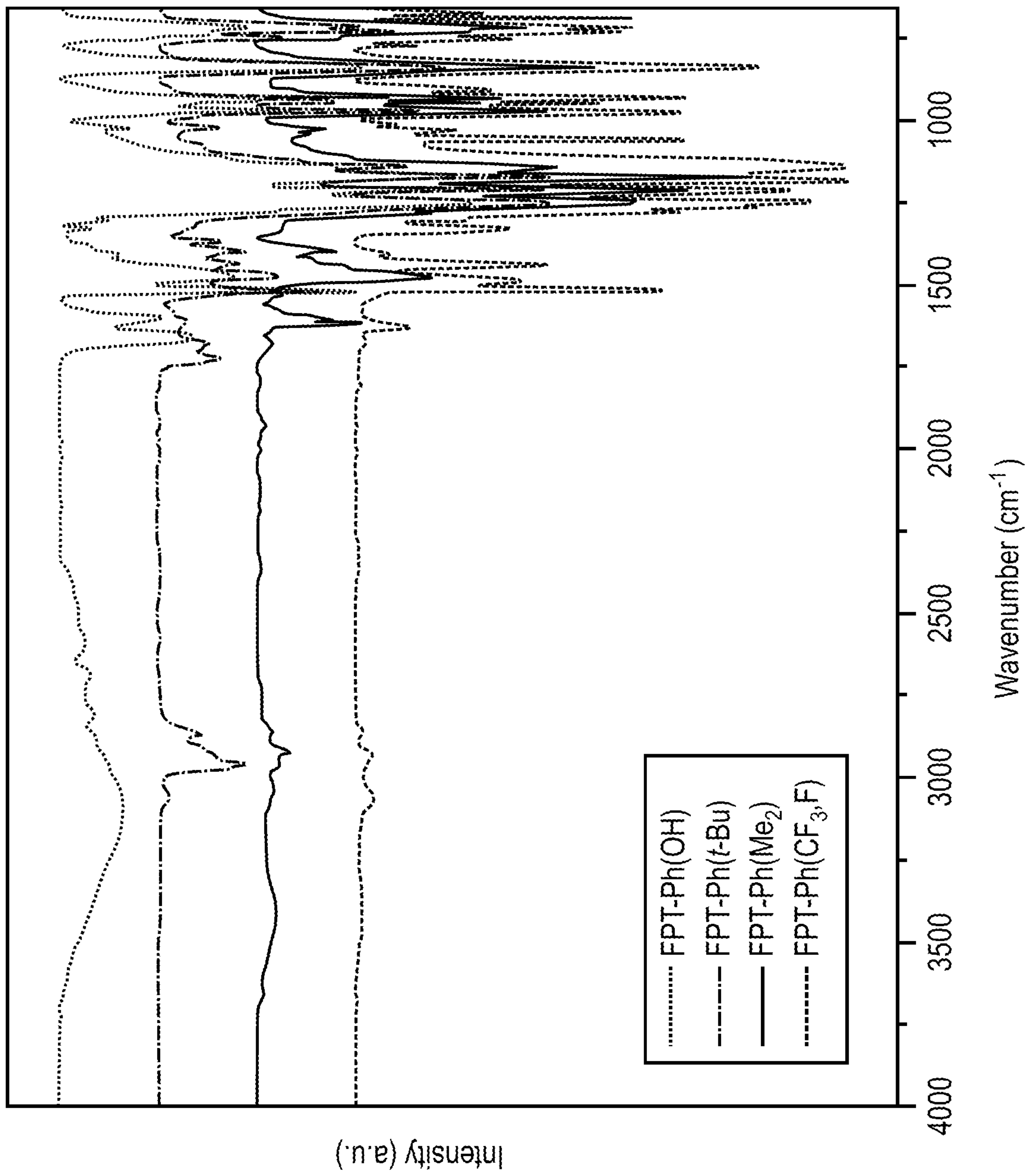
FIG. 10 shows an example FTIR spectrum of homopoly (1,2,4-triazole)s.
Figure 11:
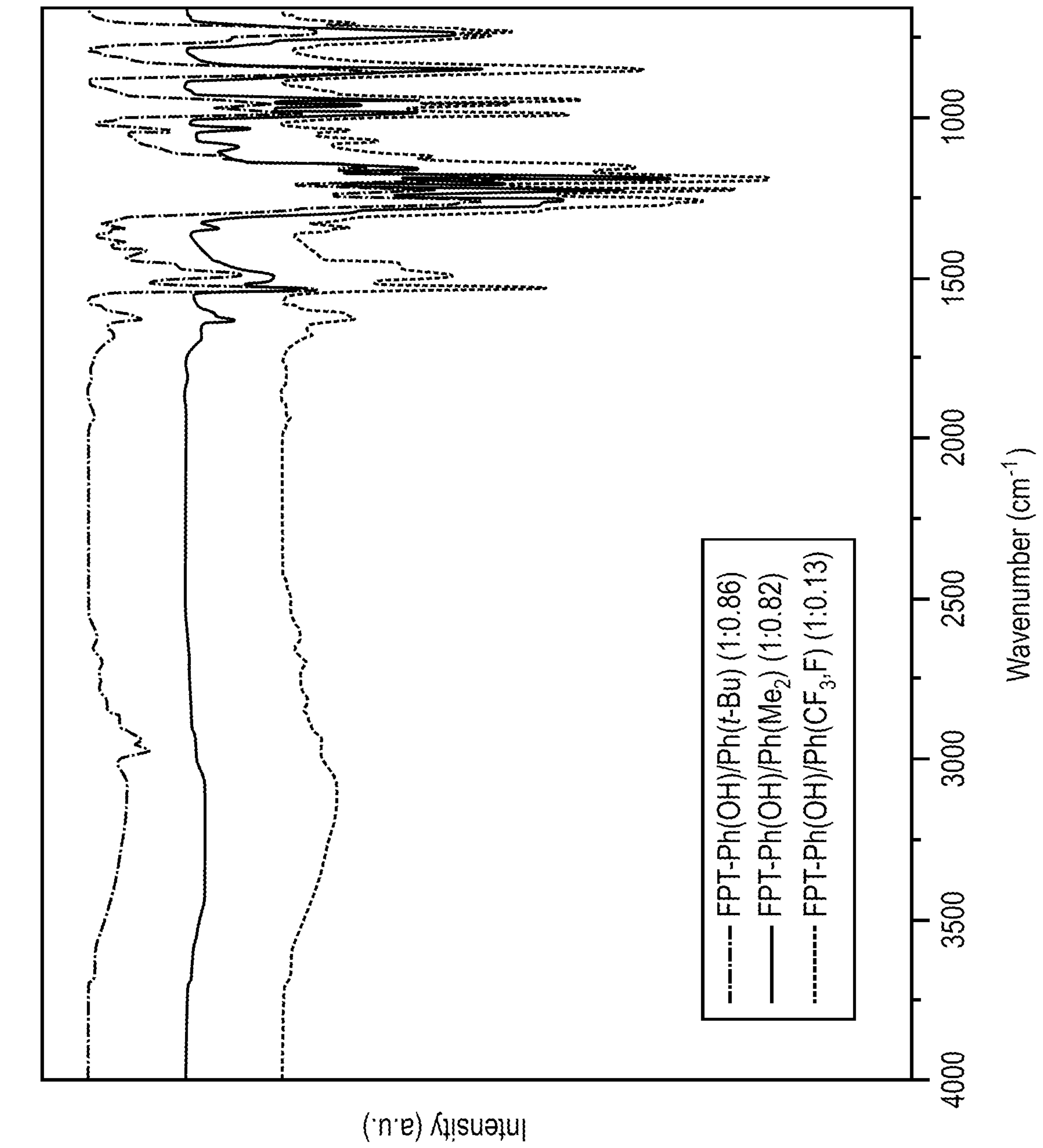
FIG. 11 shows an example FTIR spectrum of copoly(1, 2,4-triazoles).

FIG. 10 shows an example FTIR spectrum of homopoly(1,2,4-triazole)s. FIG. 11 shows an example FTIR spectrum of the copoly(1,2,4-triazoles) described herein. While the bands corresponding to the different functional groups within the homopoly(1,2,4-triazole) appear very well defined in the FTIR spectra (FIG. 10), the FTIR spectra for the copoly(1,2,4-triazole)s show the combination of the functional groups that correspond to the aniline derivatives used to prepare the copolymer (FIG. 11).

Example 9: Thermal and Physical Properties of Copoly(1,2,4-Triazole)s

Figure 12:
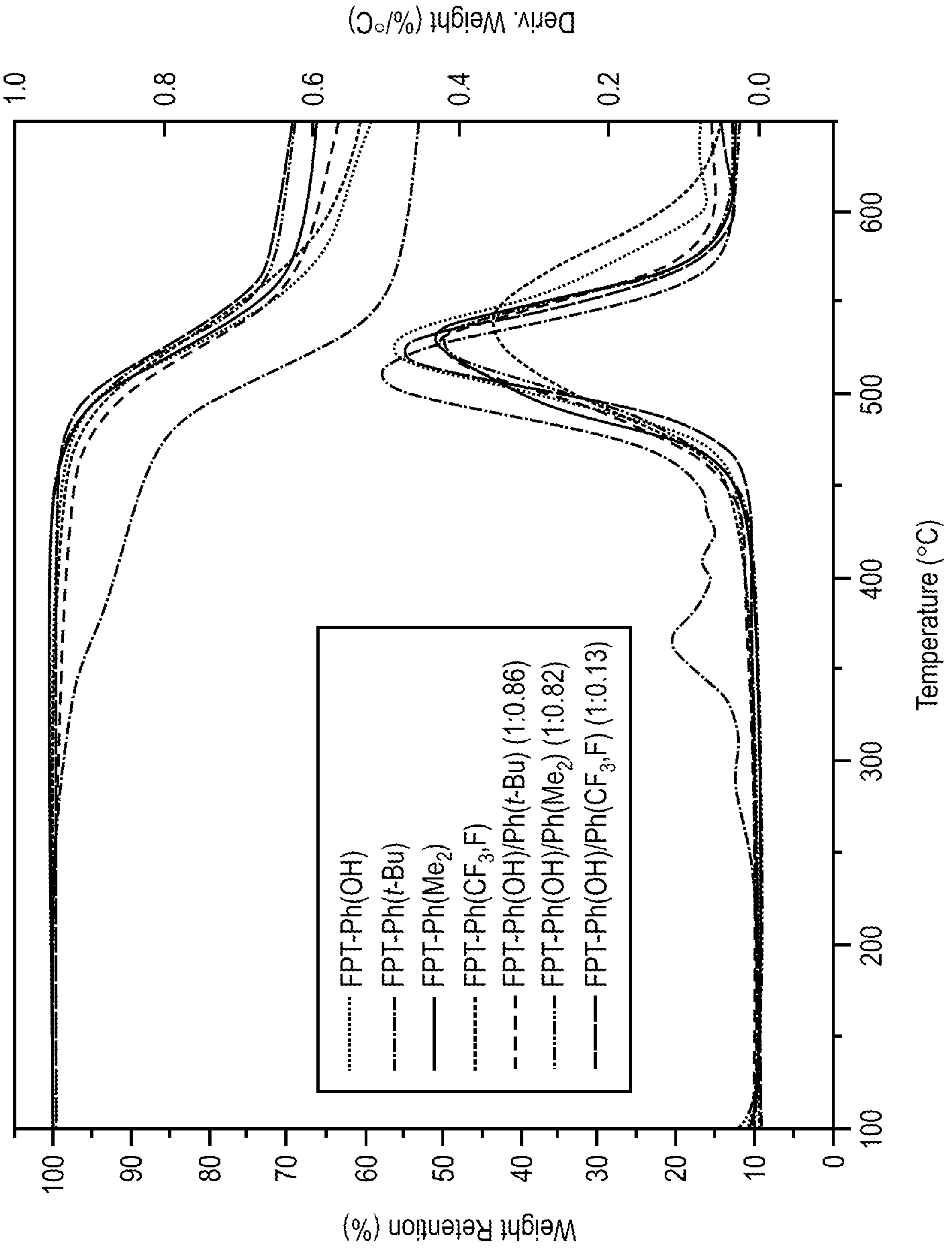
FIG. 12 shows an example thermogravimetric analysis (TGA) and the first derivative curves (DTG) of the homo- and copoly(1,2,4-triazole)s.
Figure 13:
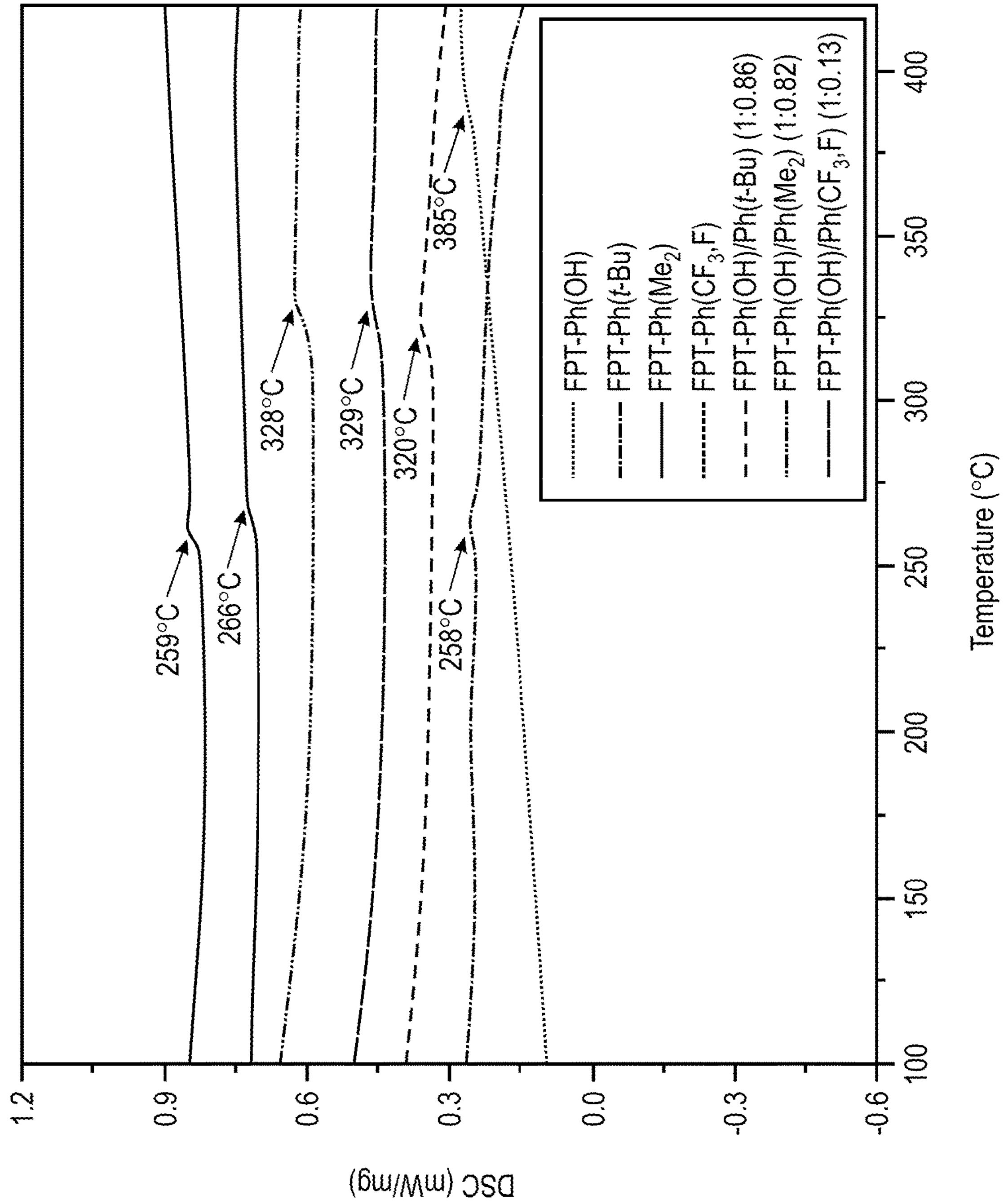
FIG. 13 shows an example differential scanning calorimetric analysis of homo- and copoly(1,2,4-triazole)s.

The thermal properties of the prepared copoly(1,2,4-triazole)s were measured using thermal gravimetric analysis (TGA) and differential scanning calorimetry (DSC). FIG. 12 shows an example thermogravimetric analysis (TGA) and the first derivative curves (DTG) of the homo- and copoly(1,2,4-triazole)s. FIG. 13 shows an example differential scanning calorimetric analysis of the homo- and copoly(1,2,4-trizaole)s prepared herein.

The decomposition temperatures at 5% and 10% were determined (Table 1) to assess the thermal stability of the disclosed copoly(1,2,4-triazole)s during the harsh conditions of gas separation tests. The $T_{d5\%}$ of the prepared polymers found to be higher than 480° C. which indicates a high thermal stability and suitability for use in gas separation technology. The first derivatives of the TGA curves (FIG. 12) were calculated and the values are listed in Table 1. These values (>520° C.) indicate the highest temperature at which the polymer degrades the fastest, and are additional indication of the high thermal stability of the prepared polymers.

TABLE 1

Thermal Properties of the prepared copoly(1,2,4-triazole)s

| | DSC | TGA | | |
|---|---|---|---|---|
| Polymer sample | $T_g$ (° C.) | $T_{d5\%}$ (° C.) | $T_{d10\%}$ (° C.) | DTG (° C.) |
| FPT-Ph(OH) | 386 | 495 | 511 | 525 |
| FPT-Ph(t-Bu) | 258 | 353 | 463 | 513 |
| FPT-Ph($Me_2$) | 259 | 493 | 508 | 530 |
| FPT-Ph($CF_3$, F) | 266 | 488 | 510 | 538 |
| FPT-Ph(OH)/Ph(t-Bu) (1:0.86) | 320 | 480 | 503 | 525 |
| FPT-Ph(OH)/Ph($Me_2$) (1:0.82) | 328 | 496 | 513 | 528 |
| FPT-Ph(OH)/Ph($CF_3$, F) (1:0.13) | 329 | 503 | 515 | 523 |
| FPT-Ph(OH)/POz-$CF_3$ (1:1) | 329 | 489 | 505 | 522 |
| FPT-Ph(OH)/Ph($CF_3$, F) (1:0.91) | 333 | 491 | 508 | 523 |
| FPT-Ph(OH)/Ph($Me_2$) (1:1) | 322 | 456 | 484 | 526 |

The glass transition temperatures ($T_g$) of the prepared copoly(1,2,4-triazole)s were calculated from their corresponding DSC traces and the values are listed in Table 1. These temperatures are indicative of the rigidity of the polymeric chains, which can be correlated to their performance during gas separation testing. The values obtained as similar to other glassy polymers used in gas separation technology.

Example 10: Dense Membrane Preparation

Dense membranes of the copoly(1,2,4-triazole)s with a thickness between 60-100 μm were prepared using the solution casting method in dimethylformamide (DMF) as the solvent. A polymer solution of 3 wt. % concentration was prepared and 12 mL of this solution was filtered through a 0.45 μm Teflon filter to remove any solid particles impurities, and then transferred into a glass Petri dish of a 5 cm diameter. The Petri dish was placed on a leveled support in an oven preheated to 90° C. and the solvent was slowly evaporated under a gentle nitrogen flow. When the membrane formed (after ~36 hours), the oven temperature was increased to 180° C. and vacuum was applied to remove any traces of residual solvent within the membrane matrix. The formed membrane was cut using a 4 cm diameter cutter, for a perfect fitting into the membrane cell of the gas permeation testing system. Thicknesses of between 60-100 μm were prepared for this example, however, the membranes described herein are not limited to this range. For example, a membrane can be prepared with a thickness between 0.5 and 100 μm.

The fractional free volume (FFV) values of membranes prepared from the studied copoly(1,2,4-triazole)s were calculated using the following equation:

$$FFV = \frac{V - V_0}{V}$$

where V is the specific volume and $V_0$ is the occupied volume by the polymer. V is the reciprocal of the polymer density and can be determined experimentally. The densities of the prepared copoly(1,2,4-triazole)s were measured using a Mettler Toledo XPE205 balance equipped with a density kit using cyclohexane (d=0.777 g/$cm^3$) as the buoyant liquid at 20° C. The density values are reported in Table 2 and are the average values of at least five different measurements, with error values (standard deviation) below 5%. The occupied volume ($V_0$) values were calculated from the Van der Waals volumes ($V_w$) using Bondi's equation:

$$V_0 = 1.3 \times V_w$$

The Van der Waals volumes of copolymers were calculated from the individual $V_w$ of the constituent homopolymers taking into consideration their different molar ratios in the copolymer backbone using the following equation:

$$V_w = X_1 V_{w_1} + X_2 V_{w_2}$$

where $X_1$ and $X_2$ are the molar ratios and $V_{w1}$ and $V_{w2}$ are the van der Waals volumes of the constituent homopolymers. The van der Waals volumes were estimated via simulations rather than the Bondi's group contribution method. In brief, the Van de Waals volume ($V_w$) was estimated from the known $V_w$ of the individual atoms within the molecule.

Table 2 shows the density and fractional free volume (FFV) of the prepared poly(imide-oxadiazole) compounds. The results listed in Table 2 show a clear difference in the FFV for copoly(1,2,4-triazole) membranes when compared to their parent homopolymers due to the incorporation of various functional groups with different occupied volume. For example, the FFV value of the homopolymer FPT-Ph (OH) is 0.1840, and that of FPT-Ph(t-Bu) is 0.1940. The FFV of the copoly(1,2,4-triazole) FPT-Ph(OH)/Ph(t-Bu) is between the FFV values of its constituent parent homopolymers. It can be seen from the data listed in Table 2, the bulkier the functional group in the copoly(1,2,4-triazole) backbone, the higher the FFV value. These results will be correlated to the gas permeation results as described herein.

TABLE 2

Density and fractional free volume (FFV) values of the prepared poly(imide-oxadiazole) samples.

| Polymer sample | $V_0$ ($cm^3/g$) | V ($cm^3/g$) | d ($g/cm^3$) | FFV |
|---|---|---|---|---|
| FPT-Ph(OH) | 0.6074 | 0.7444 | 1.3434 | 0.1840 |
| FPT-Ph(t-Bu) | 0.6527 | 0.8097 | 1.2350 | 0.1940 |
| FPT-Ph($Me_2$) | 0.6338 | 0.7764 | 1.2880 | 0.1837 |
| FPT-Ph($CF_3$, F) | 0.5695 | 0.6976 | 1.4335 | 0.1837 |
| FPT-Ph(OH)/Ph(t-Bu) (1:0.86) | 0.6283 | 0.7683 | 1.3016 | 0.1821 |
| FPT-Ph(OH)/Ph($Me_2$) (1:0.82) | 0.6193 | 0.7472 | 1.3384 | 0.1711 |
| FPT-Ph(OH)/Ph($CF_3$, F) (1:0.13) | 0.5885 | 0.7256 | 1.3782 | 0.1689 |

Example 11: Pure- and Mixed-Gas Permeation Measurements, Pure-Gas Permeation Measurement The gas transport process through nonporous membranes occurs in three stages: the first stage involves the sorption of the gas penetrant into the membrane, followed by the diffusion of the gas particle through the membrane matrix driven by concentration gradient, and the last stage of this process is represented by the desorption of the gas particle to the permeate side. Based on this, the transport process is called a "solution-diffusion" process.

In general, a separation membrane can be evaluated by its two intrinsic key characteristics: permeability (P) and selectivity (α). The permeability defines the productivity of the membrane, while the selectivity represents its efficiency. Experimentally, the permeability of a single gas stream through nonporous membranes can be determined using a constant-volume/variable-pressure system using the following expression:

$$P = 10^{10} \frac{V_d l}{p_f ART}\left[\left(\frac{dp_p}{dt}\right)_{ss} - \left(\frac{dp_p}{dt}\right)_{leak}\right]$$

where $V_d$ is the permeate tube volume ($cm^3$), l is the membrane thickness (cm), $p_f$ is the gas feed pressure (cmHg), A is the membrane effective surface area ($cm^2$), R is the universal gas constant ($R=0.278\ cm^3 \cdot cmHg \cdot cm^{-3}$ (STP)$\cdot K^{-1}$), T is the operational temperature (K), $$\left(\frac{dp_p}{dt}\right)_{ss}$$

is the steady-state (ss) pressure variation in the permeate side (cmHg), and $$\left(\frac{dp_p}{dt}\right)_{leak}$$

is the leak rate of the system, which is in most cases very small and thus could be neglected. The permeability unit is used as Barrer, where 1 Barrer=$10^{-10}$ $cm^3$(STP)$\cdot cm \cdot cm^{-2} \cdot s^{-1} \cdot cmHg^{-1}$.

The ideal selectivity (α) of the membrane for separating two distinguished gases A and B can be determined through their single gas permeability coefficients ($P_A$ and $P_B$) using the following equation:

$$\alpha_{A/B} = \frac{P_A}{P_B}$$

The permeability coefficient is governed by two main stages of the gas permeation process: sorption and diffusion. The sorption of a gas penetrant into the membrane, which is a thermodynamic process, depends mainly on the gas properties (condensability and gas-polymer affinity), however, the diffusion, which is a kinetic process, depends on the gas particle size (kinetic diameter). The smaller the kinetic diameter, the higher the diffusion rate. Therefore, the permeability can be defined using the following expression:

$$P = D \times S$$

where D is the diffusivity coefficient ($cm^2/s$), and S is the solubility coefficient ($cm^3$(STP)$\cdot cm^{-3} \cdot cmHg^{-1}$). Using this equation, the ideal selectivity expression could be modified using the solubility and diffusivity coefficients by:

$$\alpha_{A/B} = \frac{P_A}{P_B} = \left(\frac{D_A}{D_B}\right) \times \left(\frac{S_A}{S_B}\right)$$

The diffusivity coefficient can be experimentally determined using the time-lag method through the following expression:

$$D = \frac{l^2}{6\theta}$$

where, l is the membrane thickness (cm) and θ is the time-lag (s). The solubility coefficient can thereafter be deduced from the permeability equation:

$$S = \frac{P}{D}$$

The pure-gas permeation properties of copoly(1,2,4-triazole) membranes were measured using a custom made constant-volume/variable-pressure permeation system. For this study, four different pure gases were used: helium (He), nitrogen ($N_2$), methane ($CH_4$) and carbon dioxide ($CO_2$). The permeability and selectivity coefficients of the membranes were calculated from the steady state of the pressure versus time curve, using a constant feed pressure of 100 psi and an operating temperature of 22° C. The obtained results are listed in Table 3. The permeability coefficients are listed in Barrer, where 1 Barrer=$10^{-10}$ $cm^3$(STP)·cm·$cm^{-2}$·$s^{-1}$·$cmHg^{-1}$.

TABLE 3

Pure gas permeability and selectivity coefficients for copoly(1,2,4-triazole) membranes measured at 100 psi and 22° C.

| Membrane | Permeability coefficients (Barrer) He | $N_2$ | $CH_4$ | $CO_2$ | Selectivity coefficients He/$CH_4$ | $N_2$/$CH_4$ | $CO_2$/$CH_4$ |
|---|---|---|---|---|---|---|---|
| FPT-Ph(OH) | 229 | 10.2 | 6.69 | 267 | 34.3 | 1.52 | 40.0 |
| FPT-Ph(t-Bu) | 101 | 5.83 | 6.12 | 86.8 | 16.5 | 0.953 | 14.2 |
| FPT-Ph($Me_2$) | 138 | 8.02 | 7.00 | 143 | 19.8 | 1.15 | 20.4 |
| FPT-Ph($CF_3$, F) | 142 | 4.40 | 2.57 | 83.4 | 55.3 | 1.71 | 32.5 |
| FPT-Ph(OH)/Ph(t-Bu) (1:0.86) | 157 | 8.97 | 7.19 | 192 | 24.6 | 1.25 | 26.7 |
| FPT-Ph(OH)/Ph($Me_2$) (1:0.82) | 126 | 4.90 | 3.36 | 116 | 37.5 | 1.46 | 34.5 |
| FPT-Ph(OH)/Ph($CF_3$, F) (1:0.13) | 119 | 3.20 | 1.65 | 86.2 | 71.7 | 1.93 | 52.1 |
| FPT-Ph(OH)/POz-$CF_3$ (1:1) | 148 | 5.11 | 3.12 | 101 | 47.4 | 1.63 | 32.3 |
| FPT-Ph(OH)/Ph($CF_3$, F) (1:0.91) | 140 | 4.90 | 2.81 | 91.7 | 49.8 | 1.75 | 32.7 |
| FPT-Ph(OH)/Ph($Me_2$) (1:1) | 128 | 5.19 | 3.69 | 102 | 34.6 | 1.41 | 27.7 |

The gas permeation studies of the copoly(1,2,4-triazole) membranes demonstrated the effect of the nature of aniline derivatives substituted to the polymer's backbone on its gas permeation properties. Moreover, the data provide information on the control that the design possesses over the membrane's permeability and selectivity coefficients. By fixing one substituent and changing the other, the $CO_2$ permeability can be increased to a desired value. However, due to the permeability-selectivity tradeoff relationship, the $CO_2/CH_4$ selectivity drops when the $CO_2$ permeability increases. For example, the performance of the two copoly(1,2,4-triazole) membranes FPT-Ph(OH)/Ph(t-Bu) and FPT-Ph(OH)/Ph($Me_2$) can be compared. Both copoly(1,2,4-triazole)s contain the aniline substituent Ph(OH), with similar molar ratio to Ph(t-Bu) and Ph($Me_2$), respectively. The $CO_2$ permeability increased by ~66% when the aniline substituent Ph($Me_2$) was replaced by the bulkier substituent Ph(t-Bu). The bulky tert-butyl group increases the fractional free volume (FFV) within the membrane matrix, leading to a faster diffusion of $CO_2$, and hence increasing its permeability coefficient. However, this phenomenon also increases the diffusion of all gas molecules, including $CH_4$, which leads to a drop in the $CO_2/CH_4$ selectivity coefficient. Hence the $CO_2/CH_4$ selectivity of FPT-Ph(OH)/Ph(t-Bu) decreased by ~23%.

Figure 14:
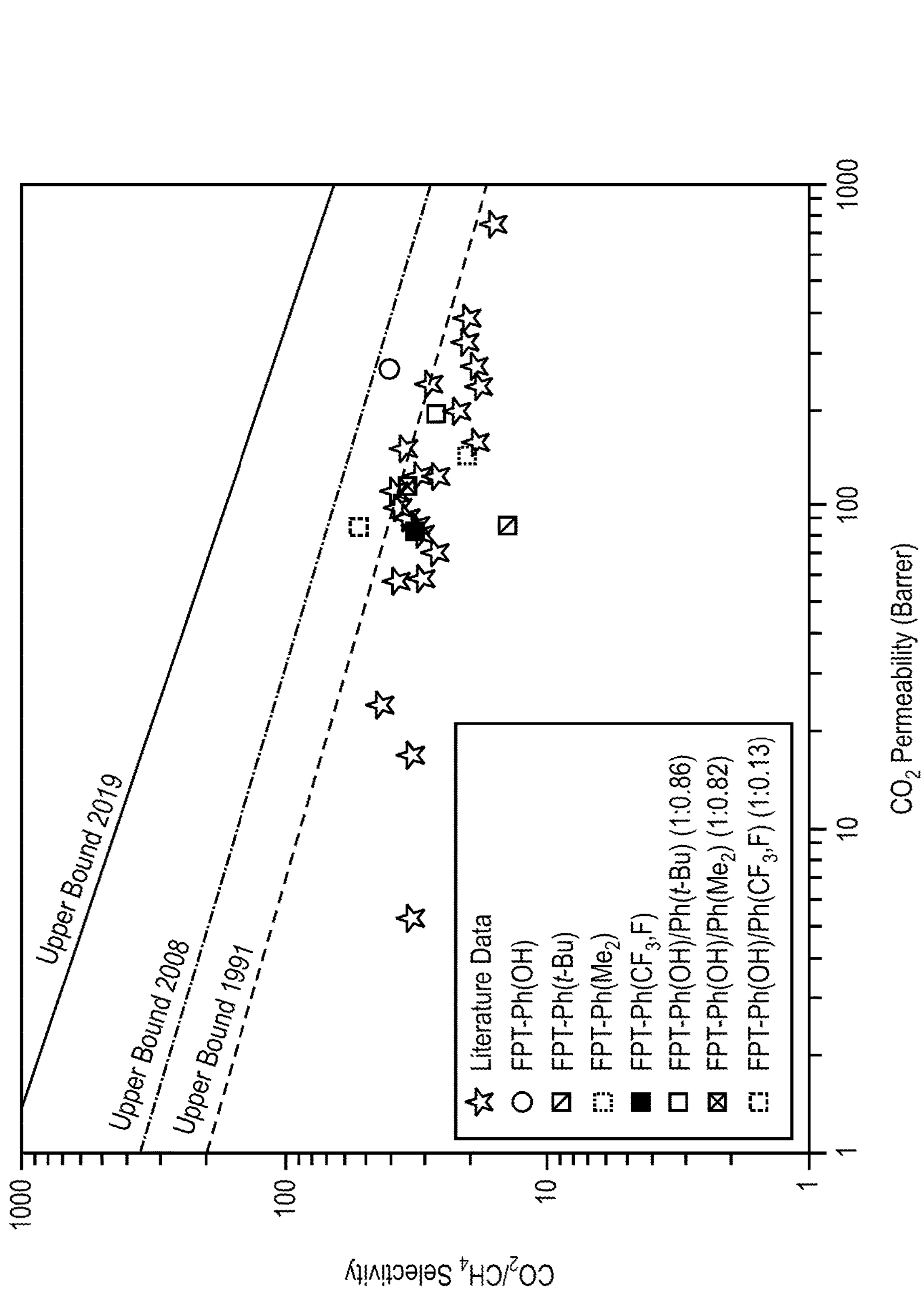
FIG. 14 shows illustrates the $CO_2/CH_4$ permeability-selectivity trade off.

In general, membranes prepared from glassy polymers suffer from permeability-selectivity trade off. FIG. 14 illustrates the $CO_2/CH_4$ permeability-selectivity trade off, as originally reported by Robeson and others. (Robeson, L. M. The Upper Bound Revisited. *J. Membr. Sci.* 320 (1), 390-400 (2008); Comesaña-Gándara, et al. Redefining the Robeson Upper Bounds for CO2/CH4 and CO2/N2 Separations Using a Series of Ultrapermeable Benzotriptycene-Based Polymers of Intrinsic Microporosity. *Energy Environ. Sci.,* 12 (9), 2733-2740 (2019)). This is also observed for the membranes described herein. However, the gas permeation properties of the copoly(1,2,4-triazole) membranes described herein afforded permeability and selectivity coefficients in the desired potential commercially favored range, with a $CO_2$ permeability around 100 Barrer, and $CO_2/CH_4$ selectivity around 30 Barrer.

Mixed-Gas Permeation Measurement

Since natural gas is a mixture of gases, it is important to study the mixed-gas separation performance of polymeric membranes. For a gas mixture, the determination of the permeability coefficients of individual gases is determined using a constant-pressure/variable-volume permeation system. The system allows the determination of the permeate gas composition; a set of data needed to determine the permeability coefficient of a particular gas A using the following expression:

$$P_A = P_{total}\frac{y_A(p_p - p_f)}{x_A p_p - y_A p_f}$$

where $P_{total}$ is the permeability of total gas particles permeated through the membrane, $x_A$ and $y_A$ are the mole fractions of gas A in the feed and the permeate sides, respectively, and are determined experimentally using a gas chromatography analyzer connected to the system. The terms $p_p$ and $p_f$ are the partial pressures of gas A in the feed and the permeate sides, respectively.

$P_{total}$ can be determined using the following expression:

$$P_{total} = \frac{Jl}{\Delta p}$$

where, J is the penetrant flux ($cm^3$(STP)·$cm^{-2}$·$s^{-1}$), l is the membrane thickness (cm) and Δp is the difference between the partial pressures of gas A at the feed and the permeate sides (cmHg).

The selectivity coefficient ($\alpha^*_{A/B}$) which is the ability of a polymeric membrane to separate a binary feed gas mixture, is defined as follows:

$$\alpha^*_{A/B} = \left(\frac{y_A}{y_B}\right) \times \left(\frac{x_B}{x_A}\right)$$

where $y_A$ and $y_B$ are the mole fractions of gases A and B at the permeate side, and $x_A$ and $x_B$ are the mole fractions of gases A and B at the feed side.

To reflect the real properties of the membrane in the case of a non-ideal gas mixture, the modified expression of the selectivity $$(\alpha^{m,*}_{AB})$$

is expressed by $$\alpha^{m,*}_{A/B} = \frac{P^*_A}{P^*_B}$$

where $$P^*_A \text{ and } P^*_B$$

are the mixed-gas permeability coefficients of components A and B.

The disclosed copoly(1,2,4-triazole)s membranes were subjected to a sweet mixed-gas containing 10, 60, 29 and 1 vol. % of $CO_2$, $CH_4$, $N_2$ and $C_2H_6$, respectively. The permeation measurements were recorded at different feed pressures (300-900 psi) at a fixed temperature of 22° C. The obtained results are listed in Table 4.

TABLE 4

Sweet mixed-gas permeability and selectivity coefficients of copoly(1,2,4-triazole)s fresh membranes at various feed pressures and 22° C.

| Membrane | P (psi) | Permeability coefficients (Barrer) $N_2$ | $CH_4$ | $CO_2$ | $C_2H_6$ | Selectivity coefficients $N_2$/$CH_4$ | $C_2H_6$/$CH_4$ | $CO_2$/$CH_4$ |
|---|---|---|---|---|---|---|---|---|
| FPT- | 300 | 3.84 | 4.05 | 110 | 3.99 | 0.95 | 0.987 | 27.1 |
| Ph(OH)/ | 500 | 3.41 | 3.66 | 90.9 | 3.39 | 0.93 | 0.926 | 24.8 |
| Ph(t-Bu) | 700 | 3.04 | 3.31 | 80.2 | 2.59 | 0.92 | 0.782 | 24.2 |
| (1:0.86) | 900 | 2.74 | 3.03 | 72.1 | 2.95 | 0.90 | 0.973 | 23.8 |
| Fresh | | | | | | | | |
| FPT- | 300 | 2.56 | 2.30 | 78.9 | 1.96 | 1.11 | 0.854 | 34.4 |
| Ph(OH)/ | 500 | 2.33 | 2.14 | 66.7 | 1.82 | 1.09 | 0.847 | 31.1 |
| Ph($Me_2$) | 700 | 2.10 | 1.94 | 57.1 | 1.69 | 1.08 | 0.868 | 29.4 |
| (1:0.82) | 900 | 1.88 | 1.82 | 50.4 | 1.58 | 1.03 | 0.869 | 27.7 |
| Fresh | | | | | | | | |
| FPT- | 300 | 1.48 | 1.11 | 50.1 | 0.834 | 1.33 | 0.750 | 45.0 |
| Ph(OH)/ | 500 | 1.35 | 1.03 | 41.4 | 0.846 | 1.31 | 0.822 | 40.2 |
| Ph($CF_3$, F) | 700 | 1.30 | 0.985 | 36.8 | 0.732 | 1.32 | 0.744 | 37.4 |
| (1:0.13) | 900 | 1.18 | 0.927 | 34.4 | 0.738 | 1.27 | 0.796 | 37.1 |
| Fresh | | | | | | | | |

Figure 15A:
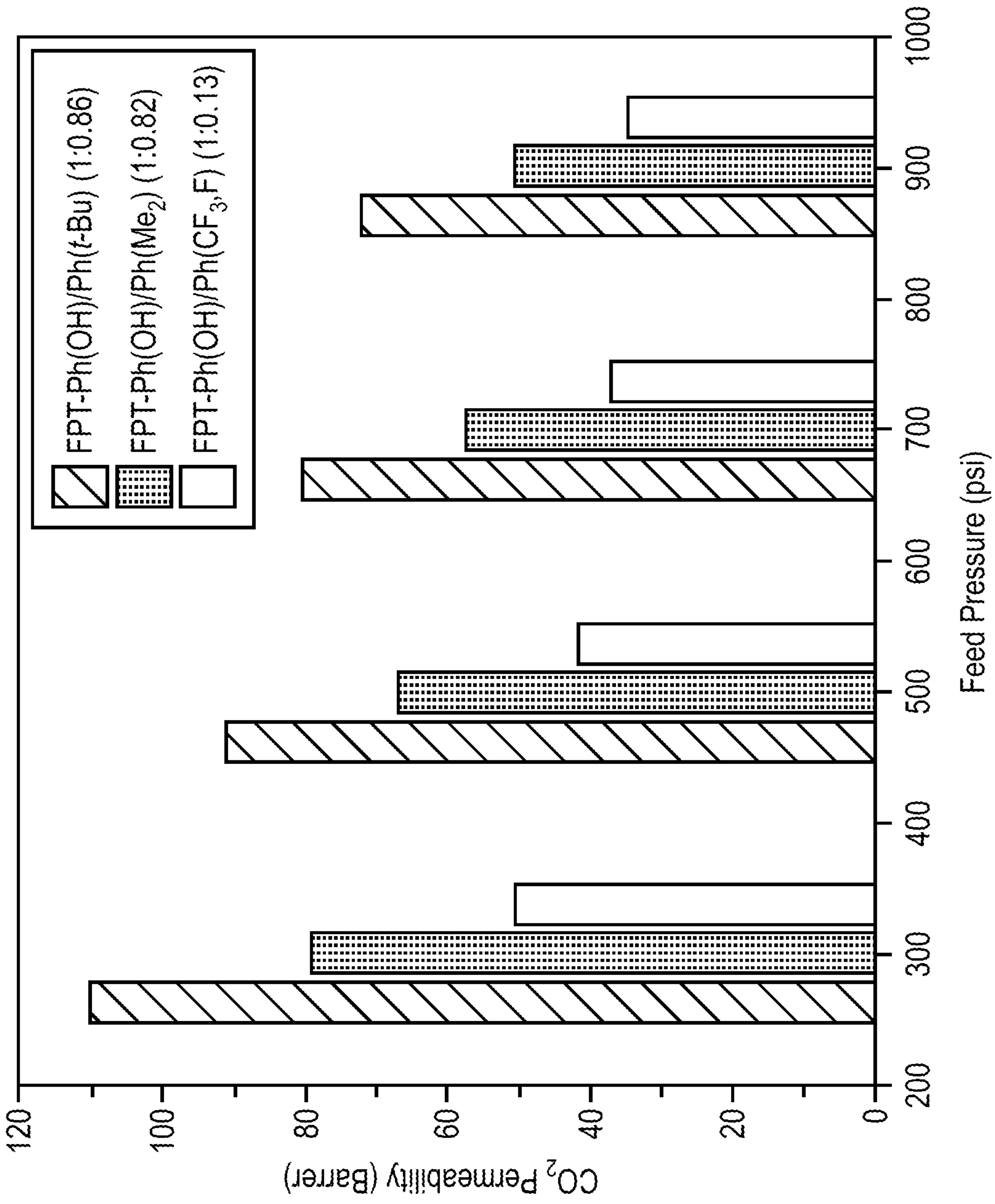
FIG. 15A shows the sweet mixed-gas $CO_2$ permeability of the copoly(1,2,4-triazole)s fresh membranes at various feed pressures and 22° C.
Figure 15B:
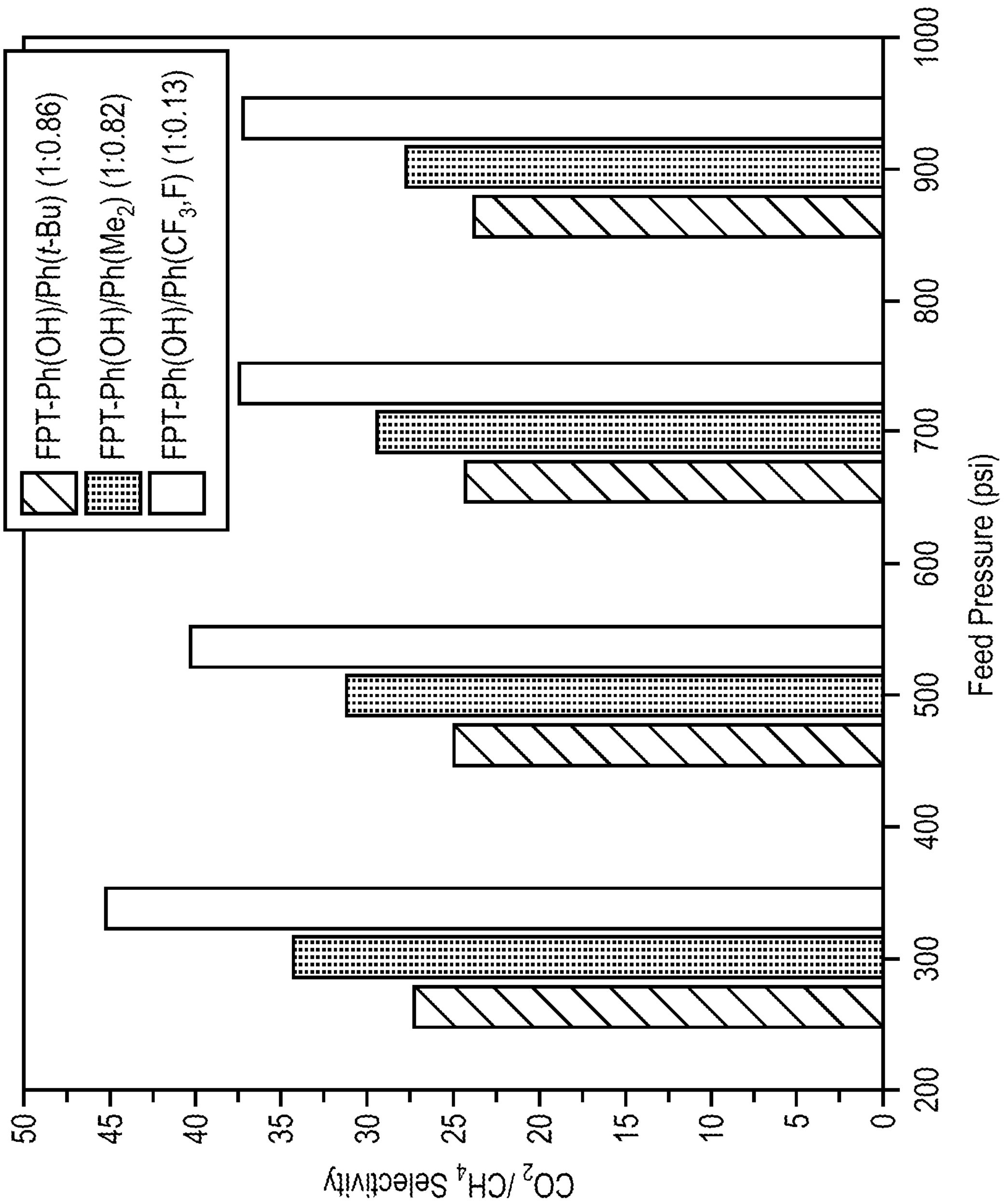
FIG. 15B shows the sweet mixed-gas $CO_2/CH_4$ selectivity coefficients of the copoly(1,2,4-triazole)s fresh membranes at various feed pressures and 22° C.

FIGS. 15A and 15B show another illustration of the data listed in Table 4. In FIGS. 15A and 15B, the $CO_2$ permeability and $CO_2/CH_4$ selectivity coefficients measured at various feed pressures were plotted in column charts. FIG. 15A shows the sweet mixed-gas $CO_2$ permeability of the copoly(1,2,4-triazole)s fresh membranes at various feed pressures and 22° C. FIG. 15B shows the sweet mixed-gas $CO_2/CH_4$ selectivity coefficients of the copoly(1,2,4-triazole)s fresh membranes at various feed pressures and 22° C. FIGS. 15A and 15B show the dependency of the permeation data based on the nature of the substituents grafted onto the copolymer backbone. Since the common feature between the three studied substituents is the van der Waals volume of the moiety (Table 2), the separation appears to be dominated by the diffusivity parameter. The $CO_2$ permeation increased in the following order: 4-tert-butylaniline ($V_w$=161.5 Å$^3$)>3,5-dimethylaniline ($V_w$=126.7 Å$^3$)>4-fluoro-3-trifluoromethylaniline ($V_w$=129.8 Å$^3$). Despite the higher van der Waals volume for 4-fluoro-3-trifluoromethylaniline compared to 3,5-dimethylaniline, the lower Ph($CF_3$,F)/Ph(OH) molar ratio compared to Ph($Me_2$)/Ph(OH) leads to lower $CO_2$ permeability coefficient in FPT-Ph(OH)/Ph($CF_3$,F) (1:0.13) compared to FPT-Ph(OH)/Ph($Me_2$) (1:0.82).

Moreover, the data in FIGS. 15A and 15B show a clear permeability-selectivity tradeoff relationship for all three copoly(1,2,4-triazole)s, which confirms that the separation is diffusivity-selective. The data correlates in a perfect manner with the fractional free volume measurements listed in Table 2: FPT-Ph(OH)/Ph(t-Bu) (1:0.86) (FFV=0.1821)>FPT-Ph(OH)/Ph($Me_2$) (1:0.82) (FFV=0.1711)>FPT-Ph(OH)/Ph($CF_3$,F) (1:0.13) (FFV=0.1689). In addition, the mixed-gas $CO_2$ permeability coefficients of all copoly(1,2,4-triazole)s decreased when the feed pressure increased from 300 to 900 psi, indicating compression of the membrane, which leads to a reduction in the excess free volume within the membranes' matrices and the absence of membrane plasticization.

Furthermore, aged copoly(1,2,4-triazole)s membranes were re-tested using the same sweet gas mixture under the same conditions of feed pressures and temperature. The membranes were over 490 days of age since they were first cast. During this period, the membranes were kept in a non-airtight plastic container under ambient conditions. The obtained permeation data are listed in Table 5.

TABLE 5

Sweet mixed-gas permeability and selectivity coefficients of copoly(1,2,4-triazole)s aged membranes at various feed pressures and 22° C.

| Membrane (aging time in days) | P (psi) | Permeability coefficients (Barrer) $N_2$ | $CH_4$ | $CO_2$ | $C_2H_6$ | Selectivity coefficients $N_2$/$CH_4$ | $C_2H_6$/$CH_4$ | $CO_2$/$CH_4$ |
|---|---|---|---|---|---|---|---|---|
| FPT- | 300 | 2.59 | 2.57 | 79.4 | 1.19 | 1.01 | 0.463 | 30.9 |
| Ph(OH)/ | 500 | 2.60 | 2.62 | 76.4 | 1.64 | 0.992 | 0.626 | 29.2 |
| Ph(t-Bu) | 700 | 2.33 | 2.41 | 68.1 | 1.53 | 0.967 | 0.635 | 28.3 |
| (1:0.86) | 900 | 2.08 | 2.20 | 62.1 | 1.34 | 0.945 | 0.609 | 28.2 |
| Aged | | | | | | | | |
| (501 days) | | | | | | | | |
| FPT- | 300 | 1.75 | 1.48 | 58.6 | 0.665 | 1.18 | 0.449 | 39.6 |
| Ph(OH)/ | 500 | 1.39 | 1.19 | 44.1 | 0.382 | 1.17 | 0.321 | 37.1 |
| Ph($Me_2$) | 700 | 1.45 | 1.28 | 42.9 | 0.614 | 1.13 | 0.480 | 33.5 |
| (1:0.82) | 900 | 1.49 | 1.36 | 43.1 | 0.878 | 1.10 | 0.646 | 31.7 |
| Aged | | | | | | | | |
| (513 days) | | | | | | | | |
| FPT- | 300 | 1.05 | 0.760 | 36.2 | 0.387 | 1.38 | 0.510 | 47.7 |
| Ph(OH)/ | 500 | 0.755 | 0.541 | 26.5 | 0.172 | 1.40 | 0.318 | 49.0 |
| Ph($CF_3$, F) | 700 | 0.733 | 0.541 | 25.4 | 0.182 | 1.35 | 0.336 | 47.0 |
| (1:0.13) | 900 | 0.686 | 0.514 | 23.7 | 0.246 | 1.33 | 0.478 | 46.1 |
| Aged | | | | | | | | |
| (492 days) | | | | | | | | |

Figure 16A:
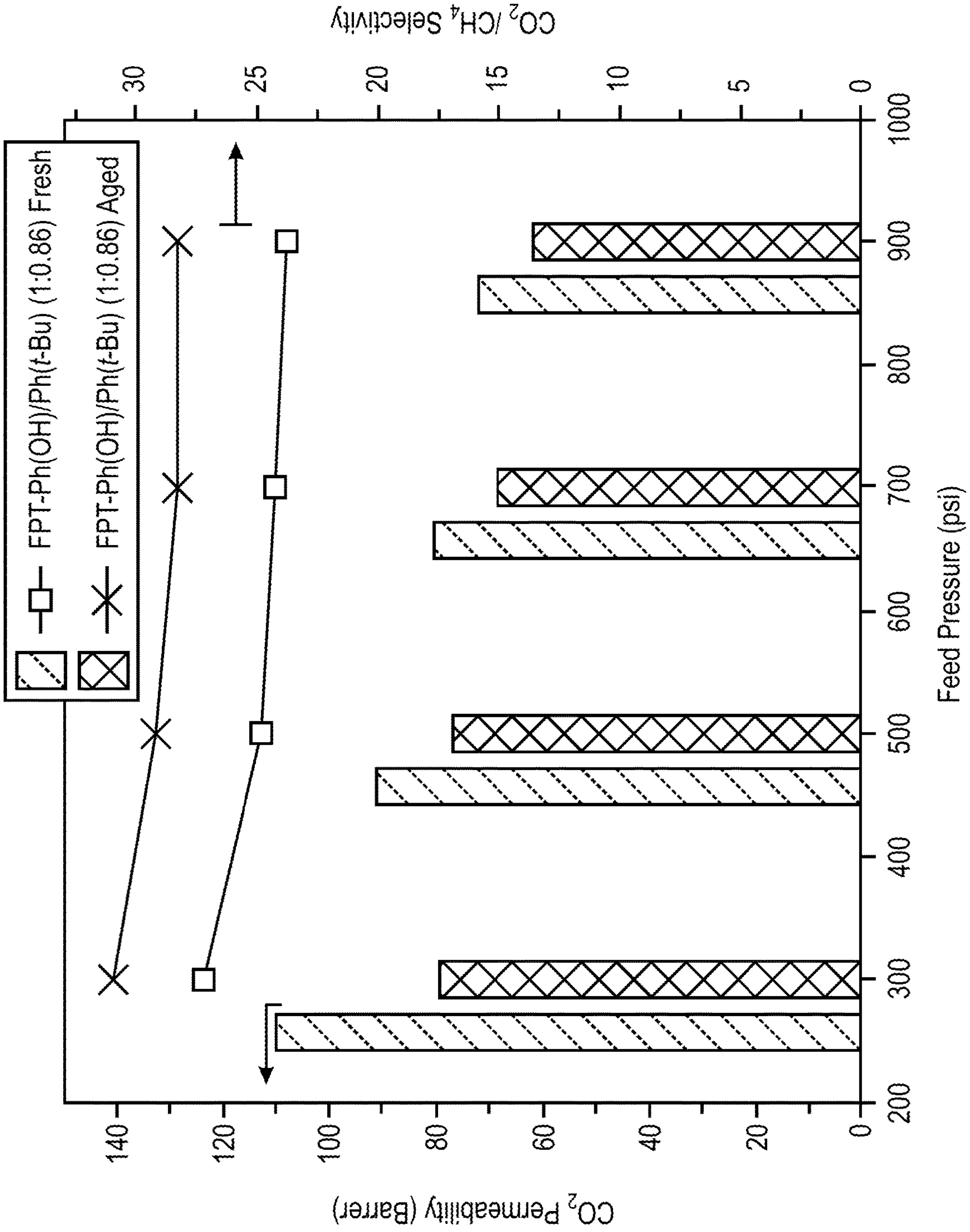
FIG. 16A shows the sweet mixed-gas $CO_2$ permeability and $CO_2/CH_4$ selectivity coefficients of fresh and aged FTP-Ph(OH)/Ph(t-Bu) membranes.
Figure 16B:
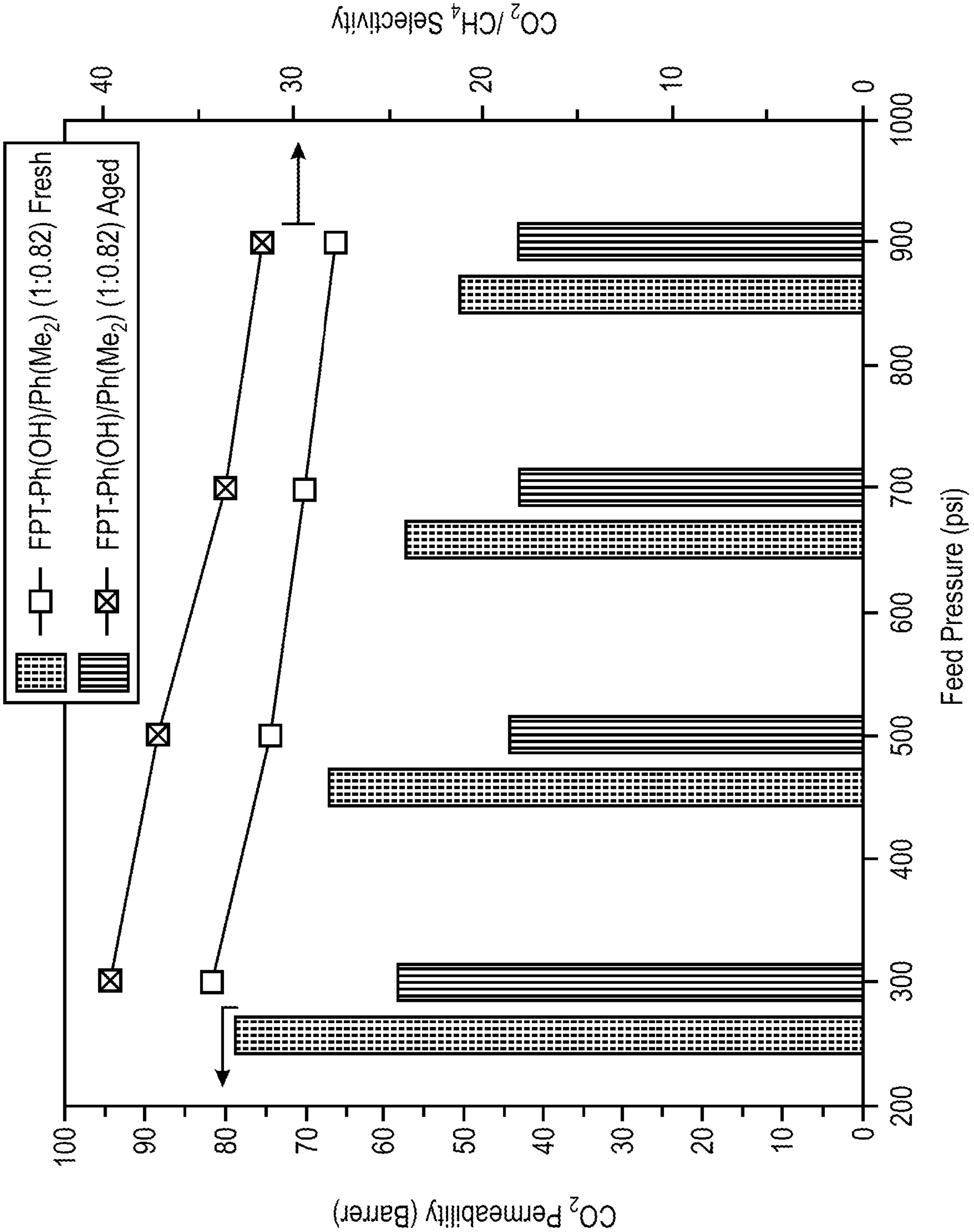
FIG. 16B shows the sweet mixed-gas $CO_2$ permeability and $CO_2/CH_4$ selectivity coefficients of the fresh and aged FTP-Ph(OH)/Ph(t-$Me_2$) membranes.
Figure 16C:
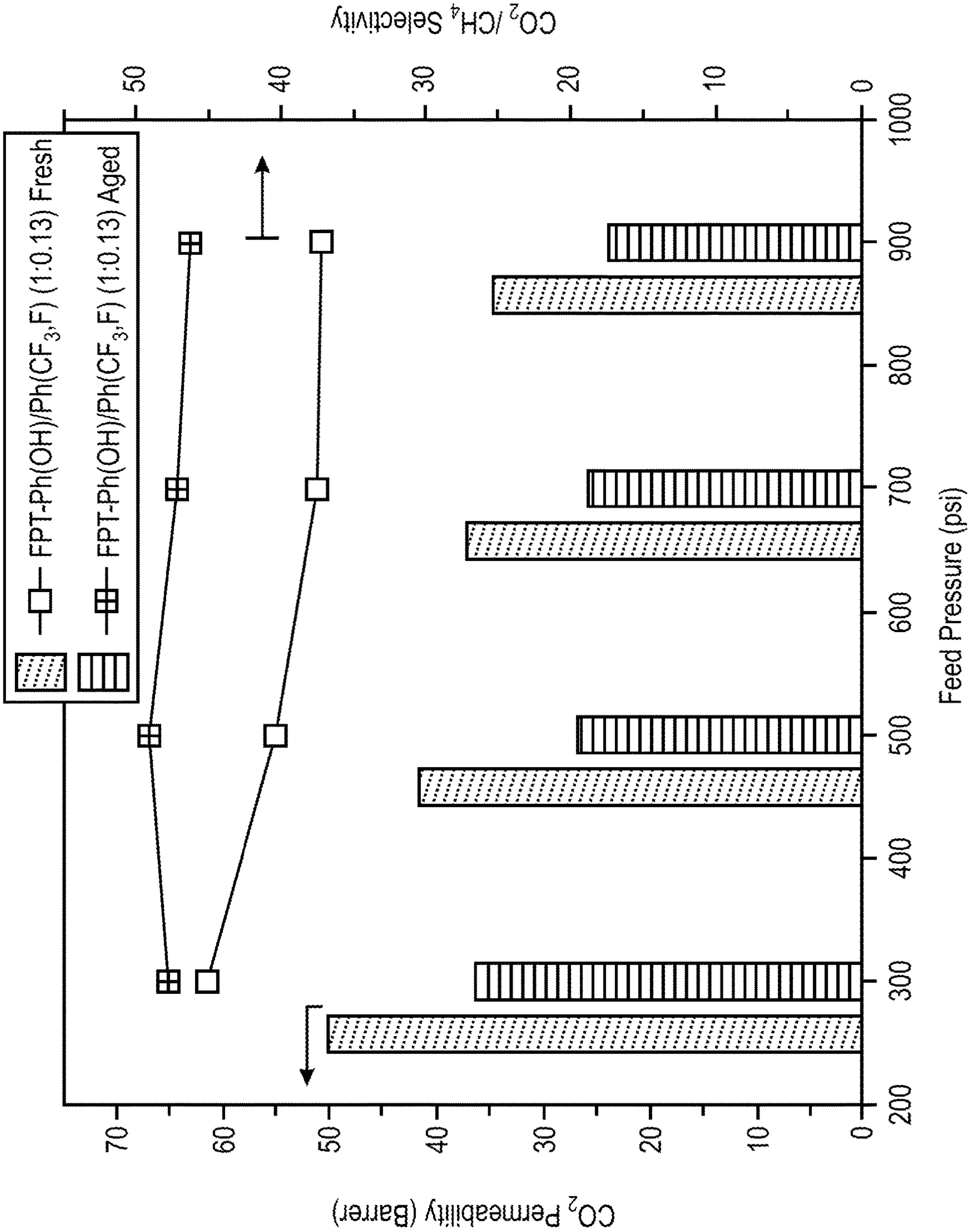
FIG. 16C shows the sweet mixed-gas $CO_2$ permeability and $CO_2/CH_4$ selectivity coefficients of the fresh and aged FTP-Ph(OH)/Ph($CF_3$,F) membranes.

To compare the performance of aged membranes to the fresh ones, the $CO_2$ permeability and $CO_2/CH_4$ selectivity coefficients of each corresponding pairs of copoly(1,2,4-triazole)s were plotted into one chart, as illustrated in FIGS. 16A-16C. FIG. 16A shows the sweet mixed-gas $CO_2$ permeability and $CO_2/CH_4$ selectivity coefficients of the fresh and aged FTP-Ph(OH)/Ph(t-Bu) membranes. FIG. 16B shows the sweet mixed-gas $CO_2$ permeability and $CO_2/CH_4$ selectivity coefficients of the fresh and aged FTP-Ph(OH)/Ph(t-$Me_2$) membranes. FIG. 16C shows the sweet mixed-gas $CO_2$ permeability and $CO_2/CH_4$ selectivity coefficients of the fresh and aged FTP-Ph(OH)/Ph($CF_3$,F) membranes.

For all studied copoly(1,2,4-triazole)s pairs (i.e., fresh and aged), the aging affected the performance of the membrane in the following manner: (1) the mixed-gas $CO_2$ permeability coefficient decreased, and (2) the $CO_2/CH_4$ selectivity coefficients increased, under all feed pressures tested (300 psi to 900 psi). The results of permeability-selectivity tradeoff relationship are indicative of a change in the excess free volume within the membrane matrix, which affected the sieving properties of the membrane, due to the separation being dominated by the diffusivity parameter, as described herein. The performance of the aged membrane is still considered attractive, since the loss of the membrane productivity is compensated by the gain in its efficiency.

In an attempt to regenerate the performance of the aged membranes, the membranes were annealed at a temperature of 200° C. for 24 hours under vacuum. The annealed membranes were re-tested using the same sweet gas mixture under the same conditions of feed pressures and temperature. The obtained results are listed in Table 6.

TABLE 6

Sweet mixed-gas permeability and selectivity coefficients of copoly(1,2,4-triazole)s annealed membranes at 200° C. and tested at various feed pressures at 22° C.

| Membrane | P (psi) | Permeability coefficients (Barrer) $N_2$ | $CH_4$ | $CO_2$ | $C_2H_6$ | Selectivity coefficients $N_2/CH_4$ | $C_2H_6/CH_4$ | $CO_2/CH_4$ |
|---|---|---|---|---|---|---|---|---|
| FPT-Ph(OH)/ | 300 | 4.04 | 4.17 | 117 | 3.82 | 0.97 | 0.916 | 28.1 |
| Ph(t-Bu) | 500 | 3.74 | 3.95 | 99.1 | 3.70 | 0.95 | 0.937 | 25.1 |
| (1:0.86) | 700 | 3.42 | 3.68 | 87.3 | 3.47 | 0.93 | 0.943 | 23.7 |
| Annealed @200° C. | 900 | 3.15 | 3.46 | 79.0 | 3.31 | 0.91 | 0.957 | 22.8 |
| FPT-Ph(OH)/ | 300 | 2.17 | 1.91 | 71.9 | 1.58 | 1.14 | 0.826 | 37.7 |
| Ph($Me_2$) | 500 | 2.01 | 1.79 | 62.1 | 1.42 | 1.12 | 0.791 | 34.6 |
| (1:0.82) | 700 | 1.94 | 1.78 | 56.7 | 1.38 | 1.09 | 0.773 | 31.9 |
| Annealed @200° C. | 900 | 1.86 | 1.75 | 50.1 | 1.356 | 1.06 | 0.774 | 28.6 |
| FPT- | 300 | 1.73 | 1.27 | 58.8 | 0.835 | 1.37 | 0.659 | 46.4 |
| Ph(OH)/ | 500 | 1.44 | 1.066 | 47.9 | 0.511 | 1.35 | 0.480 | 45.0 |
| Ph($CF_3$, F) | 700 | 1.34 | 0.991 | 41.7 | 0.480 | 1.35 | 0.484 | 42.1 |
| (1:0.13) | 900 | 1.36 | 1.065 | 39.5 | 0.688 | 1.27 | 0.646 | 37.1 |
| Annealed @200° C. | | | | | | | | |

Figure 17A:
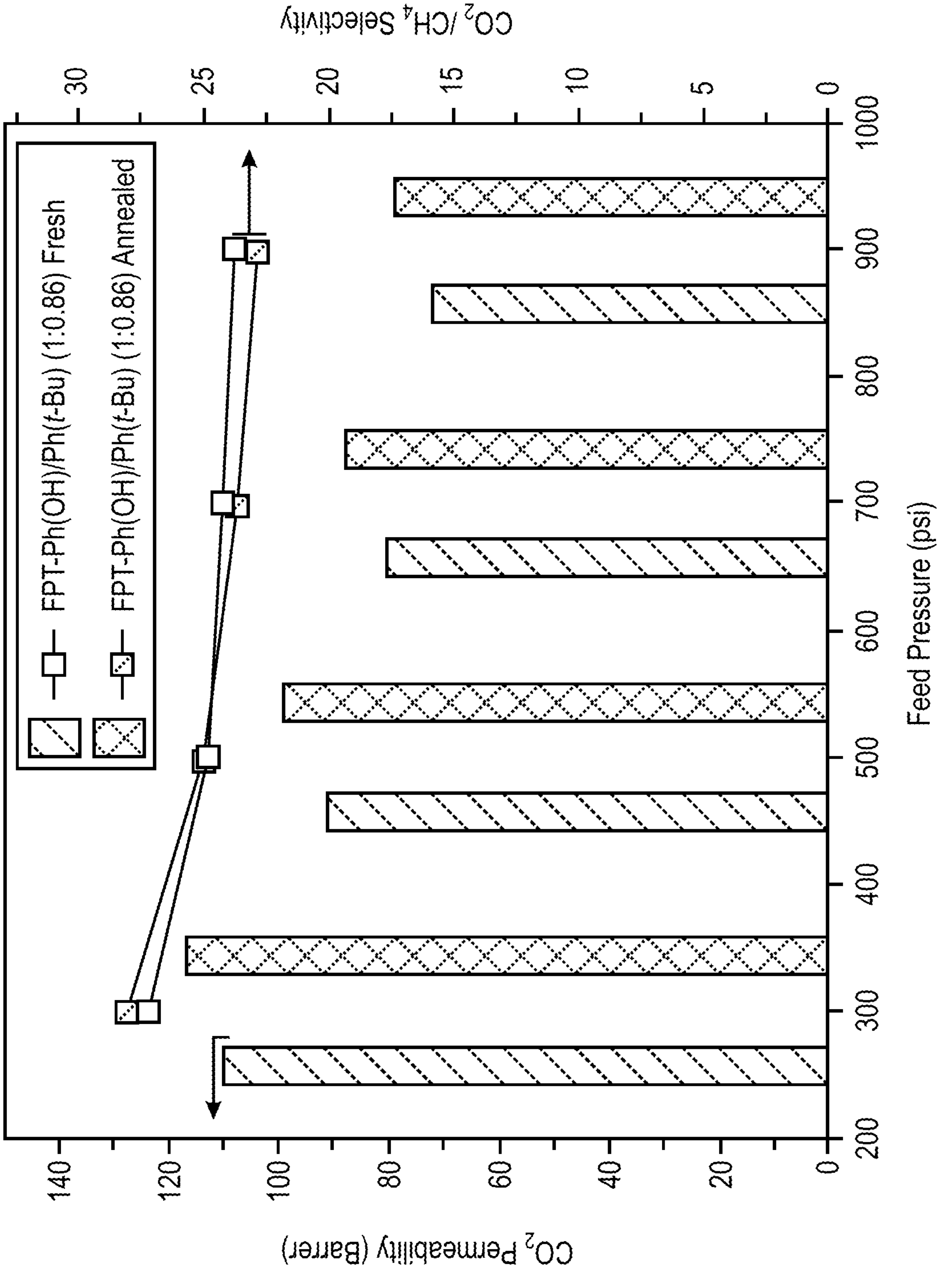
FIG. 17A shows a column chart of the sweet mixed-gas $CO_2$ permeability and $CO_2/CH_4$ selectivity coefficients of FPT-Ph(OH)/Ph(t-Bu) fresh and annealed membranes at various feed pressures and 22° C.
Figure 17B:
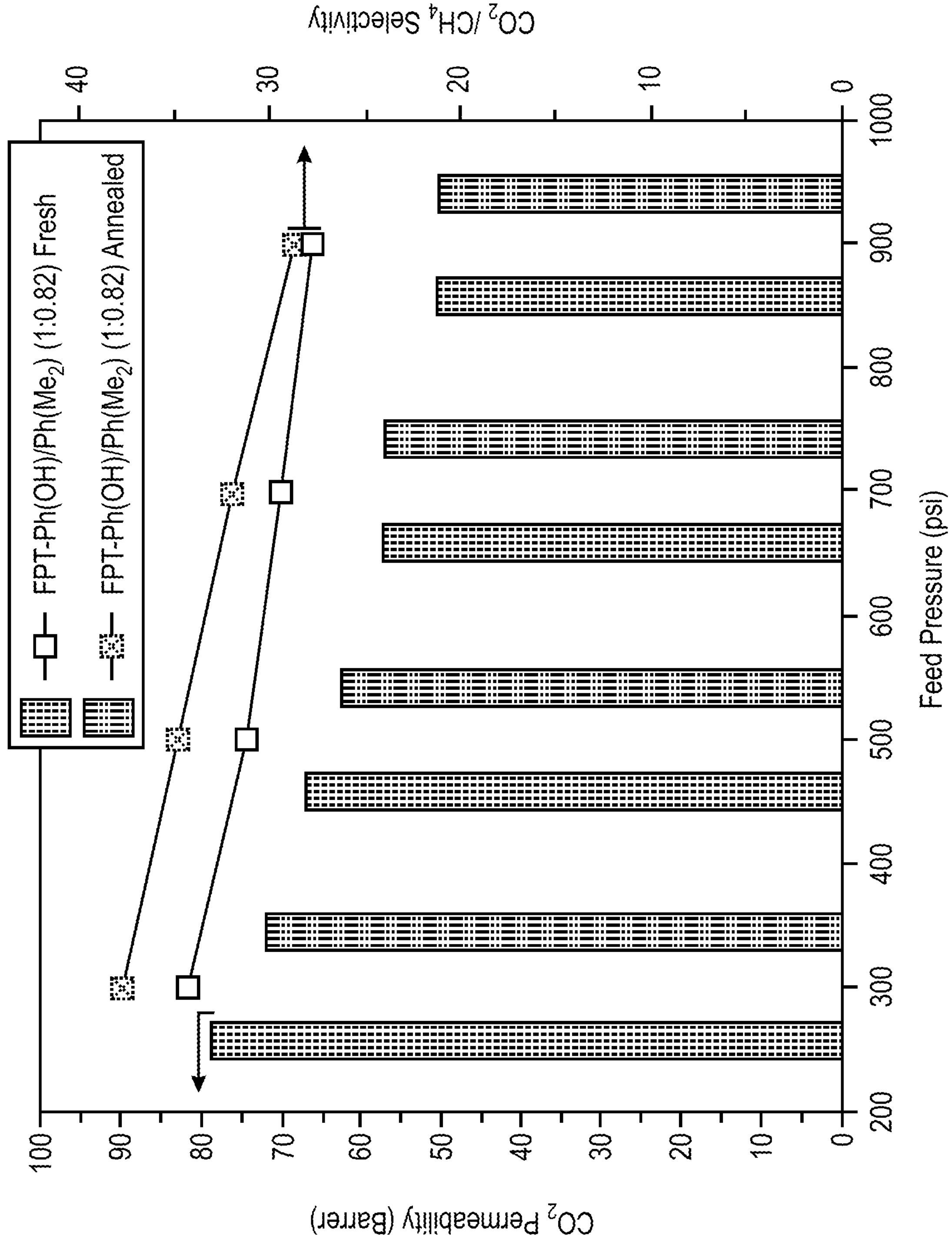
FIG. 17B shows a column chart of the sweet mixed-gas $CO_2$ permeability and $CO_2/CH_4$ selectivity coefficients of FPT-Ph(OH)/Ph($Me_2$) fresh and annealed membranes at various feed pressures and 22° C.
Figure 17C:
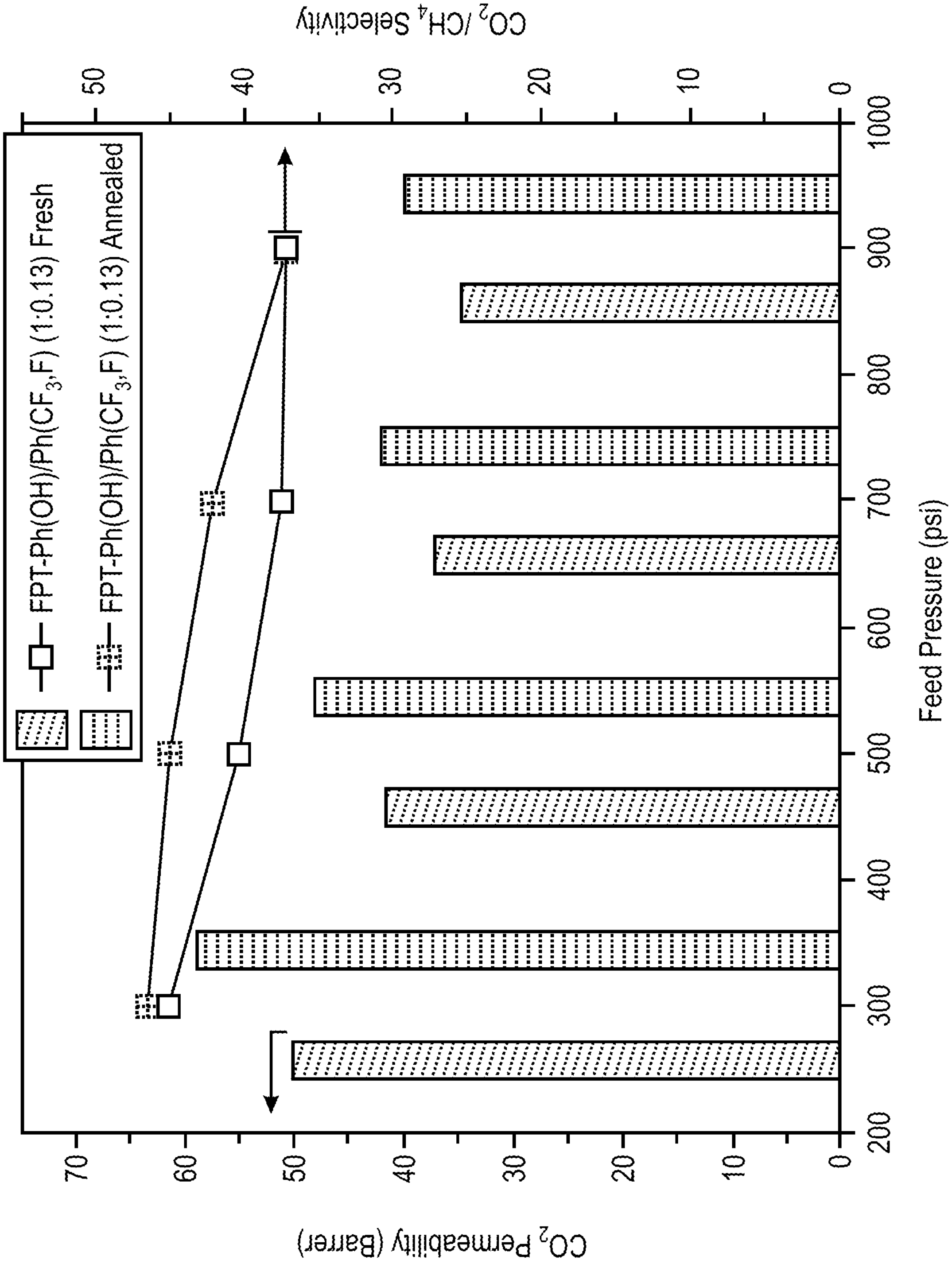
FIG. 17C shows a column chart of the sweet mixed-gas $CO_2$ permeability and $CO_2/CH_4$ selectivity coefficients of FPT-Ph(OH)/Ph($CF_3$,F) fresh and annealed membranes at various feed pressures and 22° C.

The $CO_2$ permeability and $CO_2/CH_4$ selectivity coefficients of each corresponding pair of copoly(1,2,4-triazole)s were plotted into one chart, as shown in FIGS. 17A-17C. FIG. 17A shows a column chart of the sweet mixed-gas $CO_2$ permeability and $CO_2/CH_4$ selectivity coefficients of FPT-Ph(OH)/Ph(t-Bu) fresh and annealed membranes at various feed pressures and 22° C. FIG. 17B shows a column chart of the sweet mixed-gas $CO_2$ permeability and $CO_2/CH_4$ selectivity coefficients of FPT-Ph(OH)/Ph($Me_2$) fresh and annealed membranes at various feed pressures and 22° C. FIG. 17C shows a column chart of the sweet mixed-gas $CO_2$ permeability and $CO_2/CH_4$ selectivity coefficients of FPT-Ph(OH)/Ph($CF_3$,F) fresh and annealed membranes at various feed pressures and 22° C. The obtained results showed that the rejuvenated membranes through thermal annealing possess slightly better performance depending on the nature of the membrane: better $CO_2$ permeability and/or better $CO_2/CH_4$ selectivity. These results are unexpected and beneficial, since the performance of the membranes can be rejuvenated and further improved with thermal annealing.

Furthermore, the sweet mixed-gas separation performance of the FPT-Ph(OH)/POz-$CF_3$ (1:1) membrane was tested using the same sweet gas mixture under various feed pressures (up to 900 psi) and 22° C. The obtained permeation data are listed in Table 7. Despite the fact that FPT-Ph(OH)/POz-$CF_3$ (1:1) was prepared as an intermediate to control the molecular weight of the substituents in copoly(1,2,4-triazole)s, the mixed-gas separation performance of its membranes are very attractive. The membrane exhibits relatively high $CO_2/CH_4$ selectivity across all the feed pressures used. For example, at 900 psi, the $CO_2$ permeability is measured as 48.9 Barrer with a $CO_2/CH_4$ selectivity of 32.5. These results are considered attractive for such a multicomponent mixture (quaternary mixture) and at such high testing pressure.

Additionally, fresh membranes prepared from FPT-Ph(OH)/Ph($Me_2$) (1:1) and FPT-Ph(OH)/Ph($CF_3$,F) (1:0.91) were tested under the same mixed-gas conditions to evaluate the effect of the change in the molecular weight between the different substituents: Ph(X)/Ph(OH); where Ph(X) being Ph($Me_2$) or Ph($CF_3$,F). The obtained permeation data are listed in Table 7.

TABLE 7

Sweet mixed-gas permeability and selectivity coefficients of copoly(1,2,4-triazole)s fresh membranes at various feed pressures and 22° C.

| Membrane | P (psi) | Permeability coefficients (Barrer) $N_2$ | $CH_4$ | $CO_2$ | $C_2H_6$ | Selectivity coefficients $N_2/CH_4$ | $C_2H_6/CH_4$ | $CO_2/CH_4$ |
|---|---|---|---|---|---|---|---|---|
| FPT- | 300 | 2.38 | 1.87 | 72.2 | 1.38 | 1.27 | 0.742 | 38.7 |
| Ph(OH)/ | 500 | 2.09 | 1.69 | 59.0 | 1.35 | 1.24 | 0.797 | 34.9 |
| POz- | 700 | 1.87 | 1.54 | 51.7 | 1.20 | 1.21 | 0.780 | 33.5 |
| $CF_3$ | 900 | 1.80 | 1.51 | 48.9 | 1.15 | 1.19 | 0.767 | 32.5 |

TABLE 7-continued

Sweet mixed-gas permeability and selectivity coefficients of copoly(1,2,4-triazole)s fresh membranes at various feed pressures and 22° C.

| | | Permeability coefficients | | | | Selectivity coefficients | | |
|---|---|---|---|---|---|---|---|---|
| | P | (Barrer) | | | | $N_2$/ | $C_2H_6$/ | $CO_2$/ |
| Membrane | (psi) | $N_2$ | $CH_4$ | $CO_2$ | $C_2H_6$ | $CH_4$ | $CH_4$ | $CH_4$ |
| (1:1) | | | | | | | | |
| Fresh | | | | | | | | |
| FPT- | 300 | 2.71 | 2.55 | 81.5 | 2.18 | 1.06 | 0.855 | 32.0 |
| Ph(OH)/ | 500 | 2.47 | 2.37 | 67.2 | 2.08 | 1.04 | 0.878 | 28.4 |
| $Ph(Me_2)$ | 700 | 2.27 | 2.23 | 58.5 | 1.97 | 1.02 | 0.883 | 26.2 |
| (1:1) | 900 | 2.16 | 2.11 | 55.8 | 1.91 | 1.02 | 0.905 | 26.4 |
| Fresh | | | | | | | | |
| FPT- | 300 | 2.63 | 1.99 | 75.1 | 1.36 | 1.32 | 0.685 | 37.7 |
| Ph(OH)/ | 500 | 2.28 | 1.74 | 62.9 | 1.13 | 1.31 | 0.649 | 36.2 |
| $Ph(CF_3, F)$ | 700 | 2.06 | 1.61 | 52.9 | 1.03 | 1.27 | 0.639 | 32.7 |
| (1:0.91) | 900 | 1.93 | 1.55 | 47.7 | 1.13 | 1.25 | 0.732 | 30.8 |
| Fresh | | | | | | | | |

Since among other reasons, $Ph(Me_2)$ or $Ph(CF_3,F)$ are added to the copolymer backbone to disrupt the polymeric chains packing within the membrane matrix, it is observed that when the Ph(X)/Ph(OH) molar ratio is increased, the mixed-gas $CO_2$ permeability increases. However, due to the permeability-selectivity tradeoff relationship, the $CO_2/CH_4$ selectivity decreased accordingly. These results show that the separation properties of copoly(1,2,4-triazole)s membranes can be tailored through changing the nature and/or molar ratio of the substituents grafted onto the backbone. This molecular design methodology can be applied to target highly permeable or highly selective membranes, according to the gas mixture to purify.

Methods of Using the Membranes

The membranes of the present disclosure possess a set of specifications related to their gas permeability (or permeance) ($H_2S$ and $CO_2$) and selectivity ($CO_2/CH_4$ and $H_2S/CH_4$) that allow the membranes to be used in gas separation technologies. The membranes of the present disclosure can be used in a bulk acid gas removal process. In some implementations, the membranes of the present disclosure can be used in gas separation applications as hollow fiber membranes or spiral wound membranes. In some implementations, the thickness of the membranes described herein is between 0.5 μm to 5 μm.

Thus, also provided in the present disclosure are methods for using a membrane of the present disclosure. In some embodiments, the methods include separating $CO_2$, $H_2S$, or both from natural gas by introducing a natural gas stream to any membrane of the present disclosure, and separating the $CO_2$, $H_2S$, or both from the natural gas stream. In some embodiments, the natural gas stream includes about 1 vol % to about 30 vol % of $CO_2$ before separating. For example, in some embodiments, the natural gas stream includes about 1 vol % to about 20 vol %, about 1 vol % to about 15 vol %, about 3 vol % to about 30 vol %, about 3 vol % to about 20 vol %, or about 3 vol % to about 15 vol % of $CO_2$ before separating. In some embodiments, the natural gas stream includes about 1 vol % to about 40 vol % of $H_2S$ before separating. For example, in some embodiments, the natural gas stream includes about 1 vol % to about 30 vol %, about 1 vol % to about 25 vol %, about 5 vol % to about 40 vol %, about 5 vol % to about 30 vol %, or about 5 vol % to about 25 vol % of $H_2S$ before separating.

In some embodiments, the natural gas stream includes at least about 30 vol %, for example, at least about 40 vol %, or at least about 50 vol % of $CH_4$ before separating. In some embodiments, the natural gas stream further includes $N_2$, $C_2H_6$, or both.

Instrumentation and Methods

Fourier-transform infrared (FTIR) spectra were obtained using a Thermo Scientific Nicolet iS50 spectrometer in transmission mode. The spectra were recorded in the range of 4000-600 $cm^{-1}$ using either a thin polymeric film cast or a bulk solid polymer directly. $^1H$ NMR spectra were recorded on a JEOL 500 MHz NMR spectrometer in deuterated DMSO (DMSO-d6) or deuterated chloroform ($CDCl_3$) with tetramethylsilane (TMS) as the internal reference.

The thermal stability of polymer film specimens was performed by thermogravimetric analysis (TGA) using a NETZSCH STA 449 F3 Jupiter®, operating at a heating rate of 10° C.·$min^{-1}$ under a nitrogen flow, between 30° C. to 650° C. The DSC traces were recorded using the same instrument over two consecutive cycles. Both cycles were performed at a heating rate of 10° C.·$min^{-1}$ under a nitrogen flow, from 30° C. to 450° C. The first cycle was performed to remove the thermal history within the polymeric chains, followed by a fast cooling using a liquid nitrogen cooling system, then the glass transition temperature (Tg) was determined in the second heating cycle.

Chemical Characterizations:

The proton nuclear magnetic resonance ($^1H$ NMR) technique during the preparation of the disclosed copoly(1,2,4-triazole)s provides for the ability to ensure the full conversion of all the 1,3,4-oxadiazole rings into their corresponding 1,2,4-triazole rings, and to calculate the exact molar ratio between the various aniline derivatives used to prepare the copoly(1,2,4-triazole). The proton ($^1H$) spectra were recorded on a JEOL 500 MHz NMR spectrometer in deuterated chloroform or dimethylsulfoxide (DMSO-$d_6$).

A number of implementations of the disclosure have been described. Nevertheless, it will be understood that various modifications may be made without departing from the spirit and scope of the disclosure.

What is claimed is:

1. A polymer comprising:

a monomer unit of Formula VIIa:

(VIIa)

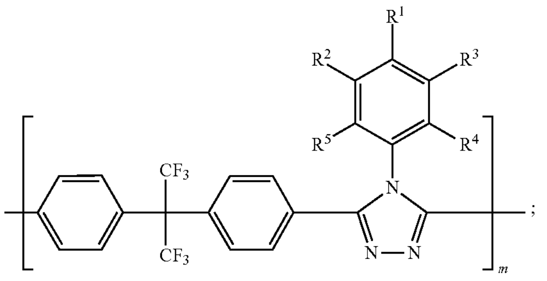

and a monomer unit of Formula VIIIa:

(VIIIa)

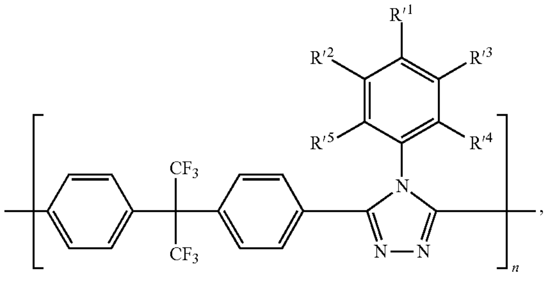

wherein $R^1$ is hydroxyl;

$R^2$-$R^5$ are hydrogen;

$R'^2$ is methyl;

$R'^3$ is methyl; and $R'^1$, $R'^4$, and $R'^5$ are each hydrogen, wherein the ratio of min is between 1:10 and 10:1 and wherein the polymer has a number-average molecular weight of about 1,000 g/mol to about 1,000,000 g/mol.

2. The polymer of claim 1, wherein the polymer comprises the monomer unit of Formula VIIa and the monomer unit of Formula VIIIa in a molar ratio of about 2:1 to about 1:2.

3. The polymer of claim 1, wherein the polymer comprises the monomer unit of Formula VIIa and the monomer unit of Formula VIIIa in a molar ratio of about 1:1.

4. The polymer of claim 1, having a number-average molecular weight of about 100,000 g/mol to 500,000 g/mol.

5. The polymer of claim 1, wherein the polymer is covalently crosslinked.

6. A membrane comprising the polymer of claim 1.

7. The membrane of claim 6, wherein the polymer is covalently crosslinked.

8. The membrane of claim 6, comprising at least about 80 wt % of the polymer.

9. A method for separating $CO_2$ and $H_2S$ from natural gas, the method comprising:

introducing a natural gas stream to the membrane of claim 6; and separating the $CO_2$ and $H_2S$ from the natural gas stream.

10. A polymer comprising:

a monomer unit of Formula VIIa:

(VIIa)

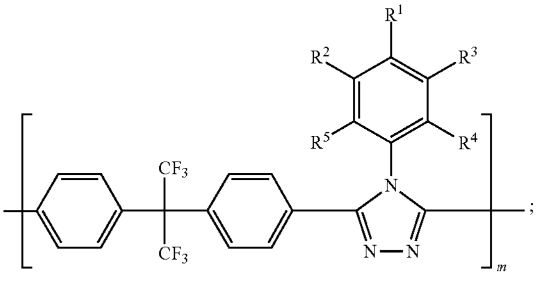

and a monomer unit of Formula VIIIa:

(VIIIa)

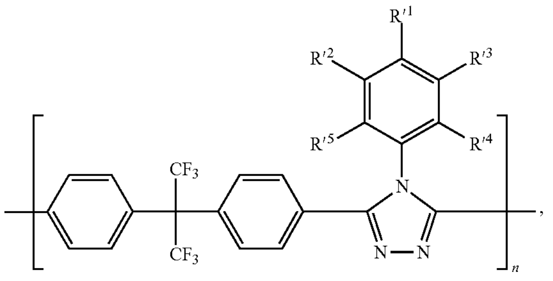

wherein $R^2$ is-$CH_2$—Br;

$R^3$ is methyl;

$R^1$, $R^4$, and $R^5$ are each hydrogen; and $R'^1$—$R'^5$ are each independently selected from hydrogen, alkyl, hydroxyl, alkoxy, halogen, aromatic, and cyclic functional groups, at least one of $R'^1$—$R'^5$ is not hydrogen, and wherein at least one of $R^1$-$R^5$ is different from at least one of $R'^1$—$R'^5$, wherein the ratio of m:n is between 1:10 and 10:1 and wherein the polymer has a number-average molecular weight of about 1,000 g/mol to about 1,000,000 g/mol.

11. The polymer of claim 10, wherein the polymer comprises the monomer unit of Formula VIIa and the monomer unit of Formula VIIIa in a molar ratio of about 2:1 to about 1:2.

12. The polymer of claim 10, wherein the polymer comprises the monomer unit of Formula VIIa and the monomer unit of Formula VIIIa in a molar ratio of about 1:1.

13. The polymer of claim 10, having a number-average molecular weight of about 100,000 g/mol to 500,000 g/mol.

14. The polymer of claim 10, wherein the polymer is covalently crosslinked.

15. A membrane comprising the polymer of claim 10.

16. The membrane of claim 15, wherein the polymer is covalently crosslinked.

17. The membrane of claim 15, comprising at least about 80 wt % of the polymer.

18. A method for separating $CO_2$ and $H_2S$ from natural gas, the method comprising:

introducing a natural gas stream to the membrane of claim 15; and separating the $CO_2$ and $H_2S$ from the natural gas stream.

* * * * *